United States Patent
Bontchev et al.

(10) Patent No.: US 10,301,228 B2
(45) Date of Patent: *May 28, 2019

(54) ENHANCED BIOCHAR

(71) Applicant: Cool Planet Energy Systems, Inc., Greenwood Village, CO (US)

(72) Inventors: Ranko Panayatov Bontchev, Camarillo, CA (US); Han Suk Kim, Thousand Oaks, CA (US); Richard W. Wilson, San Diego, CA (US); Richard Wilson Belcher, Oxnard, CA (US); Cameron Cheyne, Simi Valley, CA (US); Leo E. Manzer, Wilmington, DE (US); Mark L. Jarand, Newbury Park, CA (US); Haijun Wan, Camarillo, CA (US); Rajashekharam Malyala, Camarillo, CA (US)

(73) Assignee: Cool Planet Energy Systems, Inc., Greenwood Village, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/792,486

(22) Filed: Oct. 24, 2017

(65) Prior Publication Data

US 2018/0118631 A1 May 3, 2018

Related U.S. Application Data

(63) Continuation of application No. 15/156,256, filed on May 16, 2016, now Pat. No. 9,809,502, which is a (Continued)

(51) Int. Cl.
| | | |
|---|---|---|
| C09K 17/04 | (2006.01) | |
| C05G 3/04 | (2006.01) | |

(Continued)

(52) U.S. Cl.
CPC ............. *C05D 9/00* (2013.01); *C05F 11/00* (2013.01); *C05F 11/02* (2013.01); *C05F 11/08* (2013.01);
(Continued)

(58) Field of Classification Search
CPC ...................................... C09K 17/04
See application file for complete search history.

(56) References Cited

U.S. PATENT DOCUMENTS

| | | |
|---|---|---|
| 1,369,428 A | 2/1921 | Hawley |
| 4,153,514 A | 5/1979 | Garrett et al. |

(Continued)

FOREIGN PATENT DOCUMENTS

| | | |
|---|---|---|
| CN | 1997590 A | 7/2007 |
| CN | 103053244 A | 4/2013 |

(Continued)

OTHER PUBLICATIONS

Gray, et al.; Water update in biochars: The roles of porosity and hydrophobicity; Biomass and Bioenergy; vol. 6, No. 1, pp. 196-205; Jan. 23, 2014.

(Continued)

*Primary Examiner* — Wayne A Langel
(74) *Attorney, Agent, or Firm* — Avyno Law P.C.

(57) ABSTRACT

Biochar is provided that is treated to have certain chemical and physical properties found to have the highest impact on plant growth and/or soil health. In particular, the following physical and/or chemical properties, among others, of a biochar have been identified as critical properties to control for in the selection of biomass feedstock, pyrolysis conditions, and/or enhancing treatment to increase biochar performance: (i) bulk density (ii) impregnation capacity; (iii) particle size distribution; (iv) solid particle density; (v) surface area; (vi) porosity; (vii) total porosity; (viii) ratio of (Continued)

macroporosity to total porosity (ix) content of residual organic compounds; (x) content of volatile organic compounds; (xii) ash content; (xiii) water holding capacity; (xiv) water retention capabilities; (xv) levels of dioxins and other potentially hazardous byproducts of pyrolysis; and (xvi) pH. Treatment can modify and preferably increase hydrophilicity/decrease hydrophobicity, remove dioxins from the raw biochar, modify electrical conductivity and/or surface charge, modify cation exchange capacity and modify anion exchange capacity, among other things.

25 Claims, 32 Drawing Sheets

Related U.S. Application Data continuation-in-part of application No. 14/873,053, filed on Oct. 1, 2015, application No. 15/792,486, which is a continuation-in-part of application No. 14/385,986, filed as application No. PCT/US2012/039862 on May 29, 2012, now Pat. No. 9,493,380, which is a continuation-in-part of application No. 13/154,213, filed on Jun. 6, 2011, now Pat. No. 8,317,891, application No. 15/792,486, which is a continuation-in-part of application No. 14/036,480, filed on Sep. 25, 2013, now Pat. No. 9,359,268, which is a continuation of application No. 13/189,709, filed on Jul. 25, 2011, now Pat. No. 8,568,493.

(60) Provisional application No. 62/162,219, filed on May 15, 2015, provisional application No. 62/058,445, filed on Oct. 1, 2014, provisional application No. 62/058,472, filed on Oct. 1, 2014.

(51) Int. Cl.
*C05D 9/00* (2006.01)
*C05F 11/08* (2006.01)
*C05G 3/00* (2006.01)
*C09K 17/02* (2006.01)
*C05F 11/00* (2006.01)
*C05F 11/02* (2006.01)
*C10B 53/02* (2006.01)
*C10B 57/02* (2006.01)
*C05D 9/02* (2006.01)

(52) U.S. Cl.
CPC ............. *C05G 3/00* (2013.01); *C05G 3/04* (2013.01); *C09K 17/02* (2013.01); *C09K 17/04* (2013.01); *C10B 53/02* (2013.01); *C10B 57/02* (2013.01); *C05D 9/02* (2013.01); *Y02E 50/14* (2013.01); *Y02E 50/32* (2013.01); *Y10S 71/903* (2013.01)

(56) References Cited

U.S. PATENT DOCUMENTS

| | | | |
|---|---|---|---|
| 4,268,275 A | 5/1981 | Chittick | |
| 4,383,391 A | 5/1983 | Thomas et al. | |
| 4,421,524 A | 12/1983 | Chittick | |
| 4,487,958 A | 12/1984 | Ream et al. | |
| 4,495,165 A | 1/1985 | Gurza | |
| 4,497,637 A | 2/1985 | Purdy et al. | |
| 4,501,644 A | 2/1985 | Thomas | |
| 4,530,702 A | 7/1985 | Fetters et al. | |
| 4,618,735 A | 10/1986 | Bridle et al. | |
| 4,861,351 A | 8/1989 | Nicholas et al. | |
| 4,992,480 A | 2/1991 | Mahajan et al. | |
| 5,015,423 A | 5/1991 | Eguchi et al. | |
| 5,032,618 A | 7/1991 | Marchionna et al. | |
| 5,087,786 A | 2/1992 | Nubel et al. | |
| 5,204,102 A | 4/1993 | Coles et al. | |
| 5,221,290 A | 6/1993 | Dell | |
| 5,462,908 A | 10/1995 | Liang et al. | |
| 5,504,259 A | 4/1996 | Diebold et al. | |
| 5,508,060 A | 4/1996 | Perman et al. | |
| 5,756,194 A | 5/1998 | Shogren et al. | |
| 5,820,640 A | 10/1998 | Ikura et al. | |
| 5,857,807 A | 1/1999 | Longo, Sr. | |
| 5,863,467 A | 1/1999 | Mariner et al. | |
| 6,133,328 A | 10/2000 | Lightner | |
| 6,227,473 B1 | 5/2001 | Arnold | |
| 6,228,806 B1 | 5/2001 | Mehta | |
| 6,339,031 B1 | 1/2002 | Tan | |
| 6,548,026 B1 | 4/2003 | Dales et al. | |
| 6,747,067 B2 | 6/2004 | Melnichuk et al. | |
| 6,811,703 B2 | 11/2004 | Elliott | |
| 6,841,085 B2 | 1/2005 | Werpy et al. | |
| 6,923,838 B2 | 8/2005 | Maubert et al. | |
| 6,994,827 B2 | 2/2006 | Safir et al. | |
| 7,033,972 B2 | 4/2006 | Shikada et al. | |
| 7,226,566 B2 | 6/2007 | Beierle | |
| 7,282,189 B2 | 10/2007 | Zauderer | |
| 7,458,999 B2 | 12/2008 | Schenck | |
| 7,846,979 B2 | 12/2010 | Rojey et al. | |
| 7,888,540 B2 | 2/2011 | Deluga et al. | |
| 7,947,155 B1 | 5/2011 | Green et al. | |
| 8,173,044 B1 | 5/2012 | Cheiky et al. | |
| 8,197,573 B2 | 6/2012 | Scharf | |
| 8,236,085 B1 | 8/2012 | Cheiky et al. | |
| 8,317,891 B1 | 11/2012 | Cheiky et al. | |
| 8,317,892 B1 | 11/2012 | Cheiky et al. | |
| 8,318,997 B2 | 11/2012 | McAlister | |
| 8,361,186 B1* | 1/2013 | Shearer | C05F 5/00 71/32 |
| 8,430,937 B2 | 4/2013 | Cheiky et al. | |
| 8,431,757 B2 | 4/2013 | Cheiky et al. | |
| 8,568,493 B2* | 10/2013 | Cheiky | C10J 3/62 44/628 |
| 8,747,797 B2 | 6/2014 | Shearer et al. | |
| 9,260,666 B2 | 2/2016 | Aelion et al. | |
| 9,478,324 B1 | 10/2016 | Favetta et al. | |
| 9,493,379 B2 | 11/2016 | Cheiky et al. | |
| 9,809,502 B2* | 11/2017 | Bontchev | C05D 9/00 |
| 2002/0012725 A1 | 1/2002 | Carlson | |
| 2003/0119552 A1 | 6/2003 | Laumen et al. | |
| 2004/0111968 A1 | 6/2004 | Day et al. | |
| 2004/0128909 A1 | 7/2004 | Smiley | |
| 2006/0225345 A1 | 10/2006 | Westrate | |
| 2007/0123420 A1 | 5/2007 | Hayashi et al. | |
| 2007/0287068 A1 | 12/2007 | Shimizu et al. | |
| 2008/0003166 A1 | 1/2008 | Maletin et al. | |
| 2008/0006519 A1 | 1/2008 | Badger | |
| 2008/0016769 A1 | 1/2008 | Pearson | |
| 2008/0047313 A1 | 2/2008 | Johnson et al. | |
| 2008/0093209 A1 | 4/2008 | Noto | |
| 2008/0216391 A1 | 9/2008 | Cortright et al. | |
| 2008/0223269 A1 | 9/2008 | Paoluccio | |
| 2008/0300435 A1 | 12/2008 | Cortright et al. | |
| 2008/0317657 A1 | 12/2008 | Hall et al. | |
| 2008/0317907 A1 | 12/2008 | Thomas et al. | |
| 2009/0007484 A1 | 1/2009 | Smith | |
| 2009/0081292 A1 | 3/2009 | Otomo et al. | |
| 2009/0126433 A1 | 5/2009 | Piskorz et al. | |
| 2009/0139139 A1 | 6/2009 | Tilman et al. | |
| 2009/0151251 A1 | 6/2009 | Manzer et al. | |
| 2009/0183430 A1 | 7/2009 | Schubert et al. | |
| 2009/0196816 A1 | 8/2009 | Yamamoto et al. | |
| 2009/0217575 A1 | 9/2009 | Raman et al. | |
| 2009/0217584 A1 | 9/2009 | Raman et al. | |
| 2009/0253947 A1 | 10/2009 | Brandvold et al. | |
| 2009/0308787 A1 | 12/2009 | O'Connor et al. | |
| 2010/0040510 A1 | 2/2010 | Randhava et al. | |
| 2010/0162780 A1 | 7/2010 | Scharf | |
| 2010/0180805 A1 | 7/2010 | Cheiky | |
| 2010/0218417 A1 | 9/2010 | Bauldreay et al. | |
| 2010/0223839 A1 | 9/2010 | Garcia-Perez et al. | |
| 2010/0236309 A1 | 9/2010 | Celia | |

(56) References Cited

U.S. PATENT DOCUMENTS

| | | |
|---|---|---|
| 2010/0236987 A1 | 9/2010 | Kreis |
| 2010/0257775 A1 | 10/2010 | Cheiky |
| 2010/0270505 A1 | 10/2010 | Gallaspy et al. |
| 2010/0300866 A1 | 12/2010 | van Aardt et al. |
| 2010/0310447 A1 | 12/2010 | Yaniv et al. |
| 2010/0311157 A1 | 12/2010 | Van Alstyne et al. |
| 2011/0003693 A1 | 1/2011 | Spittle |
| 2011/0023566 A1 | 2/2011 | Lodwig et al. |
| 2011/0081336 A1 | 4/2011 | Medoff |
| 2011/0092726 A1 | 4/2011 | Clarke |
| 2011/0100359 A1 | 5/2011 | North |
| 2011/0172092 A1 | 7/2011 | Lee et al. |
| 2011/0177466 A1 | 7/2011 | Cheiky |
| 2011/0209386 A1 | 9/2011 | Cheiky et al. |
| 2011/0212004 A1 | 9/2011 | Cheiky et al. |
| 2011/0258912 A1 | 10/2011 | O'connor et al. |
| 2012/0103040 A1 | 5/2012 | Wolf et al. |
| 2012/0125064 A1 | 5/2012 | Joseph et al. |
| 2012/0208254 A1 | 8/2012 | Smith et al. |
| 2012/0220454 A1 | 8/2012 | Chen et al. |
| 2012/0237994 A1 | 9/2012 | Das et al. |
| 2012/0283493 A1 | 11/2012 | Olson et al. |
| 2012/0286209 A1 | 11/2012 | Cheiky et al. |
| 2012/0304718 A1 | 12/2012 | Cheiky et al. |
| 2012/0304719 A1 | 12/2012 | Cheiky et al. |
| 2013/0025188 A1 | 1/2013 | Cheiky et al. |
| 2013/0025190 A1 | 1/2013 | Cheiky et al. |
| 2013/0123103 A1 | 5/2013 | Anderson et al. |
| 2013/0213101 A1 | 8/2013 | Shearer et al. |
| 2014/0016709 A1 | 1/2014 | Ko et al. |
| 2014/0024528 A1 | 1/2014 | Smith et al. |
| 2014/0037536 A1 | 2/2014 | Reimerink-Schats et al. |
| 2014/0161709 A1 | 6/2014 | Karthikeyan |
| 2014/0177136 A1 | 6/2014 | Kim et al. |
| 2014/0295161 A1 | 10/2014 | MacLachlan et al. |
| 2014/0345341 A1 | 11/2014 | Fiato et al. |
| 2014/0345343 A1 | 11/2014 | Wilson et al. |
| 2014/0349847 A1 | 11/2014 | Schrader |
| 2014/0352378 A1 | 12/2014 | Shearer et al. |
| 2015/0101372 A1 | 4/2015 | Cheiky et al. |
| 2015/0128672 A1 | 5/2015 | Shearer et al. |
| 2015/0155549 A1 | 6/2015 | Moganty et al. |
| 2015/0157661 A1 | 6/2015 | Eddy et al. |
| 2015/0361369 A1 | 12/2015 | Tait et al. |
| 2016/0023959 A1 | 1/2016 | Bontchev et al. |
| 2016/0102024 A1 | 4/2016 | Schrader et al. |
| 2016/0362607 A1 | 12/2016 | Weaver et al. |
| 2016/0368831 A1 | 12/2016 | Bontchev et al. |
| 2017/0008769 A1 | 1/2017 | Otter et al. |

FOREIGN PATENT DOCUMENTS

| | | |
|---|---|---|
| EP | 01140811 A2 | 5/1985 |
| GB | 2479469 A | 10/2011 |
| KR | 100819505 B1 | 4/2008 |
| WO | 8204223 A1 | 12/1982 |
| WO | 8909809 A1 | 10/1989 |
| WO | 2004037747 A2 | 5/2004 |
| WO | 2005030641 A1 | 4/2005 |
| WO | 2008058231 A2 | 5/2008 |
| WO | 2009004652 A1 | 1/2009 |
| WO | 2010084230 A1 | 7/2010 |
| WO | 2010129988 A1 | 11/2010 |
| WO | 2011006717 A2 | 1/2011 |
| WO | 2011014916 A1 | 2/2011 |
| WO | 2011097183 A2 | 8/2011 |
| WO | 2011143380 A2 | 11/2011 |
| WO | 2011143718 A1 | 11/2011 |
| WO | 2014060508 A1 | 4/2014 |
| WO | 2014091279 A1 | 6/2014 |
| WO | 2014146205 A1 | 9/2014 |
| WO | 2015055729 A1 | 4/2015 |
| WO | 2016054431 A1 | 4/2016 |
| WO | 2016187161 A1 | 11/2016 |

OTHER PUBLICATIONS

Downie: Biochar Production and Use: Environmental Risks and Rewards; PhD Thesis; The University of New South Wales; Sydney Australia (2011); p. 1-16; p. 155-168.

Ahmad, et al.; Biochar as a sorbent for contaminant management in soil and water: A review; Chemosphere; vol. 99, pp. 19-33; Nov. 27, 2013.

Berek, et al., "Improving Soil Productivity with Biochar," ICGAI, Yogyakarta, Indonesia, 23 pgs. (Nov. 11-14, 2013).

Beesley, et al., "A review of Biochars? Potential Role in the Remediation, Revegetation and Restoration of Contaminated Soils," Environmetnal Pollution 159, pp. 3269-3282 (Jul. 23, 2011).

Biliaderis, et al., "Functional Food Carbohydrates," CRC Press 2006, Ch. 16, pp. 517-518.

Bucheli, et al., "Polycyclic Aromatic Hydrocarbons and Polychlorinated Aromatic Compounds in Biochar," Biochar for Environmental Management, Ch. 21, pp. 595-622 (Jan. 2015).

Buerschaper, R., "Thermal & Electrical Conductivity of Graphite & Carbon at Low Temperatures," Jour. of App. Physics, pp. 452-454 (1944).

Cheng, et al., "Stability of Black Carbon in Soils Across a Climatic Gradient," Jour. of Geophysical Research Biogeosciences, vol. 113, G02027, pp. 1-10 (2008).

Chew, T.L. and Bhatia, S., "Catalytic Processes Towards the Production of Biofuels in a Palm Oil and Oil Palm Biomass-based Biorefinery," Bioresource Tech., vol. 99, pp. 7911-8922 (2008).

Demirbas, A., "Effects of Temperature & Particle Size on Bio-Char Yield from Pyrolysis of Agricultural Residues," J. Anal. Pyrolysis, vol. 72, pp. 243-248 (2004).

Elliott, D.C. and Neuenschwander, G.G., "Liquid Fuels by Low-Severity Hydrotreating of Biocrude," Dev. in Thermochemical Biomass Conversion, vol. 1, pp. 611-621 (1996).

Extended European Search Report issued by the European Patent Office for European Patent Application No. 12797129.9 dated Mar. 6, 2015 (7 pgs.).

Extended European Search Report issued by the European Patent Office for European Patent Application No. 12817137.8 dated Jul. 13, 2015 (8 pgs.).

Faludi, J., "World Changing Change Your Thinking a Carbon-Negative Fuel," Oct. 16, 2007; www.worldchanging.com (9 pgs.).

Gehrer, r. and Hayek, K., "A Fully Programmable System for the Study of Catalytic Gas Reactions," J. Physc. E: Sci. Instrum., vol. 18, pp. 836-838 (1985).

Greenfacts, "Facts on Health and the Environment," Dioxins, Apr. 13, 2017, 3 pp.; retrieved from https://www.greenfacts.org/en/d on Aug. 15, 2004.

Hadjittofi, et al., "Activated Biochar Derived from Cactus Fibres—Preparation, Characterization and Application on CU(II) Removal from Aqueous Solutions," Bioresource Technology, vol. 159, pp. 460-464 (May 2014).

Hua, et al., "Impacts Upon Soil Quality and Plant Growth of Bamboo Charcoal Addition to Composted Sludge," Environmental Technology, vol. 33, No. 1, pp. 61-68 (Jan. 18, 2012).

Innovation Fluides Supercritiques, Explore, Use, Make the Most of Supercritical Fluids, Nov. 27, 2015. Online, retrieved from the Internet on Mar. 6, 2017; <http://web/archive.org/web/20151127045828/ http://www.supercriticalfluid.org/supercritical-fluids.146.0>html; 2 pp.

Jindo, et al., "Biochar Influences the Microbial Community Structure During Manure Composting with Agricultural Wastes," Science of the Total Environment, vol. 416, pp. 476-481 (Feb. 2012).

Karmakar, et al., "Plant Defence Activators Inducing Systematic Resistance in Zingiber Officinale Rosc. Against Pythium Aphanidermatum (Edson) Fitz.," Indian Journal of Biotechnology, vol. 2, pp. 591-595 (2003).

Kim, et al., "Characteristics of Crosslinked Potato Starch & Starch-Filled Linear Low-Density Polyethylene Films," Carbohydrate Polymers, vol. 50, pp. 331-337 (2002).

Kolton, et al., "Impact of Biochar Application to Soil on the R oot-Associated Bacterial Community Structure of Fully Developed Greenhouse Pepper Plants," Appl. Env. Micro., pp. 4924-4930, Abstract (Jul. 2011).

(56) References Cited

OTHER PUBLICATIONS

Laird, D., "The Charcoal Vision: A Win Win Scenario," Agron, J., vol. 100, No. 1, pp. 178-181 (2008).
Lashari, et al., "Effect of Amendment of Biochar-manure Compost in Conjunction with Pyroligneous Solution on Soil Quality and Wheat Yield of a salt-stressed Cropland from Central China Great Plain," Field Crops Research, vol. 144, pp. 113-118 (Mar. 20, 2013).
Lehmann, J., "Nutrient Avail. & Leaching in an Archaeological Anthrosol & Ferraisol of the Central Amazon Basin: Fertilizer, Manure and Charcoal Amendments," Plant Soil, vol. 249, pp. 343-357 (2003).
Lima, et al., "Physiochemical and Adsorption Properties of Fast-Pyrolysis Bio-Chars and their Steam Activated Counterparts," J.Chem. Tech. Biotechnical, vol. 85, pp. 1515-1521 (2010).
Liu, et al., "An Experimental Study of Rheological Properties and Stability Characteristics of Biochar-Glycerol-Water Slurry Fuels," Fuel Processing Technology, vol. 153, Issue 1, pp. 37-42 (Aug. 5, 2016).
Mathews, J.A., "Carbon-negative Biofuels", Energy Policy, vol. 36, pp. 940-945 (2008).
McHenry, Mark P., "Agricultural Bio-char Production, Renewable Energy Generation and Farm Carbon Sequestration in Western Australia: Certainty, Uncertainty and Risk," Agriculture, Ecosystems and Environments, vol. 129, pp. 1-7 (2009).
Mohan, et al., "Pyrolysis of Wood/Biomass for Bio-Oil: A Critical Review," Energy & Fuels, vol. 20, pp. 848-889 (2006).
Norman, et al.; "Best Management Practices for Reclaiming Surface Mines in Washington and Oregon," Open-File Report 0-92-2, revised ed. Dec. 1997; www.oregongeology.org Feb. 9, 2010 (128 pgs.).
Oh, et al., "Ulitization of Biochar Impregnated with Anaerobically Digested Slurry as Slow-Release Fertilizer," Journal of Plant Nutrition and Soil Science, vol. 177, Issue 1, pp. 97-103 (Feb. 2014).
Omata, et al., "Optimization of Cu Oxide Catalyst for Methanol Synthesis under High C02 Partial Pressure Using Combinatorial Tools," App. Catalyst A: General, vol. 262, pp. 207-214 (2004).
Preston, C.M. and Schmidt, M.W., "Black (Pyrogenic) Carbon; a Synthesis of Current Knowledge & Uncertainties w/ Special Consideration of Boreal Regions," Biogeosciences, vol. 3, pp. 397-420 (2006).
Rosenberg, et al., "More on Commercial Carbon Resistors as Low Pressure Gauges," Intl. Jour of Impat. Eng., vol. 34, pp. 732-742 (2007).
Schmidt, et al., "Biochar and Biochar-compost as Soil Amendments to a Vineyard Soil: Influence on Plant Growth, Nutrient Update, Plant Health and Grape Equality," Agriculture, Ecosystems and Environment, vol. 191, Issue 15, pp. 117-123 (Jun. 2014).
Sharma, R.K. and Bakhshi, N.N., "Catalytic Upgrading of Pyrolysis Oil," Energy & Fuels, vol. 7, pp. 306-314 (1993).
Shivaram, et al., "Flow and Yield Behavior of Ultrafine Mallee Biochar Slurry Fuels: The Effect of Particle Size Distributon and Additives," 10th Japan/China Symposium on Coal and C1 Chemistry, vol. 104, pp. 326-332 (Feb. 2013).
Sorrenti, G. (Doctoral Thesis): "Biochar in Perennial Crops: Nutritional, Agronomical and Environmental Implications," University of Bologna, Abstract, Chs. 4, 5, 7, p. 101 Table 4.2 (Mar. 1, 2015).
Takeishi, K., "Dimethy Ether & Catalyst Development for Production of Syngas," Biofuels, vol. 1(1), pp. 217-226 (2010).
Tryon, E.H.; "Effect of Charcoal on Certain Physical, Chemical, & Biological Properties of Forest Soils," Ecological Monographs, vol. 18, No. 1, pp. 81-115 (Jan. 1948).
Xusheng, et al., "Implications of Production and Agricultural Utilization of Biochar and its International Dynamic," Transactions of the CSAE, vol. 27, No. 2, 7 pgs. (2011) with English Abstract.
Wikipedia; Bacillus Thuringiensis; Dec. 27, 2015; online, retrieved from the Internet on Mar. 6, 2017; <https://en/wikipedia.org/w/index.php?title=bacillus+thuringiensis&oldid=696970111>; 6 pp.
Supplemental European Search Report dated Aug. 17, 2017 for EP 14875314.8.

* cited by examiner

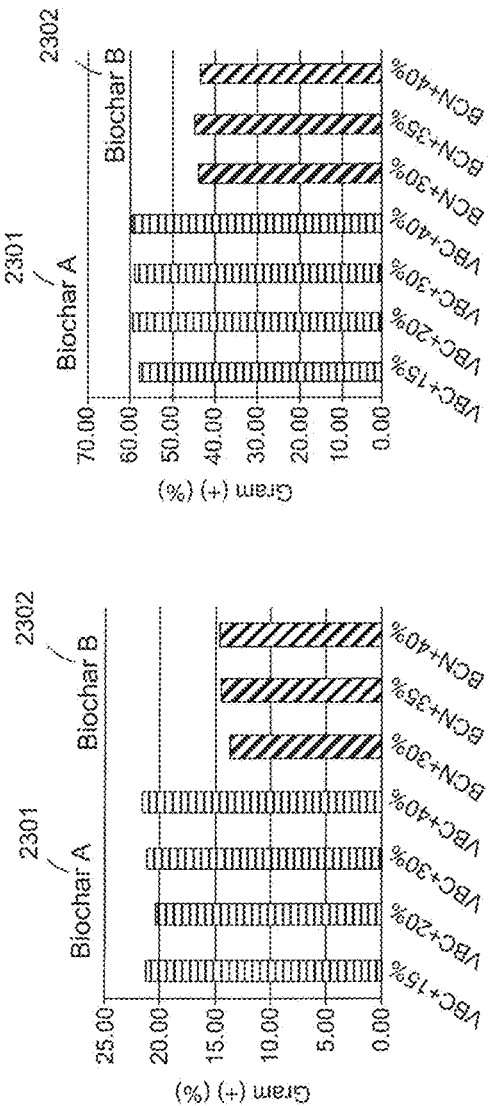
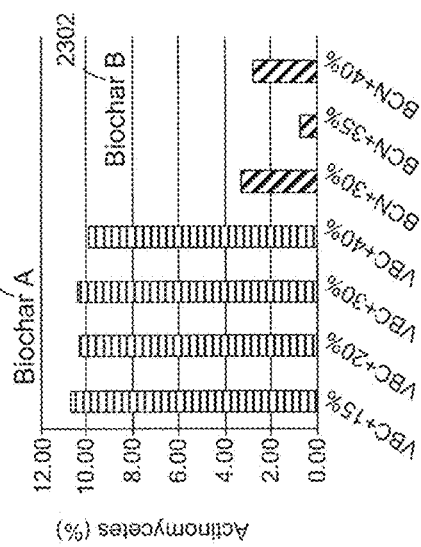
FIG. 23a
FIG. 23b
FIG. 23c

ENHANCED BIOCHAR

RELATED APPLICATIONS

This application is a continuation of and claims priority to U.S. patent application Ser. No. 15/156,256 filed on May 16, 2016 titled Enhanced Biochar, which claims priority to U.S. Provisional Patent Application No. 62/162,219, filed on May 15, 2015, titled Enhanced Biochar; is a continuation-in-part of U.S. patent application Ser. No. 14/873,053 filed on Oct. 1, 2015, titled Biochars and Biochar treatment Processes which claims priority to U.S. Provisional Patent Application No. 62/058,445, filed on Oct. 1, 2014, titled Methods, Materials and Applications for Controlled Porosity and Release Structures and Applications and U.S. Provisional Patent Application No. 62/058,472, filed on Oct. 1, 2014, titled High Additive Retention Biochars, Methods and Applications; is a continuation-in-part of U.S. patent application Ser. No. 14/385,986 filed on May 29, 2012, titled Method for Enhancing Soil Growth Using Bio-Char which is a 371 of PCT/US12/39862 filed on May 29, 2012, which is a continuation-in-part of U.S. patent application Ser. No. 13/154,213 filed on Jun. 6, 2011 (now U.S. Pat. No. 8,317,891); and is a continuation-in-part of U.S. patent application Ser. No. 14/036,480, filed on Sep. 25, 2013, titled Method for Producing Negative Carbon Fuel, which is a continuation of U.S. patent application Ser. No. 13/189,709, filed on Jul. 25, 2011 (now U.S. Pat. No. 8,568,493), all of the above of which are incorporated in their entirety by reference in this application.

BACKGROUND OF THE INVENTION

1. Field of the Invention

The present invention relates to biochar and, in particular, to treated and/or processed biochar having enhanced physical and chemical properties that increase the usefulness, predictability and efficacy of the treated biochar for a variety of applications.

2. Related Art

Biochar has been known for many years as a soil enhancer. Biochar is defined by the International Biochar Initiative ("IBI") as "a solid material obtained from thermochemical conversion of biomass in an oxygen-limited environment. Biochar can be used for a range of applications as an agent for soil improvement, improved resource use efficiency, remediation and/or protection against particular environmental pollution and as an avenue for greenhouse gas (GHG) mitigation. In addition, to be recognized as biochar, the material has to pass a number of material property definitions that relate both to its value (e.g., $H/C_{org}$ ratios relate to the degree of charring and therefore mineralization in soil) and its safety (e.g., heavy metal content)."

Biochar is defined by the American Association of Plant Food Control Officials ("AAPFCO") as "a solid material obtained from thermochemical conversion of biomass in an oxygen-limited environment (pyrolysis) containing at least 60% carbon. Feedstocks may be composed of crop residue, wood or other forest waste, and animal manures. Materials transported in salt water, painted, or treated with preservatives are not permitted. When listing biochar in an ingredient statement, the feedstock shall be designated by prefixing the term biochar with the feedstock from which it was produced; i.e. poultry litter biochar, green waste biochar, papermill biochar, etc. When more than one feedstock is involved, all feedstocks greater than 10% of the total volume are to be listed by decreasing volume."

Biochar is created by the pyrolysis of biomass, which generally involves heating and/or burning of organic matter, in a reduced oxygen environment, at a predetermined rate. Such heating and/or burning is stopped when the matter reaches a charcoal like stage. The resulting biochar consists of various pieces of residual solid material full of crevices, pores and holes that help store water, microorganisms and other nutrients that promote plant growth. For purposes of this application, the resulting pyrolyzed biomass will be referred to as "raw or untreated biochar."

Raw biochar, while known for its soil enhancing characteristics, does not always benefit soil and, depending upon the biomass from which the biochar is produced, could potentially be harmful to the soil, making it unsuitable for various types of crops or other productive uses. In particular, biochar can be detrimental, or even toxic, to 1) soil microbes involved in nutrient transport to the plant; 2) plants and 3) humans. Raw biochars derived from different biomass will have different physical and chemical properties and will behave quite differently. For example, raw biochar having pH levels too high, containing too much ash, too much of other inorganic materials which can cause toxicity at elevated levels, or containing toxins or heavy metal content too high can be harmful and/or have minimal benefit to the soil and the plant life it supports. Raw biochar can also contain unacceptable levels of residual organic compounds such as acids, esters, ethers, ketones, alcohols, sugars, phenyls, alkanes, alkenes, phenols, polychlorinated biphenyls or poly or mono aromatic hydrocarbons which are either toxic or not beneficial to plant or animal life.

While some attention has been focused on the use of raw biochar in conjunction with controlling and regulating the growth of plants and vegetation, e.g., crops, the commercial and widespread adoption of biochar as a soil amendment has not occurred. There are several reasons for these failures. As described above, biochar may be derived from varied and different sources. As a result, these materials have very inconsistent and unpredictable properties. These inconsistencies and lack of predictability make their use difficult and in many cases problematic. Jeffery et al. in *Agriculture, Ecosystems, and Environment* (2011) ("Jeffery") compiled the results from several biochar field trials from around the globe. The trials show at best a modest improvement with biochar applications and the application rates required to achieve these modest results is significant. (See Jeffery, at page 175 and FIG. 1). Even more recently, Spokas et al. published *Biochar: A Synthesis of Its Agronomic Impact beyond Carbon Sequestration*, in the Journal of Environmental Quality (July 2012), which demonstrated the how untreated biochar may yield vastly different economic and agronomic results when added to soil, from strongly positive to strongly negative. See, also, Buss et al., *Inherent organic compounds in biochar—Their content, composition and potential toxic effects*, Journal of Environmental Management 156 (2015).

In Lehmann, et al, *Biochar for Environmental Management* (2006) ("Lehmann") a pioneer researcher, Lehmann, is quoted about biochar that " . . . variability is high and it is not yet clear under what soil and climatic conditions high or low yields can be expected." (Lehmann, Chp. 12, at page 207) It is believed that these inconsistencies and lackluster outcomes are common among biochar work. Since most cannot produce biochar with predictable properties and outcomes, the use of these materials, e.g., biochar, can have limited, sporadic or little to no beneficial effect. In certain cases, the use may be problematic and detrimental, e.g., lower crop yield, and in some situations, increased mortality rate and/or death of the crops.

Currently, biochar has mostly been a scientific curiosity, not found wide spread use, not found large scale commercial application, and has been relegated to small niche applications. Prior to the present inventions, biochar having predictable, controllable, and beneficial results have not been obtained, thereby prohibiting large scale applications. In general, the art has focused on the failings, and problems, of biochars by attempting to better select or sort the starting material or to refine the pyrolysis or other processes used to make the untreated biochar, without identifying, controlling, or enhancing the properties of a biochar that make it effective. Typically, these attempts were done with the hope that increased process control, material selection and refinements would overcome the unpredictable nature, inconsistencies, and harmful effects found with existing biochars. It is believed that these attempts have been to a lesser or greater extent failures. A need remains for producing biochars that can be used in large scale applications and that have certain generally sustainable, controllable and/or particular physical and chemical properties known to have the highest positive impact on soils. This need is satisfied by the present invention.

SUMMARY

The present invention relates to biochar that is treated or processed to have certain chemical and physical properties found to have the highest impact on plant growth and/or soil health. For purposes of this application, when the biochar is referred to as "treated" or undergoes "treatment," it shall mean raw biochar that has undergone additional physical and/or chemical processing.

In particular, the following physical and/or chemical properties, among others, of a biochar have been identified as critical properties to control for in the selection of biomass feedstock, pyrolysis conditions, and/or enhancing treatment to increase biochar performance: (i) bulk density (ii) impregnation capacity; (iii) particle size distribution; (iv) solid particle density; (v) surface area; (vi) porosity; (vii) total porosity; (viii) ratio of macroporosity to total porosity (ix) content of residual organic compounds; (x) content of volatile organic compounds; (xii) ash content; (xiii) water holding capacity; (xiv) water retention capabilities; (xv) levels of dioxins and other potentially hazardous byproducts of pyrolysis; and (xvi) pH. Treatment can also modify and preferably increase hydrophilicity/decrease hydrophobicity, remove dioxins from the raw biochar, modify electrical conductivity and/or surface charge, modify cation exchange capacity and modify anion exchange capacity, among other things.

For purposes of this application, these properties will be known as "performance properties." The list above of properties is not exhaustive and shall include any property of the biochar that enhances performance of treated biochar over raw biochar for a specified purpose. Those skilled in the art will recognize the certain performance properties may be more desirable than others for different applications, including, but not limited to soil amendments. Further, treatment of raw biochar may be tailored such that certain of these performance properties are targeted to be present in the resulting treated biochar. The treatment process selected and utilized for treating the raw biochar may also be tailored to allow certain of these performance properties to be sustained for certain periods of time after treatment to boost long-term performance of the treated biochar.

The raw biochar of the present invention is obtained from the pyrolysis of biomass. The resulting biochar is then treated in a manner that causes the infusion and/or effusion of liquids into and out of the biochar pores or infiltration and/or exfiltration of liquids into and out of the biochar pores, which process may be caused by the rapid, forced or rapid and forced infusion and/or effusion of liquids or gasses into and out of the biochar pores. While those skilled in the art may recognize other methods for treating the biochar that causes the rapid, forced infusion and effusion of liquids into and out of the biochar pores, one such treatment process that can be used is a process that changes the pressure differential surrounding the biochar, such as vacuum impregnation, optionally following additional vacuum extraction and/or centrifuge extraction. An additional relevant technique is treatment with a solution containing either organic or inorganic surfactant or detergent. The solution to which the surfactant or detergent is added may optionally be heated or may be ambient temperature or less. The combination of pressure changes or vacuum treatment with one or more surfactant or detergent treatments either prior to, simultaneous with, or following vacuum treatment is also a possible treatment method. Optionally, treatment may include subjecting the biochar to temperatures during vacuum treatment from ambient to about 250° C. Since research associated with the present invention has identified what physical and chemical properties have the highest impact on plant growth and/or soil heath, the treatment process can be modified to treat different forms of raw biochar to achieve treated biochar properties known to enhance soil health and plant growth and yield. For example, if the pH of the biochar needs to be adjusted to enhance the raw biochar performance properties, the treatment may be the impregnation of an acidic solution into the pores of the biochar or similarly removal of basic or alkaline compounds from the pores or surface of the raw biochar. This treatment of impregnation or infiltration, impregnation or infiltration with additional additives to assist the process, or both, followed optionally by extraction of the infiltrate has further been proven to sustain the pH levels of the treated biochar for much longer periods than biochar that is simply immersed in an acid solution or washed with water or some other solvent.

By way of another example, if the water holding capacity needs to be adjusted, then gasses, liquids, solids, and semi-solids, to include foreign matter such as residual tars, ash or volatile organic compounds can be removed from the surface, pores, or inter particle spaces of the biochar using vacuum, surfactant, ultrasound, chemical processing, or other techniques to remove or replace the non-beneficial substances, leaving a biochar that is capable of holding and retaining more water and nutrient containing substances than before the treatment. The above describes a few examples of treatment that result in treated biochar having desired performance properties identified to enhance soil health and plant life.

Other devices, apparatus, systems, methods, features and advantages of the invention are or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The invention may be better understood by referring to the following figures. The components in the figures are not necessarily to scale, emphasis instead being placed upon illustrating the principles of the invention. In the figures, like reference numerals designate corresponding parts throughout the different views.

FIGS. 23a, 23b, 23c are charts comparing different examples of biochars.

DETAILED DESCRIPTION

Figure 1:
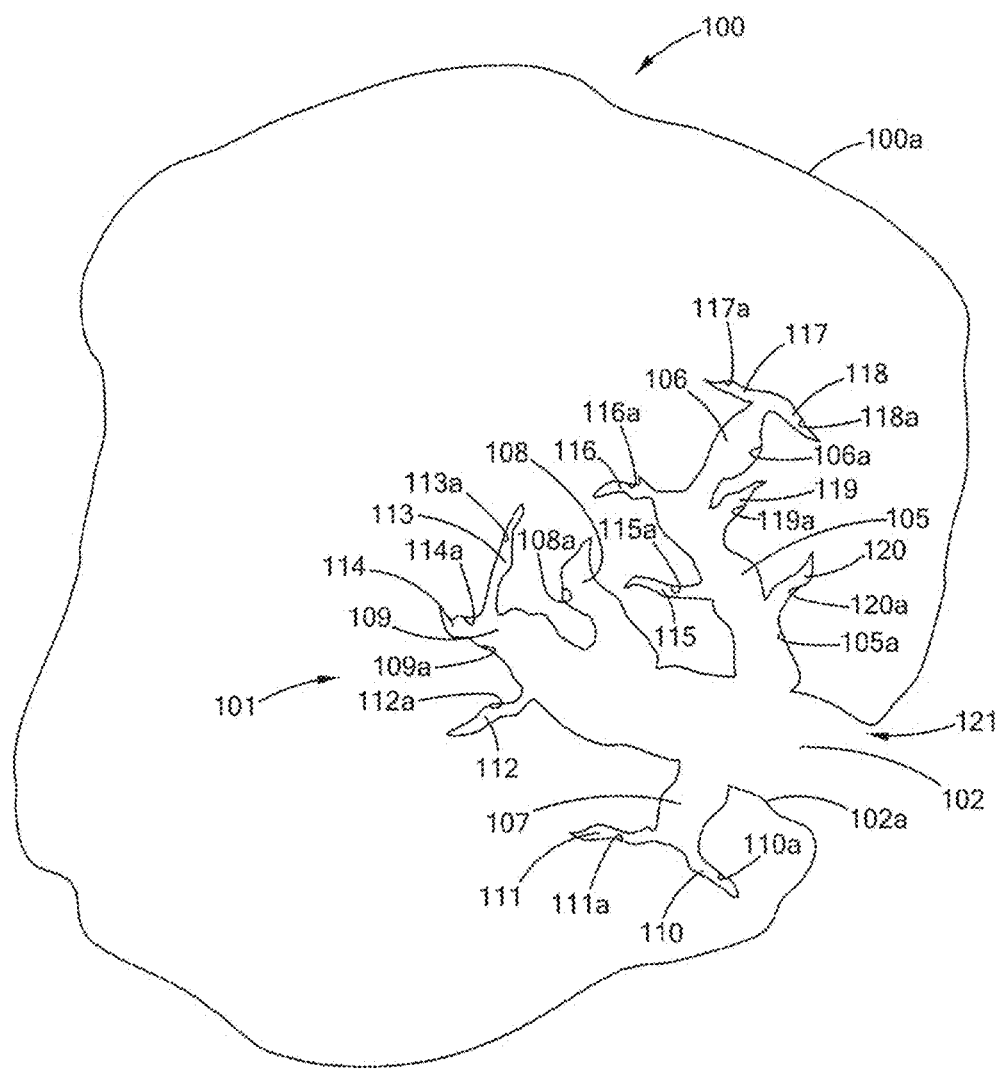
FIG. 1 illustrates a cross-section of one example of a raw biochar particle.

Whether biochar is harmful or helpful to soil health, plant growth and yield and/or useful for other applications, including but not limited to animal application, depends largely on the chemical and physical properties of the biochar. In general, the present invention relates to biochar that is treated to have certain chemical and physical properties found to have the highest impact on plant growth and/or soil health. These properties or characteristics can be further enhanced and sustained for longer periods of time with the utilization of certain treatment processes and through the biomass processing and/or raw biochar selection. As explained further below, the resulting properties of the treated biochar can be tailored through biochar production, selection and treatment to achieve treated biochar having chemical and physical properties useful for specific applications.

Testing was performed on a variety of types of raw and treated biochar. The testing involved full lab scale evaluation of the properties of raw biochar produced from over 40 biomass sources. Testing studied the properties possessed by the different raw biochar in light of the source biomass and the pyrolysis process used to produce the biochar. Batches of the raw biochar were treated utilizing different treatment methods and the toxicity of and properties of the raw and treated biochar were evaluated. In particular, elemental, polyaromatic hydrocarbon, pathogen, and phytotoxicity analyses were performed. The physical and chemical properties of the raw and treated biochar were compared, soil tested for performance and the changes in pH over time were studied.

Testing revealed that the following properties (among others) impact the performance of raw or treated biochar:
Bulk density
Impregnation Capacity
Particle Size & Particle Size Distribution Surface Area
Total porosity
Ratio of Macroporosity to Total Porosity
pH
Water Holding Capacity (WHC)
Residual Organic Compounds (ROCs)
Volatile Organic Compounds (VOCs)
Ash Content
Water Retention Capacity
Dioxin Content
Hydrophobicity
Electrical Conductivity
Cation and Anion Exchange Capacity (CEC and AEC)

Testing further demonstrated that many of the above properties can be altered in biochar, when compared to its raw state, to be more beneficial or suitable for specific applications through treating the raw biochar with processes designed to achieve the desired proven high impact properties.

For purposes of this application, the term "biochar" shall be given its broadest possible meaning and shall include any solid materials obtained from the pyrolysis, torrefaction, gasification or any other thermal and/or chemical conversion of a biomass, where the biochar contains at least 55% carbon based upon weight. Pyrolysis is generally defined as a thermochemical decomposition of organic material at elevated temperatures in the absence of, or with reduced levels of oxygen.

For purposes of this application, biochar may include, but not be limited to, BMF char disclosed and taught by U.S. Pat. No. 8,317,891, which is incorporated into this application by reference, and those materials falling within the IBI and AAPFCO definition of biochar. When the biochar is referred to as "treated" or undergoes "treatment," it shall mean raw, pyrolyzed biochar that has undergone additional physical, biological, and/or chemical processing.

As used herein, unless specified otherwise, the terms "carbonaceous", "carbon based", "carbon containing", and similar such terms are to be given their broadest possible meaning, and would include materials containing carbon in various states, crystallinities, forms and compounds.

As used herein, unless stated otherwise, room temperature is 25° C. And, standard temperature and pressure is 25° C. and 1 atmosphere. Unless stated otherwise, generally, the term "about" is meant to encompass a variance or range of ±10%, the experimental or instrument error associated with obtaining the stated value, and preferably the larger of these.

A. Biochars

Typically, biochars include porous carbonaceous materials, such as charcoal, that are used as soil amendments or other suitable applications. Biochar most commonly is created by pyrolysis of a biomass. In addition to the benefits to plant growth, yield and quality, etc.; biochar provides the benefit of reducing carbon dioxide ($CO_2$) in the atmosphere by serving as a method of carbon sequestration. Thus, biochar has the potential to help mitigate climate change, via carbon sequestration. However, to accomplish this important, yet ancillary benefit, to any meaningful extent, the use of biochar in agricultural applications must become widely accepted, e.g., ubiquitous. Unfortunately, because of the prior failings in the biochar arts, this has not occurred. It is believed that with the solutions of the present invention may this level of use of biochar be achieved; and more importantly, yet heretofore unobtainable, realize the benefit of significant carbon sequestration.

In general, one advantage of putting biochar in soil includes long term carbon sequestration. It is theorized that as worldwide carbon dioxide emissions continue to mount, benefits may be obtained by, controlling, mitigating and reducing the amount of carbon dioxide in the atmosphere and the oceans. It is further theorized that increased carbon dioxide emissions are associated with the increasing industrial development of developing nations, and are also associated with the increase in the world's population. In addition to requiring more energy, the increasing world population will require more food. Thus, rising carbon dioxide emissions can be viewed as linked to the increasing use of natural resources by an ever increasing global population. As some suggest, this larger population brings with it further demands on food production requirements. Biochar uniquely addresses both of these issues by providing an effective carbon sink, e.g., carbon sequestration agent, as well as, an agent for improving and increasing agricultural output. In particular, biochar is unique in its ability to increase agricultural production, without increasing carbon dioxide emission, and preferably reducing the amount of carbon dioxide in the atmosphere. However, as discussed above, this unique ability of biochar has not been realized, or seen, because of the inherent problems and failings of prior biochars including, for example, high pH, phytotoxicity due to high metals content and/or residual organics, and dramatic product inconsistencies.

Biochar can be made from basically any source of carbon, for example, from hydrocarbons (e.g., petroleum based materials, coal, lignite, peat) and from a biomass (e.g., woods, hardwoods, softwoods, waste paper, coconut shell, manure, chaff, food waste, etc.). Combinations and variations of these starting materials, and various and different members of each group of starting materials can be, and are, used. Thus, the large number of vastly different starting materials leads to biochars having different properties.

Many different pyrolysis or carbonization processes can be, and are used to create biochars. In general, these processes involve heating the starting material under positive pressure, reduced pressure, vacuum, inert atmosphere, or flowing inert atmosphere, through one or more heating cycles where the temperature of the material is generally brought above about 400° C., and can range from about 300° C. to about 900° C. The percentage of residual carbon formed and several other initial properties are strong functions of the temperature and time history of the heating cycles. In general, the faster the heating rate and the higher the final temperature the lower the char yield. Conversely, in general, the slower the heating rate or the lower the final temperature the greater the char yield. The higher final temperatures also lead to modifying the char properties by changing the inorganic mineral matter compositions, which in turn, modify the char properties. Ramp, or heating rates, hold times, cooling profiles, pressures, flow rates, and type of atmosphere can all be controlled, and typically are different from one biochar supplier to the next. These differences potentially lead to a biochar having different properties, further framing the substantial nature of one of the problems that the present inventions address and solve. Generally, in carbonization most of the non-carbon elements, hydrogen and oxygen are first removed in gaseous form by the pyrolytic decomposition of the starting materials, e.g., the biomass. The free carbon atoms group or arrange into crystallographic formations known as elementary graphite crystallites. Typically, at this point the mutual arrangement of the crystallite is irregular, so that free interstices exist between them. Thus, pyrolysis involves thermal decomposition of carbonaceous material, e.g., the biomass, eliminating non-carbon species, and producing a fixed carbon structure.

As noted above, raw or untreated biochar is generally produced by subjecting biomass to either a uniform or varying pyrolysis temperature (e.g., 300° C. to 550° C. to 750° C. or more) for a prescribed period of time in a reduced oxygen environment. This process may either occur quickly, with high reactor temperature and short residence times, slowly with lower reactor temperatures and longer residence times, or anywhere in between. To achieve better results, the biomass from which the char is obtained may be first stripped of debris, such as bark, leaves and small branches, although this is not necessary. The biomass may further include feedstock to help adjust the pH and particle size distribution in the resulting raw biochar. In some applications, it is desirous to have biomass that is fresh, less than six months old, and with an ash content of less than 3%. Further, by using biochar derived from different biomass, e.g., pine, oak, hickory, birch and coconut shells from different regions, and understanding the starting properties of the raw biochar, the treatment methods can be tailored to ultimately yield a treated biochar with predetermined, predictable physical and chemical properties. Additionally, the biomass may be treated with various organic or inorganic substances prior to pyrolysis to impact the reactivity of the material during pyrolysis and/or to potentially be fixed in place and available for reaction with various substances during the treatment process after pyrolysis. Trace materials, usually in gaseous form, but potentially in other forms, may also be injected during the pyrolysis process with the intention of either modifying the characteristics of the raw biochar produced, or for potential situation on the raw biochar so that those materials, or a descendant material created by thermal or chemical reaction during pyrolysis, may be reacted with other compounds during the treatment process.

In general, biochar particles can have a very wide variety of particle sizes and distributions, usually reflecting the sizes occurring in the input biomass. Additionally, biochar can be ground, sieved, strained, or crushed after pyrolysis to further modify the particle sizes. Typically, for agricultural uses, biochars with consistent, predictable particle sizes are more desirable. By way of example, the biochar particles can have particle sizes as shown or measured in Table 1 below. When referring to a batch having ¼ inch particles, the batch would have particles that will pass through a 3 mesh sieve, but will not pass through (i.e., are caught by or sit atop) a 4 mesh sieve.

TABLE 1

| U.S. Mesh (i.e., mesh) | Inches | Microns (μm) | Millimeters (mm) |
| --- | --- | --- | --- |
| 3 | 0.2650 | 6730 | 6.370 |
| 4 | 0.1870 | 4760 | 4.760 |
| 5 | 0.1570 | 4000 | 4.000 |
| 6 | 0.1320 | 3360 | 3.360 |
| 7 | 0.1110 | 2830 | 2.830 |
| 8 | 0.0937 | 2380 | 2.380 |
| 10 | 0.0787 | 2000 | 2.000 |
| 12 | 0.0661 | 1680 | 1.680 |
| 14 | 0.0555 | 1410 | 1.410 |
| 16 | 0.0469 | 1190 | 1.190 |
| 18 | 0.0394 | 1000 | 1.000 |
| 20 | 0.0331 | 841 | 0.841 |
| 25 | 0.0280 | 707 | 0.707 |
| 30 | 0.0232 | 595 | 0.595 |
| 35 | 0.0197 | 500 | 0.500 |
| 40 | 0.0165 | 400 | 0.400 |

TABLE 1-continued

| U.S. Mesh (i.e., mesh) | Inches | Microns (μm) | Millimeters (mm) |
| --- | --- | --- | --- |
| 45 | 0.0138 | 354 | 0.354 |
| 50 | 0.0117 | 297 | 0.297 |
| 60 | 0.0098 | 250 | 0.250 |
| 70 | 0.0083 | 210 | 0.210 |
| 80 | 0.0070 | 177 | 0.177 |
| 100 | 0.0059 | 149 | 0.149 |
| 120 | 0.0049 | 125 | 0.125 |
| 140 | 0.0041 | 105 | 0.105 |
| 170 | 0.0035 | 88 | 0.088 |
| 200 | 0.0029 | 74 | 0.074 |
| 230 | 0.0024 | 63 | 0.063 |
| 270 | 0.0021 | 53 | 0.053 |
| 325 | 0.0017 | 44 | 0.044 |
| 400 | 0.0015 | 37 | 0.037 |

For most basic agricultural applications, it is desirable to use biochar particles having particle sizes from about ¾ mesh to about 60/70 mesh, about ⅘ mesh to about 20/25 mesh, or about ⅘ mesh to about 30/35 mesh. However, for applications such as seed treatment, or microbial carriers, smaller mesh sizes ranging from 200, to 270, to 325, to 400 mesh or beyond may be desirable. It is understood that the desired mesh size, and mesh size distribution can vary depending upon a particular application for which the biochar is intended.

FIG. 1 illustrates a cross-section of one example of a raw biochar particle. As illustrated in FIG. 1, a biochar particle 100 is a porous structure that has an outer surface 100a and a pore structure 101 formed within the biochar particle 100. As used herein, unless specified otherwise, the terms "porosity", "porous", "porous structure", and "porous morphology" and similar such terms are to be given their broadest possible meaning, and would include materials having open pores, closed pores, and combinations of open and closed pores, and would also include macropores, mesopores, and micropores and combinations, variations and continuums of these morphologies. Unless specified otherwise, the term "pore volume" is the total volume occupied by the pores in a particle or collection of particles; the term "inter-particle void volume" is the volume that exists between a collection of particle; the term "solid volume or volume of solid means" is the volume occupied by the solid material and does not include any free volume that may be associated with the pore or inter-particle void volumes; and the term "bulk volume" is the apparent volume of the material including the particle volume, the inter-particle void volume, and the internal pore volume.

The pore structure 101 forms an opening 121 in the outer surface 100a of the biochar particle 100. The pore structure 101 has a macropore 102, which has a macropore surface 102a, and which surface 102a has an area, i.e., the macropore surface area. (In this diagram only a single micropore is shown. If multiple micropores are present than the sum of their surface areas would equal the total macropore surface area for the biochar particle.) From the macropore 102, several mesopores 105, 106, 107, 108 and 109 are present, each having its respective surfaces 105a, 106a, 107a, 108a and 109a. Thus, each mesopore has its respective surface area; and the sum of all mesopore surface areas would be the total mesopore surface area for the particle. From the mesopores, e.g., 107, there are several micropores 110, 111, 112, 113, 114, 115, 116, 117, 118, 119 and 120, each having its respective surfaces 110a, 111a, 112a, 113a, 114a, 115a, 116a, 117a, 118a, 119a and 120a. Thus, each micropore has its respective surface area and the sum of all micropore surface areas would be the total micropore surface area for the particle. The sum of the macropore surface area, the mesopore surface area and the micropore surface area would be the total pore surface area for the particle.

Macropores are typically defined as pores having a diameter greater than 300 nm, mesopores are typically defined as diameter from about 1-300 nm, and micropores are typically defined as diameter of less than about 1 nm, and combinations, variations and continuums of these morphologies. The macropores each have a macropore volume, and the sum of these volumes would be the total macropore volume. The mesopores each have a mesopore volume, and the sum of these volumes would be the total mesopore volume. The micropores each have a micropore volume, and the sum of these volumes would be the total micropore volume. The sum of the macropore volume, the mesopore volume and the micropore volume would be the total pore volume for the particle.

Additionally, the total pore surface area, volume, mesopore volume, etc., for a batch of biochar would be the actual, estimated, and preferably calculated sum of all of the individual properties for each biochar particle in the batch.

It should be understood that the pore morphology in a biochar particle may have several of the pore structures shown, it may have mesopores opening to the particle surface, it may have micropores opening to particle surface, it may have micropores opening to macropore surfaces, or other combinations or variations of interrelationship and structure between the pores. It should further be understood that the pore morphology may be a continuum, where moving inwardly along the pore from the surface of the particle, the pore transitions, e.g., its diameter becomes smaller, from a macropore, to a mesopore, to a micropore, e.g., macropore 102 to mesopore 109 to micropore 114.

In general, most biochars have porosities that can range from 0.2 $cm^3/cm^3$ to about 0.8 $cm^3/cm^3$ and more preferably about 0.2 $cm^3/cm^3$ to about 0.5 $cm^3/cm^3$. (Unless stated otherwise, porosity is provided as the ratio of the total pore volumes (the sum of the micro+meso+macro pore volumes) to the solid volume of the biochar. Porosity of the biochar particles can be determined, or measured, by measuring the micro-, meso-, and macro pore volumes, the bulk volume, and the inter particle volumes to determine the solid volume by difference. The porosity is then calculated from the total pore volume and the solid volume.

Figure 2:
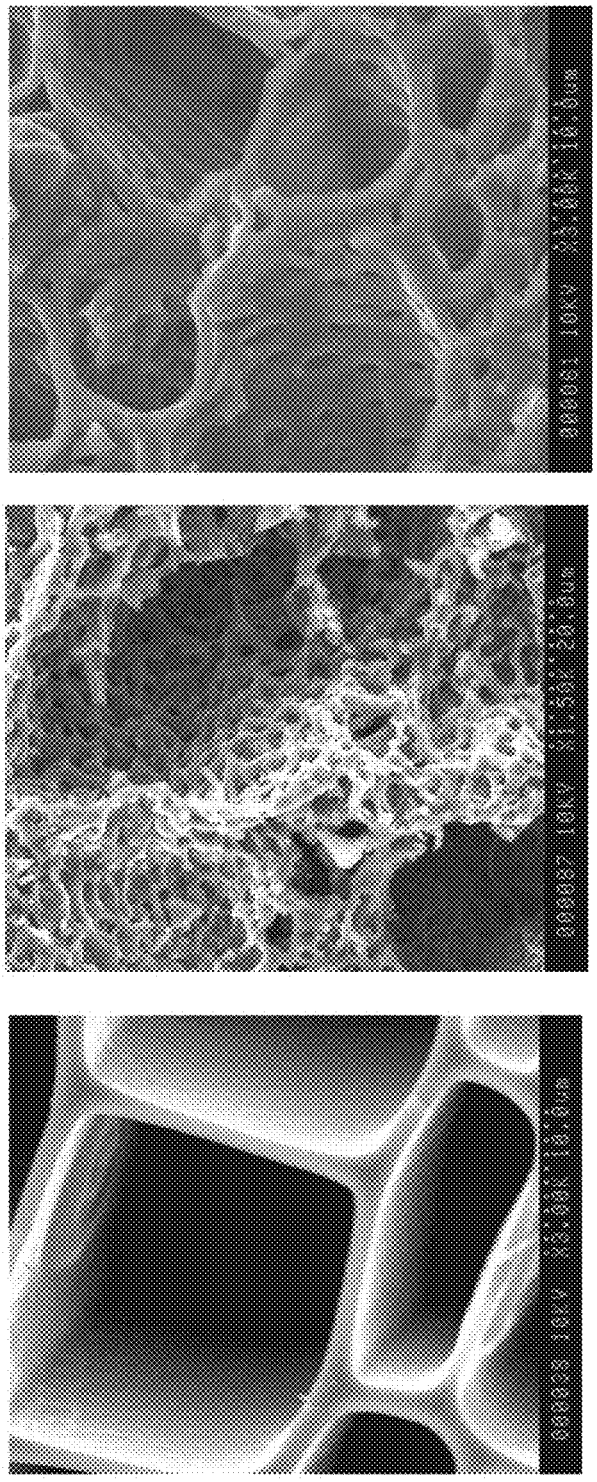
FIG. 2a is a SEM (10 KV×3.00K 10.0 µm) of pore morphology of treated biochar made from pine.
FIG. 2b is a SEM (10 KV×3.00K 10.0 µm) of pore morphology of treated biochar made from birch.
FIG. 2c is a SEM (10 KV×3.00K 10.0 µm) of pore morphology of treated biochar made from coconut shells.

As noted above, the use of different biomass potentially leads to biochars having different properties, including, but not limited to different pore structures. By way of example, FIGS. 2A, 2B and 2C illustrate Scanning Electron Microscope ("SEM") images of various types of treated biochars showing the different nature of their pore morphology. FIG. 2A is biochar derived from pine. FIG. 2B is biochar derived from birch. FIG. 2C is biochar derived from coconut shells.

The surface area and pore volume for each type of pore, e.g., macro-, meso- and micro- can be determined by direct measurement using $CO_2$ adsorption for micro-, $N_2$ adsorption for meso- and macro pores and standard analytical surface area analyzers and methods, for example, particle analyzers such as Micrometrics instruments for meso- and micro pores and impregnation capacity for macro pore volume. Mercury porosimetry, which measures the macroporosity by applying pressure to a sample immersed in mercury at a pressure calibrated for the minimum pore diameter to be measured, may also be used to measure pore volume.

Figure 3:
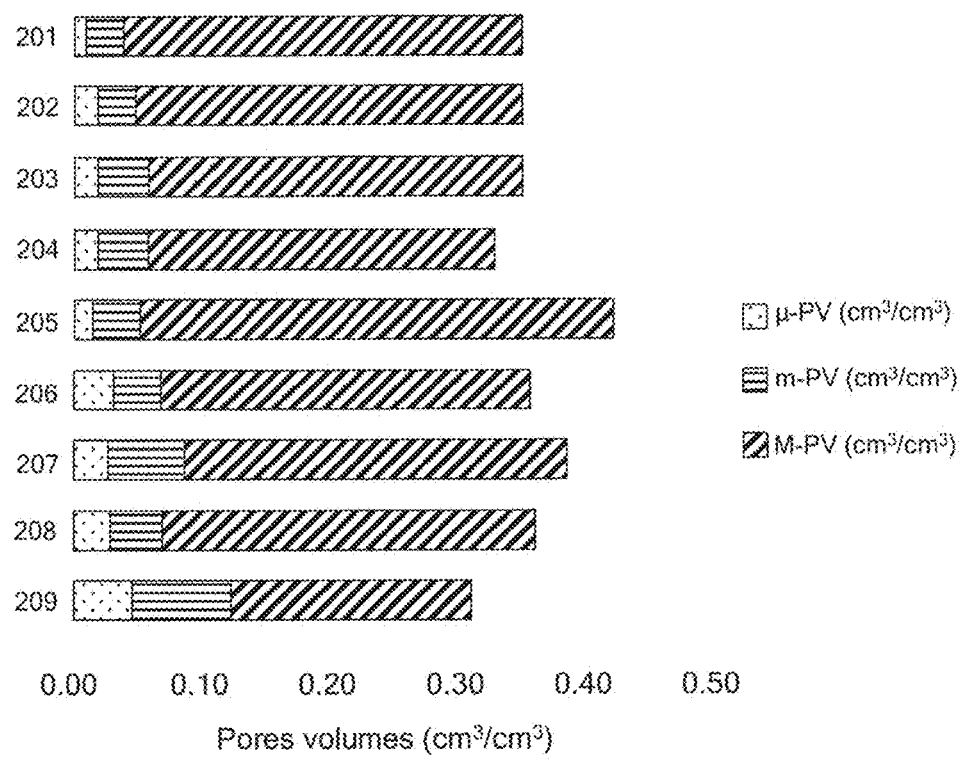
FIG. 3 is a chart showing porosity distribution of various biochars.

The total micropore volume can be from about 2% to about 25% of the total pore volume. The total mesopore volume can be from about 4% to about 35% of the total pore volume. The total macropore volume can be from about 40% to about 95% of the total pore volume. By way of example, FIG. 3 shows a bar chart setting out examples of the pore volumes for sample biochars made from peach pits 201, juniper wood 202, a first hard wood 203, a second hard wood 204, fir and pine waste wood 205, a first pine 206, a second pine 207, birch 208 and coconut shells 209.

As explained further below, treatment can increase usable pore volumes and, among other things, remove obstructions in the pores, which leads to increased retention properties and promotes further performance characteristics of the biochar. Knowing the properties of the starting raw biochar, one can treat the biochar to produce controlled, predictable and optimal resulting physical and chemical properties.

B. Treatment

The rationale for treating the biochar after pyrolysis is that given the large internal pore volume and large interior surface are of the biochars, it is most efficient to make significant changes in the physical and chemical properties of the biochar by treating both the internal and external surfaces and internal pore volume of the char. Testing has demonstrated that if the biochar is treated, at least partially, in a manner that causes the forced infusion and/or diffusion of liquids and/or vapors into and/or out of the biochar pores (through mechanical, physical, or chemical means), certain properties of the biochar can be altered or improved over and above simply contacting these liquids with the biochar. By knowing the properties of the raw biochar and the optimal desired properties of the treated biochar, the raw biochar can then be treated in a manner that results in the treated biochar having controlled optimized properties.

For purposes of this application, treating and/or washing the biochar in accordance with the present invention involves more than simply contacting, washing or soaking, which generally only impacts the exterior surfaces and a small percentage of the interior surface area. "Washing" or "treating" in accordance with the present invention, and as used below, involves treatment of the biochar in a manner that causes the forced, accelerated or assisted infusion and/or diffusion of liquids, vapors, and/or additivities into and/or out of the biochar pores (through mechanical, physical, biological, or chemical means) such that certain properties of the biochar can be altered or improved over and above simply contacting these liquids with the biochar or so that treatment becomes more efficient or rapid from a time standpoint over simple contact or immersion.

In particular, effective treatment processes can mitigate deleterious pore surface properties, remove undesirable substances from pore surfaces or volume, and impact anywhere from between 10% to 99% or more of pore surface area of a biochar particle. By modifying the usable pore surfaces through treatment and removing deleterious substances from the pore volume, the treated biochars can exhibit a greater capacity to retain water and/or other nutrients as well as being more suitable habitats for some forms of microbial life. Through the use of treated biochars, agricultural applications can realize increased moisture control, increased nutrient retention, reduced water usage, reduced water requirements, reduced runoff or leaching, increased nutrient efficiency, reduced nutrient usage, increased yields, increased yields with lower water requirements and/or nutrient requirements, increases in beneficial microbial life, improved performance and/or shelf life for inoculated bacteria, and any combination and variation of these and other benefits.

Treatment further allows the biochar to be modified to possess certain known properties that enhance the benefits received from the use of biochar. While the selection of feedstock, raw biochar and/or pyrolysis conditions under which the biochar was manufactured can make treatment processes less cumbersome, more efficient and further controlled, treatment processes can be utilized that provide for the biochar to have desired and generally sustainable resulting properties regardless of the biochar source or pyrolysis conditions. As explained further below, treatment can (i) repurpose problematic biochars, (ii) handle changing biochar material sources, e.g., seasonal and regional changes in the source of biomass, (iii) provide for custom features and functions of biochar for particular soils, regions or agricultural purposes; (iv) increase the retention properties of biochar, (v) provide for large volumes of biochar having desired and predictable properties, (vi) provide for biochar having custom properties, (vii) handle differences in biochar caused by variations in pyrolysis conditions or manufacturing of the "raw" biochar; and (viii) address the majority, if not all, of the problems that have, prior to the present invention, stifled the large scale adoption and use of biochars.

Treatment can impact both the interior and exterior pore surfaces, remove harmful chemicals, introduce beneficial substances, and alter certain properties of the biochar and the pore surfaces and volumes. This is in stark contrast to simple washing, contact, or immersion which generally only impacts the exterior surfaces and a small percentage of the interior surface area. Treatment can further be used to coat substantially all of the biochar pore surfaces with a surface modifying agent or impregnate the pore volume with additives or treatment to provide a predetermined feature to the biochar, e.g., surface charge and charge density, surface species and distribution, targeted nutrient addition, magnetic modifications, root growth facilitator, and water absorptivity and water retention properties. Just as importantly, treatment can also be used to remove undesirable substances from the biochar, such as dioxins or other toxins either through physical removal or through chemical reactions causing neutralization.

Figure 4:
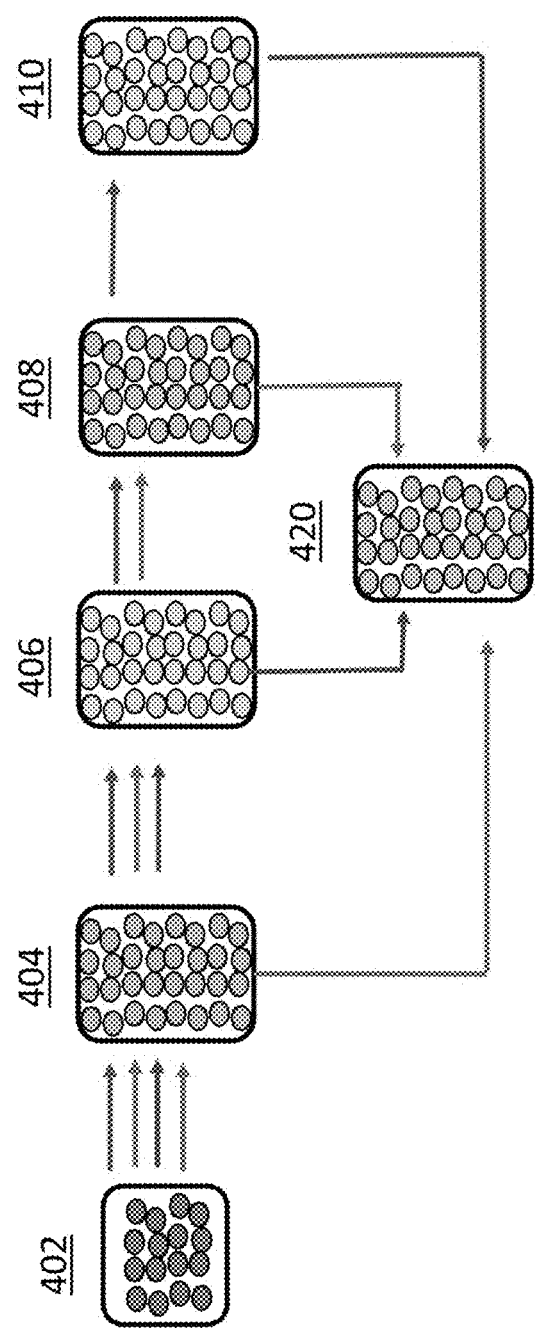
FIG. 4 is a flow chart process diagram of one implementation of a process for treating the raw biochar in accordance with the invention.

FIG. 4 is a schematic flow diagram of one example treatment process 400 for use in accordance with the present invention. As illustrated, the treatment process 400 starts with raw biochar 402 that may be subjected to one or more reactors or treatment processes prior to bagging 420 the treated biochar for resale. For example, 404 represents reactor 1, which may be used to treat the biochar. The treatment may be a simple water wash or may be an acid wash used for the purpose of altering the pH of the raw biochar particles 402. The treatment may also contain a surfactant or detergent to aid the penetration of the treatment solution into the pores of the biochar. The treatment may optionally be heated, cooled, or may be used at ambient temperature or any combination of the three. For some applications, depending upon the properties of the raw biochar, a water and/or acid/alkaline wash 404 (the latter for pH adjustment) may be the only necessary treatment prior to bagging the biochar 420. If, however, the moisture content of the biochar needs to be adjusted, the treated biochar may then be put into a second reactor 406 for purposes of reducing the moisture content in the washed biochar. From there, the treated and moisture adjusted biochar may be bagged 420.

Again, depending upon the starting characteristics of the raw biochar and the intended application for the resale product, further processing may still be needed or desired. In this case, the treated moisture adjusted biochar may then be passed to a third reactor 408 for inoculation, which may include the impregnation of biochar with beneficial additives, such as nutrients, bacteria, microbes, fertilizers or other additives. Thereafter, the inoculated biochar may be bagged 420, or may be yet further processed, for example, in a fourth reactor 410 to have further moisture removed from or added to the biochar. Further moisture adjustment may be accomplished by placing the inoculated biochar in a fourth moisture adjustment reactor 410 or circulating the biochar back to a previous moisture adjustment reactor (e.g. reactor 406). Those skilled in the art will recognize that the ordering in which the raw biochar is processed and certain processes may be left out, depending on the properties of the starting raw biochar and the desired application for the biochar. For example, the treatment and inoculation processes may be performed without the moisture adjustment step, inoculation processes may also be performed with or without any treatment, pH adjustment or any moisture adjustment. All the processes may be completed alone or in the conjunction with one or more of the others. It should also be noted that microbes themselves may be part of the process, not simply as an inoculant, but as an agent to convey materials into or out of the pore volume of the biochar.

Figure 4A:
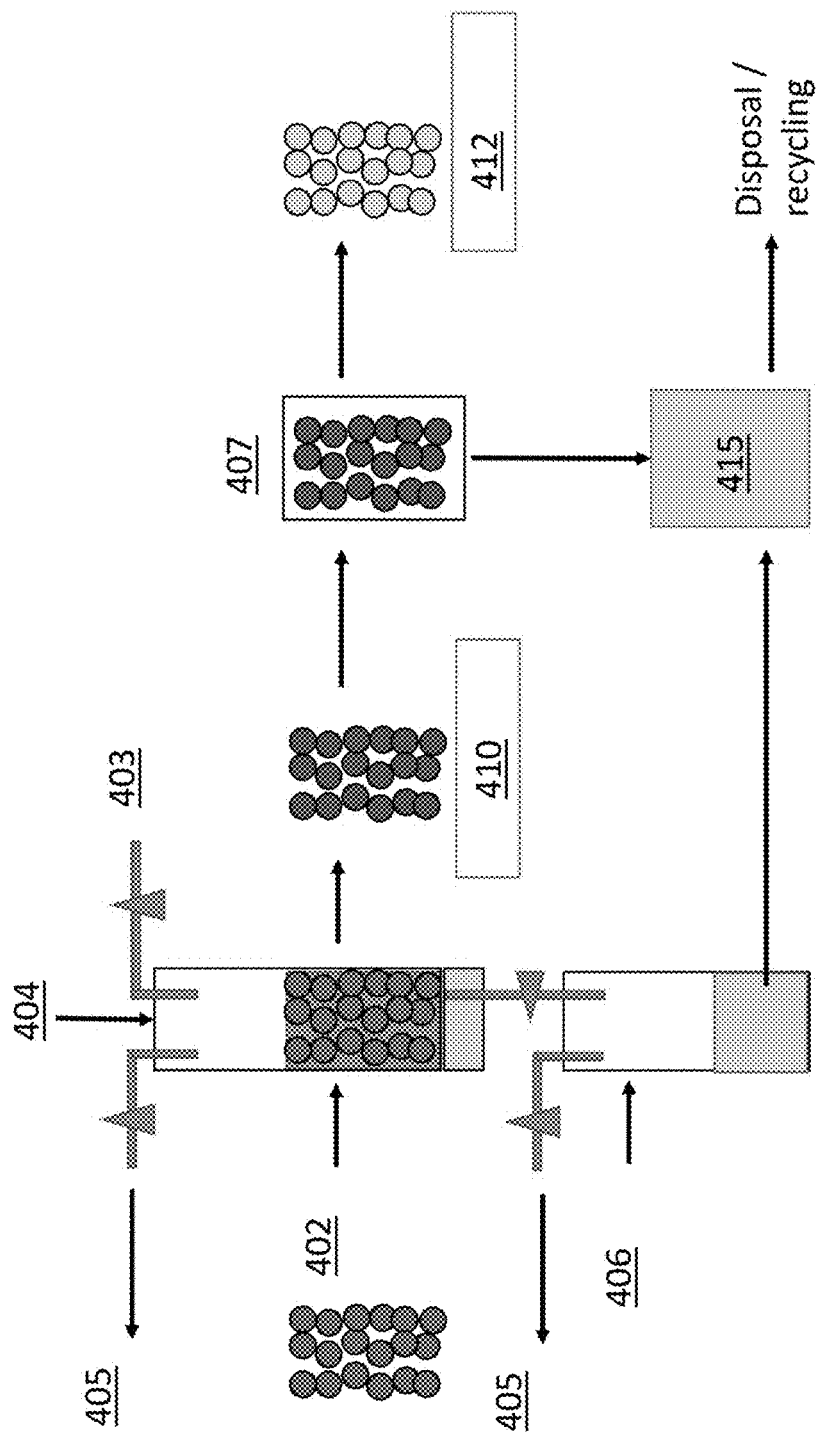
FIG. 4a illustrates a schematic of one example of an implementation of a biochar treat processes that that includes washing, pH adjustment and moisture adjustment.
Figure 4B:
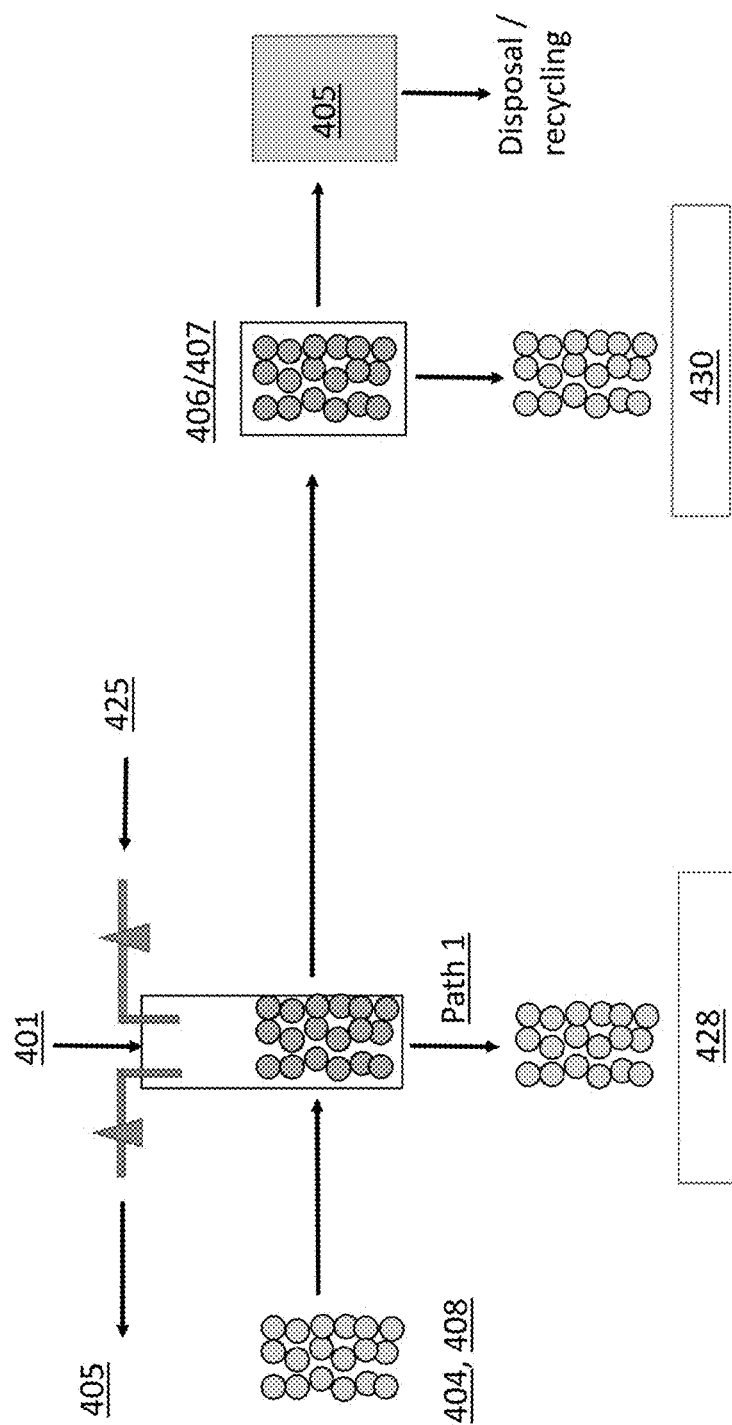
FIG. 4b illustrates yet another example of an implementation of a biochar treatment processing that includes inoculation.

For example, FIG. 4a illustrates a schematic of one example of an implementation of biochar processing that includes washing the pores and both pH and moisture adjustment. FIG. 4b illustrates yet another example of an implementation of biochar processing that includes inoculation.

As illustrated in FIG. 4a, raw biochar 402 is placed into a reactor or tank 404. A washing or treatment liquid 403 is then added to a tank and a partial vacuum, using a vacuum pump, 405 is pulled on the tank. The treating or washing liquid 403 may be used to clean or wash the pores of the biochar 402 or adjust the chemical or physical properties of the surface area or pore volume, such as pH level, usable pore volume, or VOC content, among other things. The vacuum can be applied after the treatment liquid 403 is added or while the treatment liquid 403 is added. Thereafter, the washed/adjusted biochar 410 may be moisture adjusted by vacuum exfiltration 406 to pull the extra liquid from the washed/moisture adjusted biochar 410 or may be placed in a centrifuge 407, heated or subjected to pressure gradient changes (e.g., blowing air) for moisture adjustment. The moisture adjusted biochar 412 may then be bagged or subject to further treatment. Any excess liquids 415 collected from the moisture adjustment step may be disposed of or recycled, as desired. Optionally, biochar fines may be collected from the excess liquids 415 for further processing, for example, to create a slurry, cakes, or biochar extrudates. It should be noted that in any of these steps, the residual gaseous environment in the tanks or centrifuges may be either ambient air, or a prescribed gas or combination of gasses to impact (through assistance or attenuation) reactivity during the process.

Optionally, rather than using a vacuum pump 405, a positive pressure pump may be used to apply positive pressure to the tank 404. In some situations, applying positive pressure to the tank may also function to force or accelerate the washing or treating liquid 403 into the pores of the biochar 402. Any change in pressure in the tank 404 or across the surface of the biochar could facilitate the exchange of gas and/or moisture into and out of the pores of the biochar with the washing or treating liquid 403 in the tank. Accordingly, changing the pressure in the tank and across the surface of the biochar, whether positive or negative, is within the scope of this invention. The atmosphere of the tank may be air or other gaseous mixture, prior to the intuition of the pressure change.

As illustrated FIG. 4b, the washed/adjusted biochar 410 or the washed/adjusted and moisture adjusted biochar 412 may be further treated by inoculating or impregnating the pores of the biochar with an additive 425. The biochar 410, 412 placed back in a reactor 401, an additive solution 425 is placed in the reactor 401 and a vacuum, using a vacuum pump, 405 is applied to the tank. Again, the vacuum can be applied after the additive solution 425 is added to the tank or while the additive solution 425 is being added to the tank. Thereafter, the washed, adjusted and inoculated biochar 428 can be bagged. Alternatively, if further moisture adjustment is required, the biochar can be further moisture adjusted by vacuum filtration 406 to pull the extra liquid from the washed/moisture adjusted biochar 410 or may be placed in a centrifuge 407 for moisture adjustment. The resulting biochar 430 can then be bagged. Any excess liquids 415 collected from the moisture adjustment step may be disposed of or recycled, as desired. Optionally, biochar particulates or "fines" which easily are suspended in liquid may be collected from the excess liquids 415 for further processing, for example, to create a slurry, biochar extrudates, or merely a biochar product of a consistently smaller particle size. As described above, both processes of the FIGS. 4a and 4b can be performed with a surfactant solution in place of, or in conjunction with, the vacuum 405.

While known processes exist for the above described processes, research associated with the present invention has shown improvement and the ability to better control the properties and characteristics of the biochar if the processes are performed through the infusion and diffusion of liquids into and out of the biochar pores. One such treatment process that can be used is vacuum impregnation and vacuum and/or centrifuge extraction. Another such treatment process that can be used is the addition of a surfactant to infused liquid, which infused liquid may be optionally heated, cooled, or used at ambient temperature or any combination of the three.

Since research associated with the present invention has identified what physical and chemical properties have the highest impact on plant growth and/or soil health, the treatment process can be geared to treat different forms of raw biochar to achieve treated biochar properties known to enhance these characteristics. For example, if the pH of the biochar needs to be adjusted to enhance the raw biochar performance properties, the treatment may be the infusion of an acid solution into the pores of the biochar using vacuum, surfactant, or other treatment means. This treatment of pore infusion through, for example, the rapid, forced infusion of liquid into and out the pores of the biochar, has further been proven to sustain the adjusted pH levels of the treated biochar for much longer periods than biochar that is simply immersed in an acid solution for the same period of time. By way of another example, if the moisture content needs to be adjusted, then excess liquid and other selected substances (e.g. chlorides, dioxins, and other chemicals, to include those previously deposited by treatment to catalyze or otherwise react with substances on the interior or exterior surfaces of the biochar) can be extracted from the pores using vacuum and/or centrifuge extraction or by using various heating techniques. The above describes a few examples of treatment that result in treated biochar having desired performance properties identified to enhance soil health and plant life or other applications.

Figure 5:
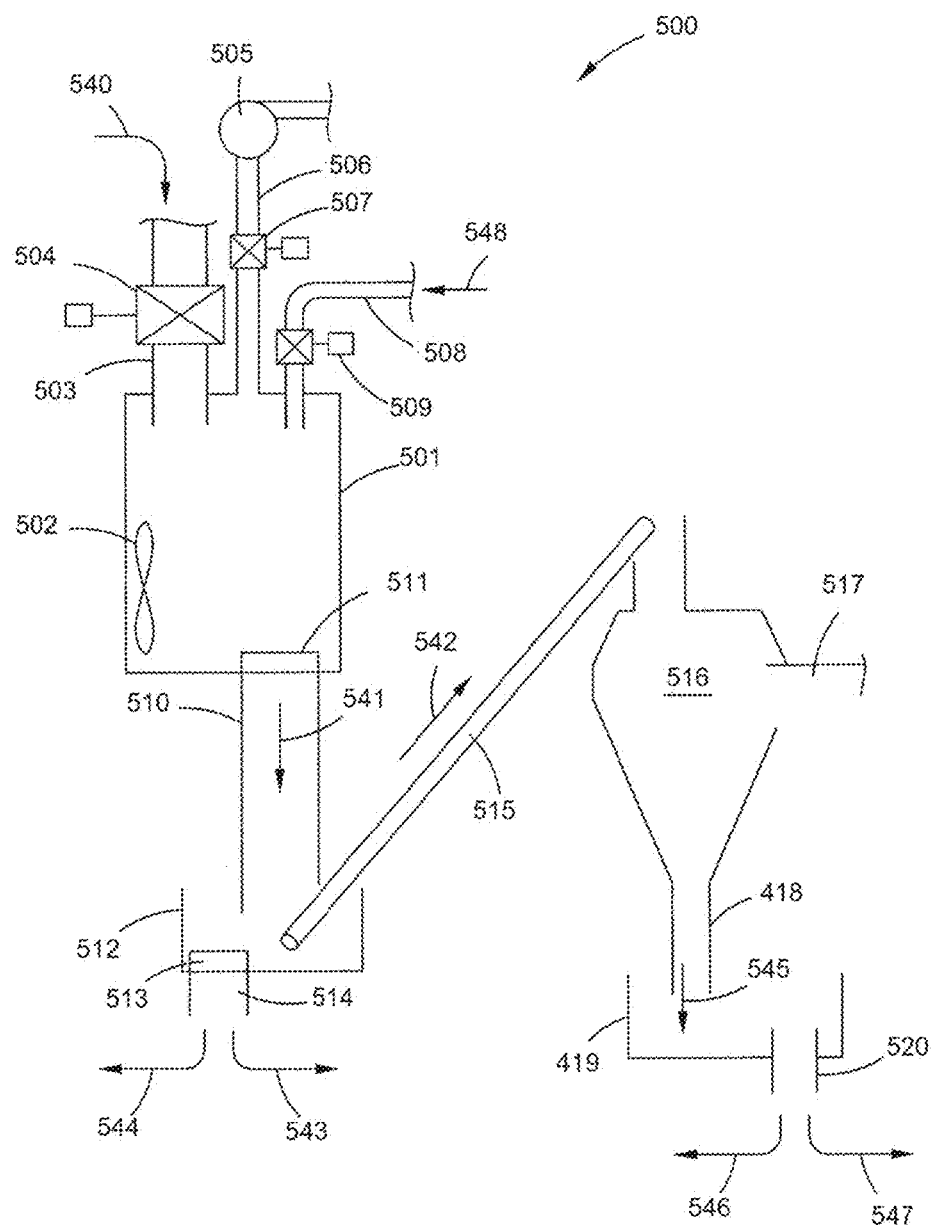
FIG. 5 is a schematic flow diagram of one example of a treatment system for use in accordance with the present invention.

FIG. 5 illustrates one example of a system 500 that utilizes vacuum impregnation to treat raw biochar. Generally, raw biochar particles, and preferably a batch of biochar particles, are placed in a reactor, which is connected to a vacuum pump, and a source of treating liquid (i.e. water or acidic/basis solution). When the valve to the reactor is closed, the pressure in the reactor is reduced to values ranging from 750 Torr to 400 Torr to 10 Torr or less. The biochar is maintained under vacuum ("vacuum hold time") for anywhere from seconds to 1 minute to 10 minutes, to 100 minutes, or possibly longer. By way of example, for about a 500 pound batch of untreated biochar, a vacuum hold time of from about 1 to about 5 minutes can be used if the reactor is of sufficient size and sufficient infiltrate is available to adjust the necessary properties. While under the vacuum the treating liquid may then be introduced into the vacuum chamber containing the biochar. Alternatively, the treating liquid may be introduced into the vacuum chamber before the biochar is placed under a vacuum. Optionally, treatment may also include subjecting the biochar to elevated temperatures from ambient to about 250° C. or reduced temperatures to about −25° C. or below, with the limiting factor being the temperature and time at which the infiltrate can remain flowable as a liquid or semi-liquid.

The infiltrate or treating liquid is drawn into the biochar pore, and preferably drawn into the macropores and mesopores. Depending upon the specific doses applied and pore structure of the biochar, the infiltrate can coat anywhere from 10% to 50% to 100% of the total macropore and mesopore surface area and can fill or coat anywhere from a portion to nearly all (10%-100%) of the total macropore and mesopore volume.

As described above, the treating liquid can be left in the biochar, with the batch being a treated biochar batch ready for packaging, shipment and use in an agricultural or other application. The treating liquid may also be removed through drying, treatment with heated gases, subsequent vacuum processing, centrifugal force (e.g., cyclone drying machines or centrifuges), dilution, or treatment with other liquids, with the batch being a treated biochar batch ready for packaging, shipment and use in an agricultural application. A second, third or more infiltration, removal, infiltration and removal, and combinations and variations of these may also be performed on the biochar with optional drying steps between infiltrations to remove residual liquid from and reintroduce gasses to the pore structure if needed. In any of these stages the liquid may contain organic or inorganic surfactants to assist with the penetration of the treating liquid.

As illustrated in FIG. 5, a system 500 for providing a biochar, preferably having predetermined and generally uniform properties. The system 500 has a vacuum infiltration tank 501. The vacuum infiltration tank 501 has an inlet line 503 that has a valve 504 that seals the inlet line 503. In operation, the starting biochar is added to vacuum infiltration tank 501 as shown by arrow 540. Once the tank is filled with the starting biochar, a vacuum is applied to the tank, by a vacuum pump connected to vacuum line 506, which also has valve 507. The starting biochar is held in the vacuum for a vacuum hold time. Infiltrate, as shown by arrow 548 is added to the tank 501 by line 508 having valve 509. The infiltrate is mixed with the biochar in the tank 501 by agitator 502. The mixing process is done under vacuum for a period of time sufficient to have the infiltrate fill the desired amount of pore volume, e.g., up to 100% of the macropores and mesopores.

Alternatively, the infiltrate may be added to the vacuum infiltration tank 501 before vacuum is pulled on the tank. Optionally, one or more selected gasses may be added to the tank. In this manner, infiltrate is added in the tank in an amount that can be impregnated into the biochar and optionally, the gasses introduced can also potentially impact the reactivity of the liquid as well as any organic or inorganic substances on the surface or in the pore volume of the biochar. As the vacuum is applied, the biochar is circulated in the tank to cause the infiltrate to fill the pore volume. To one skilled in the art, it should be clear that the agitation of the biochar during this process can be performed through various means, such as a rotating tank, rotating agitator, pressure variation in the tank itself, or other means. Additionally, the biochar may be dried using conventional means before even the first treatment. This optional pre-drying can remove liquid from the pores and in some situations may increase the efficiency of impregnation due to pressure changes in the tank.

Pressure is then restored in the tank 501 with either ambient air or a prescribed selection of gasses, and the infiltrated biochar is removed, as shown by arrow 541, from the tank 501 to bin 512, by way of a sealing gate 511 and removal line 510. The infiltrated biochar is collected in bin 512, where it can be further processed in several different ways. The infiltrated biochar can be shipped for use as a treated biochar as shown by arrow 543. The infiltrated biochar can be returned to the tank 501 (or a second infiltration tank). If returned to the tank 501 the biochar can be processed with a second infiltration step, a vacuum drying step, a washing step, or combinations and variations of these. The infiltrated biochar can be moved by conveyor 514, as shown by arrow 542, to a drying apparatus 516, e.g., a centrifugal dryer or heater, where water, infiltrate or other liquid is removed by way of line 517, and the dried biochar leaves the dryer through discharge line 518 as shown by arrow 545, and is collected in bin 519. The biochar is removed from the bin by discharge 520. The biochar may be shipped as a treated biochar for use in an agriculture application, as shown by arrow 547. The biochar may also be further processed, as shown by 546. Thus, the biochar could be returned to tank 501 (or a second vacuum infiltration tank) for a further infiltration step. The drying step may be repeated either by returning the dry biochar to the drying apparatus 516, or by running the biochar through a series of drying apparatus, until the predetermined dryness of the biochar is obtained, e.g., between 50% to less than 1% moisture.

The system 500 is illustrative of the system, equipment and processes that can be used for, and to carry out the present inventions. Various other implementations and types of equipment can be used. The vacuum infiltration tank can be a sealable off-axis rotating vessel, chamber or tank. It can have an internal agitator that also when reversed can move material out, empty it, (e.g., a vessel along the lines of a large cement truck, or ready mix truck, that can mix and move material out of the tank, without requiring the tank's orientation to be changed). Washing equipment may be added or utilized at various points in the process, or may be carried out in the vacuum tank, or drier, (e.g., wash fluid added to biochar as it is placed into the drier for removal). Other steps, such as bagging, weighing, the mixing of the biochar with other materials, e.g., fertilized, peat, soil, etc. can be carried out. In all areas of the system referring to vacuum infiltration, optionally positive pressure can be applied, if needed, to enhance the penetration of the infiltrate or to assist with re-infusion of gaseous vapors into the treated char. Additionally, where feasible, especially in positive pressure environments, the infiltrate may have soluble gasses added which then can assist with removal of liquid from the pores, or gaseous treatment of the pores upon equalization of pressure.

As noted above, the biochar may also be treated using a surfactant. The same or similar equipment used in the vacuum infiltration process can be used in the surfactant treatment process. Although it is not necessary to apply a vacuum in the surfactant treatment process, the vacuum infiltration tank or any other rotating vessel, chamber or tank can be used. In the surfactant treatment process, a surfactant, such as yucca extract, is added to the infiltrate, e.g., acid wash or water. The quantity of the surfactant added to the infiltrate may vary depending upon the surfactant used. For example, organic yucca extract can be added at a rate of between 0.1-20%, but more preferably 1-5% by volume of the infiltrate. The infiltrate with surfactant is then mixed with the biochar in a tumbler for several minutes, e.g., 3-5 minutes, without applied vacuum. Optionally, a vacuum or positive pressure may be applied with the surfactant to improve efficiency and penetration, but is not strictly necessary. Additionally, infiltrate to which the surfactant or detergent is added may be heated or may be ambient temperature or less. Similarly, the mixture of the surfactant or detergent, as well as the char being treated may be heated, or may be ambient temperature, or less. After tumbling, excess free liquid can be removed in the same manner as described above in connection with the vacuum infiltration process. Drying, also as described above in connection with the vacuum infiltration process, is an optional additional step. Besides yucca extract, a number of other surfactants may be used for surfactant treatment, which include, but are not limited to, the following: nonionic types, such as, ethoxylated alcohols, phenols—lauryl alcohol ethoxylates, Fatty acid esters—sorbitan, tween 20, amines, amides—imidazoles; anionic types, such as sulfonates—arylalkyl sulfonates and sulfate—sodium dodecyl sulfate; cationic types, such as alkyl—amines or ammoniums—quaternary ammoniums; and amphoteric types, such as betaines—cocamidopropyl betaine. Additionally biosurfactants, or microbes which produce biosurfactants such as *Flavobacterium* sp. may also be used.

Optionally, the biochar may also be treated by applying ultrasonics. In this treatment process, the biochar may be contacted with a treating liquid that is agitated by ultrasonic waves. By agitating the treating liquid, contaminants may be dislodged or removed from the biochar due to bulk motion of the fluid in and around the biocarbon, pressure changes, including cavitation in and around contaminants on the surface, as well as pressure changes in or near pore openings (cavitation bubbles) and internal pore cavitation.

In this manner, agitation will cause contaminants of many forms to be released from the internal and external structure of the biochar. The agitation also encourages the exchange of water, gas, and other liquids with the internal biochar structure. Contaminants are transported from the internal structure to the bulk liquid (treating fluid) resulting in biochar with improved physical and chemical properties. The effectiveness of ultrasonic cleaning is tunable as bubble size and number is a function of frequency and power delivered by the transducer to the treating fluid In one example, applying ultrasonic treatment, raw wood based biochar between 10 microns to 10 mm with moisture content from 0% to 90% may be mixed with a dilute mixture of acid and water (together the treating liquid) in a processing vessel that also translates the slurry (the biochar/treating liquid mixture). During translation, the slurry passes near an ultrasonic transducer to enhance the interaction between the fluid and biochar. The biochar may experience one or multiple washes of dilute acid, water, or other treating fluids. The biochar may also make multiple passes by ultrasonic transducers to enhance physical and chemical properties of the biochar. For example, once a large volume of slurry is made, it can continuously pass an ultrasonic device and be degassed and wetted to its maximum, at a rapid processing rate. The slurry can also undergo a separation process in which the fluid and solid biochar are separated at 60% effectiveness or greater.

Through ultrasonic treatment, the pH of the biochar, or other physical and chemical properties may be adjusted and the mesopore and macropore surfaces of the biochar may be cleaned and enhanced. Further, ultrasonic treatment can be used in combination with bulk mixing with water, solvents, additives (fertilizers, etc.), and other liquid based chemicals to enhance the properties of the biochar. After treatment, the biochar may be subject to moisture adjustment, further treatment and/or inoculation using any of the methods set forth above.

Testing has further demonstrated that if the biochar is treated, at least partially, in a manner that causes the infusion and/or effusion of liquids and/or vapors into and/or out of the biochar pores (through mechanical, physical, biological, or chemical means), certain beneficial properties of the biochar can be altered, enhanced or improved through treatment. By knowing the properties of the raw biochar and the optimal desired properties of the treated biochar, the raw biochar can then be treated in a manner that results in the treated biochar having controlled optimized properties and greater levels of consistency between batches as well as between treated biochars arising from various feedstocks.

Using the treatment processes described above, or other treatments that provide, in part, for the infusion and/or effusion of liquids and/or vapors into and/or out of the biochar pores, biochars can have improved physical and chemical properties over raw biochar.

The table below, illustrates some of the important physical and chemical properties of biochar that can be achieved through treatment methods of the present invention:

| PROPERTY | NUMERIC VALUES |
|---|---|
| Bulk Density | 0.1-0.6 g/cm$^3$ |
| Solid Particle Density | 0.2-1.2 g/cm$^3$ |
| Impregnation/Absorption Capacity (IC) | 0.2-0.8 cm$^3$/cm$^3$ |
| Water Holding Capacity (WHC)/Water Retention Capacity (WRC) | Volumetric: Above 30% (volume of water/volume biochar) Gravimetric: 100-400% (wet weigh-dry weight/dry weight) |
| Plant Available Water | ≥35 wt % |
| Surface Area | 200-600 m2/g |
| TGA (H2O) | 0% ≤ x ≤ 80% by weight Preferred: 20% ≤ x ≤ 80% by weight |
| Percentage Total Residual Organic Compound Content | 0-30 wt. % |
| Percentage Heavy ROC Content | 0-20 wt. % |
| Percentage VOC Content | Less than 5% |
| Acidity (pH) | pH <8.5, optimal 6.5 < pH < 5 |
| Percentage of pore volume >300 nm to total pore volume | 50% |
| Ash Content | 0.1-5 wt. % |
| Remaining Water Content | 100-650 mL/kg; 45-150 mL/L; 12-30 gal/ton; 3-10 gal/yd3 after 360 hours (15 days) of exposure to the environment |
| Electrical conductivity | >0.2 ds/m |
| Cation Exchange Capacity | ≥5 millieq/l |
| Anion Exchange Capacity | ≥5 millieq/l |
| Dioxins TEQ | <0.75 ng/kg WHO-PCDD/F-TEQ//kg (with <0.5 ng/kg WHO-PCDD/F-TEQ//kg optimal) |
| Hydrophilicity | 0-4 (Indexed by MED testing) 0-4 (Indexed by Infiltrometer testing) |

C. Impact of Treatment

As illustrated above, the treatment process, whether using pressure changes (e.g. vacuum), surfactant or ultrasonic treatment, or a combination thereof, may include two steps, which in certain applications, may be combined: (i) washing and (ii) inoculation of the pores with an additive. When the desired additive is the same and that being inoculated into the pores, e.g., water, the step of washing the pores and inoculating the pores with an additive may be combined.

While not exclusive, washing is generally done for one of three purposes: (i) to modify the surface of the pore structure of the biochar (i.e., to allow for increased retention of liquids); (ii) to modify the pH of the biochar; and/or (iii) to remove undesired and potentially harmful compounds or gases.

The above data has been verified, by the testing set forth herein, using treated biochars containing mostly particle sizes less than or equal to 10 mm and greater than 0.5 mm. In general, for most batches of biochar, greater than seventy-five percent (75%) of the biochars tested in batch by both volume and weight have particle sizes less than or equal to 10 mm, where approximately 75% of the biochars tested in batch have particles sizes less than or equal to 5 mm. As also set forth above, the biochars tested have at least 55% carbon content based upon weight. When measuring particle size, as particle size distribution in a batch, a cumulative method of measure is used. When measured in a batch of particles, the cumulative particle size distribution is the percentage of the particles in the batch that will pass through a uniform sieve of a given size.

Regarding measurement of the above properties, the properties are defined and measured as set forth below:

| ATTRIBUTE | DEFINITION | UNIT OF MEASURE | METHOD OF MEASURE |
| --- | --- | --- | --- |
| Impregnation Capacity | The amount of water that can be held internally within the porous structure (micro, meso, and macro pores) of a given particle or batch of particles, measured by the amount of liquid that can be infused into biochar by vacuum impregnation. | Either volumetric ($cm^3$ liquid per $cm^3$ particles) or gravimetric (gm liquid per gm particles) | Example measurement techniques: Measure specific amount (grams of mL) of biochar; dry the sample at 120 C. for 2 hrs.; transfer the sample into sealed vacuum reactor and apply vacuum of 15 to 30 inches Hg; start adding water drop wise to the biochar under vacuum; at the first sight of water not impregnated into the pores (incipient wetness) stop and measure the amount of water added up to this point; this water amount divided by the samples mass or volume will give the impregnation capacity. Alternative measurement: Dry substance completely (through heating or other means); weigh substance; expose substance to water while removing adsorbed gasses with partial vacuum by apply vacuum of 15 to 30 inches Hg; remove interspatial water by centrifuge or other surface drying technology. Do not heat to remove water in pores; weigh substance; the difference in the two weights of the substance of the initial dry weigh of the substance measures impregnation capacity. |
| Water Holding Capacity/Water Retention Capacity | The amount of water that can be held both internally within the porous structure, sorbed onto the particle surface and in the interparticle void spaces in a given batch of particles without forced infusion techniques. | Volumetric: (ml liquid/ ml particles or L liquid/L particles) Gravimetric (wet weight-dry weight/dry weight) | 1. Dry sample of biochar 2. Place sample in a container 3. Fill container with water 4. Drain container 5. Measure mass of sample (i.e., wet weight) 6. Dry sample (preferably by exposure to heat at or above boiling point of water) 7. Measure mass of sample (i.e., dry weight) and/or determine sample volume |
| Plant Available Water | The difference of water content at field capacity from the water content at the permanent wilting point, which is the point when no water is available for the plants | % mass by weight | A pressure plate extractor is used to measure plant available water |
| $H_2O$ (TGA) | $H_2O$ (TGA) represents the mass of water contained in the sample measured through Thermogravimetric analysis ("TGA"). | % mass by weight | Thermogravimetric analysis of a given sample indicating % water in a sample is determined by % mass loss measured between standard temperature and 150 degrees C. |
| Total ROC (TGA) | Total ROC (TGA) represents the mass of residual organic compounds (light and heavy) contained in a sample. | % mass by weight | Thermogravimetric analysis of a given sample indicating % of residual organic compounds is measured by % mass loss sustained between 150 degrees C. and 950 degrees C. |
| VOC % (TGA) | Total ROC (TGA) represents the mass of residual light organic compounds (volatiles) contained in the sample. | % mass by weight | Thermogravimetric analysis of a given sample indicating % of light organic compounds (volatiles) is measured by % mass loss sustained between 150 degrees C. and 550 degrees C. |

-continued

| ATTRIBUTE | DEFINITION | UNIT OF MEASURE | METHOD OF MEASURE |
|---|---|---|---|
| Heavy ROC % (TGA) | TGA (Total ROC) represents the mass of mass of residual heavy organic compounds contained in the sample. | % mass by weight | Thermogravimetric analysis of a given sample indicating % of heavy organic compounds is measured by % mass loss sustained between 550 degrees C. and 950 degrees C. |
| pH | The acidity of the biochar | pH | Mix biochar into deionized water at a ratio of 1 part BC to 5 parts water [mass:volume] ratio, for example, 50 g biochar + 250 mL DI water. Still slurry for 10 minutes using a standard magnetic stirrer. Measure pH of the slurry using standard pH measurement technology (i.e., a standard laboratory pH meter). |
| Porosimetry - Volume of Meso and Macro pores (3 nm-360,000 nm) | Mesopore and Macropore volume (pores between 3 nm and 360,000 nm) in a material sample over total sample volume | Weight based porosity (pore volume/weight) cc/g or Volume based porosity (pore volume/bulk volume) cc/ml | Determined by mercury porosimetry, which measures the meso & macro porosity by applying pressure to a sample immersed in mercury at a pressure calibrated for the desired minimum pore diameter to be measured. |
| Percentage of pore volume > 300 nm to total pore volume | Percentage of macropore volume in a sample greater than 300 nm in diameter over total pore volume | ml pores > 300 nm/ml substance/ml total pores/ml substance | Macropore volume is determined by mercury porosimetry, which measures the macroporosity by applying pressure to a sample immersed in mercury at a pressure calibrated for the minimum pore diameter (300 nm) to be measured. Total volume of pores per volumetric unit of substance is measured using gas expansion method. |
| Remaining Water Content | The total amount of water that remains held by the biochar after exposure to the environment for certain amount of time. | mL/kg; mL/L | 1. Create a sample of biochar where the biochar has reached its maximum water holding capacity; 2. Determine (using a portion of the sample) the total water content by thermogravimetric analysis (H2O (TGA)) 3. Expose the biochar (in the remaining sample) to the environment for a period of 2 weeks, 1 day (15 days, 360 hrs.); 4. Determine the remaining water content by thermogravimetric analysis (H2O (TGA)); and 5. Normalizing the remaining (retained) water in mL to 1 kg or 1 L biochar. |
| Electrical Conductivity | Electrical conductivity is the measure of the amount of electrical current a material can carry. | ds/m | Following the USDA Soil Quality Test Kit Guide, material is mixed with deionized water on a 1:1 material to water ratio on a volume basis. The electrical conductivity is then measured using a commonly available EC meter - consisting of two electrodes and a constant current flowing through the material between the electrodes. |

-continued

| ATTRIBUTE | DEFINITION | UNIT OF MEASURE | METHOD OF MEASURE |
| --- | --- | --- | --- |
| Cation Exchange Capacity | Cation exchange capacity (CEC) is the total capacity of a soil to hold exchangeable cations. CEC is an inherent soil characteristic and is difficult to alter significantly. It influences the soil's ability to hold onto essential nutrients and provides a buffer against soil acidification. | millieq/l | CEC may be determined through the use of ammonium acetate buffered at pH 7.0. The material is saturated with 1M ammonium acetate, (NH$_4$OAc), followed by the release of the NH$_4^+$ ions and its measurement in meq/100 g (milliequivalents of charge per 100 g of dry soil) or cmolc/kg (centimoles of charge per kilogram of dry soil). Instead of ammonium acetate another method uses barium chloride. 0.1M BaCl$_2$ is used to saturate the exchange sites followed by replacement with either MgSO$_4$ or MgCl$_2$. Indirect methods for CEC calculation involves the estimation of extracted Ca$_2^+$, Mg$_2^+$, K$^+$, and Na$^+$ in a standard soil test using Mehlich 3 and accounting for the exhangeable acidity (sum of H$^+$, Al$_3^+$, Mn$_2^+$, and Fe$_2^+$) if the pH is below 6.0 |
| Anion Exchange Capacity | AEC is the degree to which a soil can adsorb and exchange anions, AEC increases as soil pH decreases. The pH of most productive soils is usually too high (exceptions are for volcanic soils) for full development of AEC and thus it generally plays a minor role in supplying plants with anions. | millieq/l | AEC is calculated directly or indirectly by saturated paste extraction of exchangeable anions, Cl$^-$, NO$_3^-$, SO$_4^{2-}$, and PO4$^{3-}$ to calculate anion sum or the use of potassium bromide to saturate anions sites at different pHs and repeated washings with calcium chloride and final measurement of bromide |
| Dioxins TEQ | Polychlorinated dibenzo-p-dioxins (PCDDs) (i.e., 75 congeners (10 are specifically toxic)); Polychlorinated dibenzofurans (PCDFs) (i.e., 135 congeners (7 are specifically toxic)) and Polychlorinated biphenyls (PCBs) (Considered dioxin-like compounds (DLCs)) | ng/kg WHO-PCDD/F-TEQ//kg | Two methods are used: EPA Method 8290 (for research and understanding at low levels (ppt-ppq); and EPA Method 1613B (for regulatory compliance). Both are based on high resolution gas chromatography (HRGC)/high resolution mass spectrometry (HRMS). |
| Hydrophilicity | Measure of the affinity of the material to absorb or associate with water (the lower the indexed number the more affinity the biochar has to absorb water and thus the more hydrophillic) | Indexed | Molarity of Ethanol Drop Test ("MED Test") 1. Make seven solutions of deionized ("DI") water with the following respective percentages of ethanol: 3, 5, 11, 13, 18, 24 and 36. The test started with a mixture having no DI. 2. Place biochar in container prepared for testing 3. Start with DI water testing (solution 0 - no ethanol); Test multiple drop laid onto the substrate surface from low height. If drops soak in less than 3 seconds, record substrate as "0." If drops take longer than 3 seconds or don't soak in, go to test solution 1. 4. Test Solution 1; Test multiple drops from dropper laid onto the surface from low height. If drops soak into the substrate in less than 3 seconds, record material as "1." If drops take longer than 3 seconds, or don't soak in, go to test solution 2. |

| ATTRIBUTE | DEFINITION | UNIT OF MEASURE | METHOD OF MEASURE |
|---|---|---|---|
| | | | 5. Test solution 2; Test multiple drops from dropper laid onto the surface from low height. If drops soak into the substrate in less than 3 seconds, record material as "2." If drops take longer than 3 seconds, or don't soak in, go to test solution 3. Proceed as above, testing progressively higher numbered MED solutions until you find the solution that soaks into the substrate in 3 seconds or less. The substrate is recorded as having that Hydrophobicity Index number assigned to it (0-7, with 0 being very hydrophilic and 7 strongly hydrophobic). |
| Hydrophilicity | Measure of the affinity of the material to absorb or associate with water (the lower the indexed number the more affinity the biochar has to absorb water and thus the more hydrophillic) | Indexed | Infiltrometer Testing 1. Fill the bubble chamber three quarters full with tap water for both water and ethanol sorptivity tests. Do NOT use distilled or DI water. 2. Once the upper chamber is full, invert the infiltrometer and fill the water reservoir with 80 mL. 3. Carefully set the position of the end of the mariotte tube with respect to the porous disk to ensure a zero suction offset while the tube bubbles. If this dimension is changed accidentally, the end of the mariotte tube should be reset to 6 mm from the end of the plastic water reservoir tube. 4. Replace the bottom elastomer, making sure the porous disk is firmly in place. 5. If the infiltrometer is held vertically using a stand and clamp, no water should leak out. 6. Set the suction rate of 1 cm for all samples. 7. If the surface of the sample is not smooth, a thin layer of fine biochar being tested can be applied to the area directly underneath the infiltrometer stainless steel disk. This ensures good contact between the samples and the infiltrometer. 8. When we take the reading, the interval is 1 min for both water and ethanol sorptivity test. 9. To be accurate, 20 mL water or 95% ethanol needs to be infiltrated into the samples. 10. Record time and water/ethanol volume. Data Processing 1. Input the volume levels and time to the corresponding volume column |

| ATTRIBUTE | DEFINITION | UNIT OF MEASURE | METHOD OF MEASURE |
|---|---|---|---|
| | | | 2. Use the following equation to calculate the hydrophobicity index of R $I = at + b\sqrt{t}$ $a$: Infiltration Rate, cm/s $b$: Sorptivity, cm/s$^{1/2}$ $$R = 1.95 * \frac{b_{ethanol}}{b_{water}}$$ |

1. Impregnation Capacity

As illustrated above, "impregnation capacity" is defined as the amount of water that can be held internally within the porous structure (micro, meso, and macro pores) of a given particle or batch of particles. This is measured by determining the maximum amount of liquid that can be infused into biochar by vacuum impregnation. The measurement can be taken either volumetric (ml liquid per ml particles) or gravimetric (gm liquid per gm particles). More than one measurement technique can be used to determine the impregnation capacity. In one example, the measurement is determined by the following procedure: (i) measure a specific amount (grams or mL) of biochar; (ii) dry the sample at 120° C. for 2 hrs.; (iii) transfer the sample into sealed vacuum reactor and apply vacuum of 15 to 30 inches Hg; (iv) start adding water drop wise to the biochar under vacuum; (v) at the first sight of water not impregnated into the pores (incipient wetness) stop and measure the amount of water added up to this point; (vi) this water amount divided by the samples mass or volume will give the impregnation capacity.

In another example, impregnation capacity is measured by the following procedure: (i) measure a specific amount of biochar (grams or mL); (ii) dry the biochar by, for example, heating the biochar under a temperature of 120° C. for a period of 2 hours or until mass loss is below 0.1% in a 5 minute period, or by using another acceptable technique to reduce the moisture content of the biochar to less than 2% and preferably less than 1%; (iii) weigh the biochar; (iii) expose the biochar to water while removing the absorbed gasses with a partial vacuum of 15 to 30 inches Hg; (iv) removing interspatial water by centrifuge or other surface drying technology (excluding heat); and (v) weighing the biochar. The difference in weight of the substance in step (ii) from step (v) over the total weight of the substance from step (ii) determines the impregnation capacity of the biochar. This number can be then be presented as a measurement by mass or volume.

2. Water Holding/Retention Capacity

As demonstrated below, the treatment processes of the invention modifies the surfaces of the pore structure to provide enhanced functionality and to control the properties of the biochar to achieve consistent and predicable performance. Using the above treatment processes, anywhere from at least 10% of the total pore surface area up to 90% or more of the total pore surface area may be modified. In some implementations, it may be possible to achieve modification of up to 99% or more of the total pore surface area of the biochar particle. Using the processes set forth above, such modification may be substantially and uniformly achieved for an entire batch of treated biochar.

For example, it is believed that by treating the biochar as set forth above, the hydrophilicity of the surface of the pores of the biochar is modified, allowing for a greater water retention capacity. Further, by treating the biochars as set forth above, gases and other substances are also removed from the pores of the biochar particles, also contributing to the biochar particles' increased water holding capacity. Thus, the ability of the biochar to retain liquids, whether water or additives in solution, is increased, which also increases the ability to load the biochar particles with large volumes of inoculant, infiltrates and/or additives.

A batch of biochar has a bulk density, which is defined as weight in grams (g) per cm$^3$ of loosely poured material that has or retains some free space between the particles. The biochar particles in this batch will also have a solid density, which is the weight in grams (g) per cm$^3$ of just particles, i.e., with the free space between the particles removed. The solid density includes the air space or free space that is contained within the pores, but not the free space between particles. The actual density of the particles is the density of the material in grams (g) per cm$^3$ of material, which makes up the biochar particles, i.e., the solid material with pore volume removed.

In general, as bulk density increases the pore volume would be expected to decrease and, if the pore volume is macro or mesoporous, with it, the ability of the material to hold infiltrate, e.g., inoculant. Thus, with the infiltration processes, the treated biochars can have impregnation capacities that are larger than could be obtained without infiltration, e.g., the treated biochars can readily have 10%, 30%, 40%, 50%, or most preferably, 60%-100% of their total pore volume filled with an infiltrate, e.g., an inoculant. The impregnation capacity is the amount of a liquid that a biochar particle, or batch of particles, can absorb. The ability to make the pores surface hydrophilic, and to infuse liquid deep into the pore structure through the application of positive or negative pressure and/or a surfactant, alone or in combination, provides the ability to obtain these high impregnation capabilities. The treated biochars can have impregnation capacities, i.e., the amount of infiltrate that a particle can hold on a volume held/total volume of a particle basis, that is greater than 0.2 cm$^3$/cm$^3$ to 0.8 cm$^3$/cm$^3$.

Figure 6:
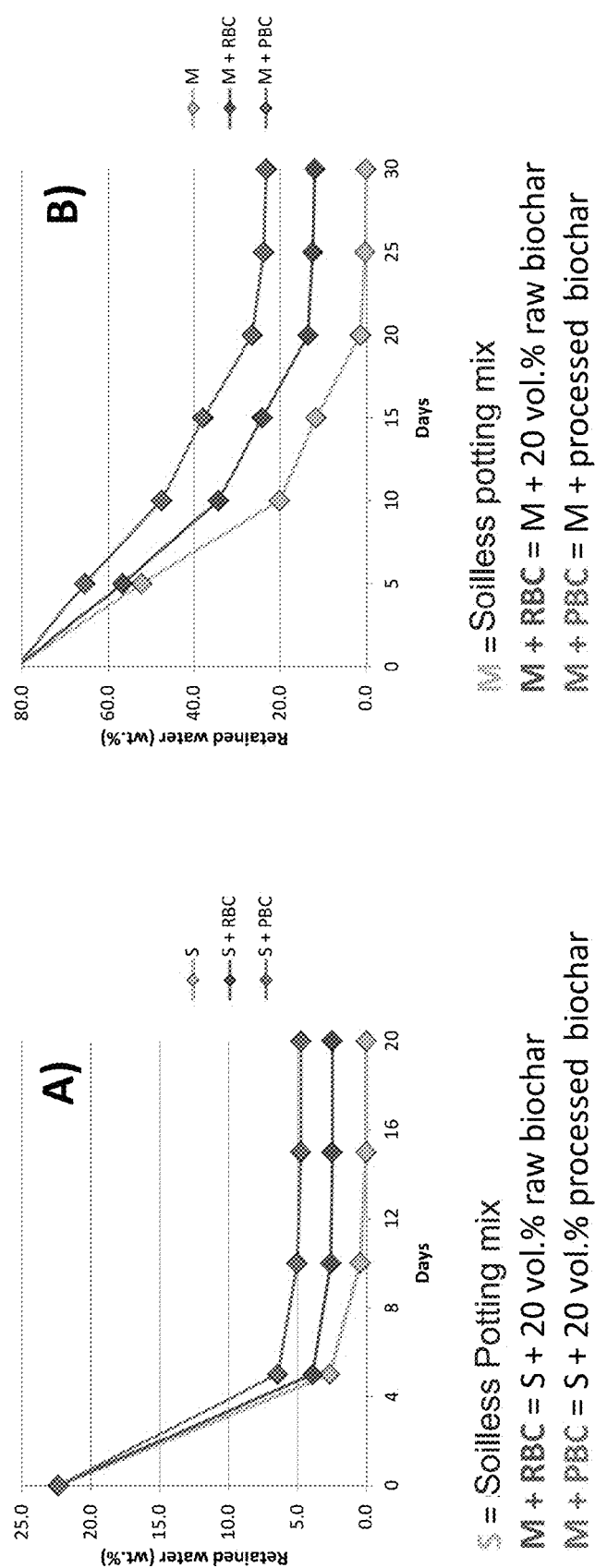
FIG. 6 is a chart showing the water holding capacities of treated biochar as compared to raw biochar and sandy clay loam soil and as compared to raw biochar and soilless potting soil.

Accordingly, by using the treatment above, the water retention capacity of biochar can be greatly increased over the water retention capacities of various soil types and even raw biochar, thereby holding water and/or nutrients in the plant's root zone longer and ultimately reducing the amount of applied water (through irrigation, rainfall, or other means) needed by up to 50% or more. FIG. 6 has two charts showing the water retention capacities of planting substrates versus when mixed with raw and treated biochar. In this example, the raw and treated biochar are derived from coconut biomass. The soils sampled are loam and sandy clay soil and a common commercial horticultural peat and perlite soilless potting mix. The charts show the retained water as a function of time.

In chart A of FIG. 6, the bottom line represents the retained water in the sandy claim loam soil over time. The middle line represents the retained water in the sandy clay soil with 20% by volume percent of unprocessed raw biochar. The top line represents the retained water in the sandy clay loam soil with 20% by volume percent of treated biochar (adjusted and inoculated biochar). Chart B of FIG. 6 represents the same using peat and perlite soilless potting mix rather than sandy clay loam soil.

Figure 7:
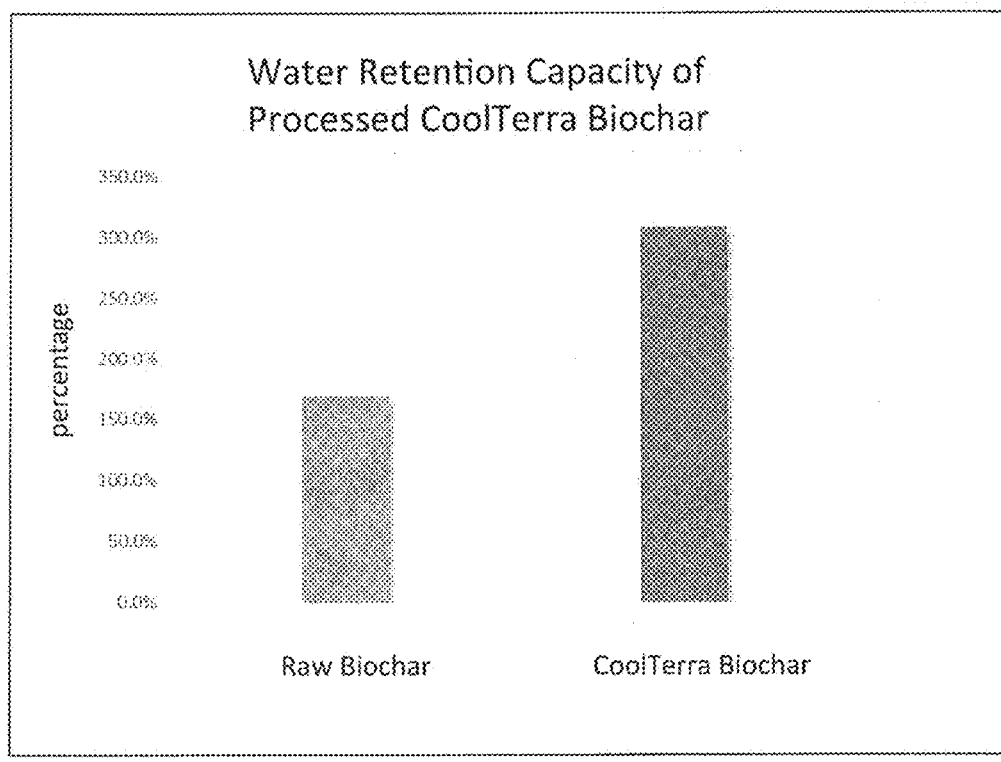
FIG. 7 illustrates the different water retention capacities of raw biochar versus treated biochar measured gravimetrically.

As illustrated in FIG. 7 the treated biochar has an increased water retention capacity over raw biochar of approximately 1.5 times the raw biochar. Similarly, testing of treated biochar derived from pine have also shown an approximate 1.5 times increase in water retention capacity over raw biochar. With certain biochar, the water retention capacity of treated biochar could be as great as three time that of raw biochar.

"Water holding capacity," which may also be referred to as "Water Retention Capacity," is the amount of water that can be held both internally within the porous structure and in the interparticle void spaces in a given batch of particles. While a summary of the method of measure is provided above, a more specific method of measuring water holding capacity/water retention capacity is measured by the following procedure: (i) drying a sample of material under temperatures of 105° C. for a period of 24 hours or using another scientifically acceptable technique to reduce the moisture content of the material to less than 2%, less than 1%; and preferably less than 0.5% (ii) placing a measured amount of dry material in a container; (iii) filling the container having the measured amount of material with water such that the material is completely immersed in the water; (iv) letting the water remain in the container having the measured amount of material for at least ten minutes or treating the material in accordance with the invention by infusing with water when the material is a treated biochar; (v) draining the water from the container until the water ceases to drain; (vi) weighing the material in the container (i.e., wet weight); (vii) again drying the material by heating it under temperatures of 105° C. for a period of 24 hours or using another scientifically acceptable technique to reduce the moisture content of the material to less than 2% and preferably less than 1%; and (viii) weighing the dry material again (i.e., dry weight) and, for purposes of a volumetric measure, determining the volume of the material.

Measured gravimetrically, the water holding/water retention capacity is determined by measuring the difference in weight of the material from step (vi) to step (viii) over the weight of the material from step (viii) (i.e., wet weight-dry weight/dry weight). FIG. 7 illustrates the different water retention capacities of raw biochar versus treated biochar measured gravimetrically. As illustrated, water retention capacity of raw biochar can be less than 200%, whereas treated biochar can have water retention capacities measured gravimetrically greater than 100%, and preferably between 200 and 400%.

Water holding capacity can also be measured volumetrically and represented as a percent of the volume of water retained in the biochar after gravitationally draining the excess water/volume of biochar The volume of water retained in the biochar after draining the water can be determined from the difference between the water added to the container and water drained off the container or from the difference in the weight of the wet biochar from the weight of the dry biochar converted to a volumetric measurement. This percentage water holding capacity for treated biochar may be 30% and above by volume, and preferably 50-55 percent and above by volume.

Given biochar's increased water retention capacity, the application of the treated biochar and even the raw biochar can greatly assist with the reduction of water and/or nutrient application. It has been discovered that these same benefits can be imparted to agricultural growth.

3. Plant Available Water

Figure 8:
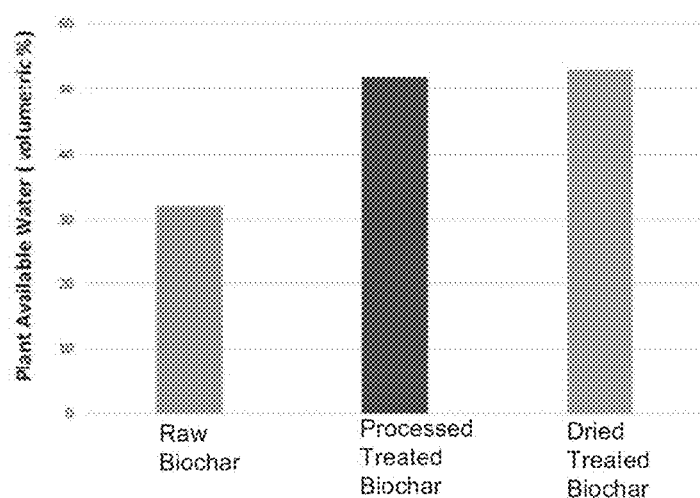
FIG. 8 is a chart showing the plant available water of raw biochar compared to treated biochar (wet and dry).

As illustrated in FIG. 8, plant available water is greatly increased in treated biochar over that of raw biochar. FIG. 8 illustrates the plant available water in raw biochar, versus treated biochar and treated dried biochar and illustrates that treated biochar can have a plant available water percent of greater than 35% by volume.

"Plant Available Water" is the amount of unbound water in the material available for plants to uptake. This is calculated by subtracting the water content at field capacity from the water content at the permanent wilting point, which is the point when no water is available for the plants. Field capacity is generally expressed as the bulk water content retained at −33 J/kg (or −0.33 bar) of hydraulic head or suction pressure. Permanent wilting point is generally expressed as the bulk water content retained at −1500 J/kg (or −15.0 bar) of hydraulic head or suction pressure. Methods for measuring plant available water are well-known in the industry and use pressure plate extractor, which are commercially available or can be built using well-known principles of operation.

4. $H_2O$, ROC, VOC and HOC

Further, the treatment processes are capable of modifying the pore surfaces to remove or neutralize deleterious materials that are otherwise difficult, if not for all practical purpose, impossible to mitigate. For example, heavy metals, transition metals, sodium and phytotoxic organics, polycyclic aromatic hydrocarbons, volatile organic compounds (VOCs), and perhaps other phytotoxins. Thus, by treating the biochar in accordance with the treatment processes set forth and described above, the resulting treated biochar has the majority, more preferably essentially all, and most preferably all, of their pore surfaces modified by the removal, neutralization and both, of one or more deleterious, harmful, potentially harmful material that is present in the starting biochar material.

For example, treatment can reduce the total percentage of residual organic compounds (ROC), including both the percentage of heavy ROCs and percentage of VOCs. Through treatment, the total ROC can be reduced to 0-30% wt. %, percentage heavy ROC content can be reduced to 0-20% wt. % and VOC content can be reduced to less than 5% wt. %.

The percent water, total organic compounds, total light organic compounds (volatiles or VOC) and total heavy organic compounds, as referenced in this application as contained in a biochar particle or particles in a sample may all be measured by thermogravimetric analysis. Thermogravimetric analysis is performed by a Hitachi STA 7200 analyzer or similar piece of equipment under nitrogen flow at the rate of 110 mL/min. The biochar samples are heated for predetermined periods of time, e.g., 20 minutes, at a variety of temperatures between 100 and 950° C. The sample weights are measured at the end of each dwell step and at the beginning and at the end of the experiment. Thermogravimetric analysis of a given sample indicating percentage water in a sample is determined by % mass loss measured between standard temperature and 150 degrees C.

Figure 9:
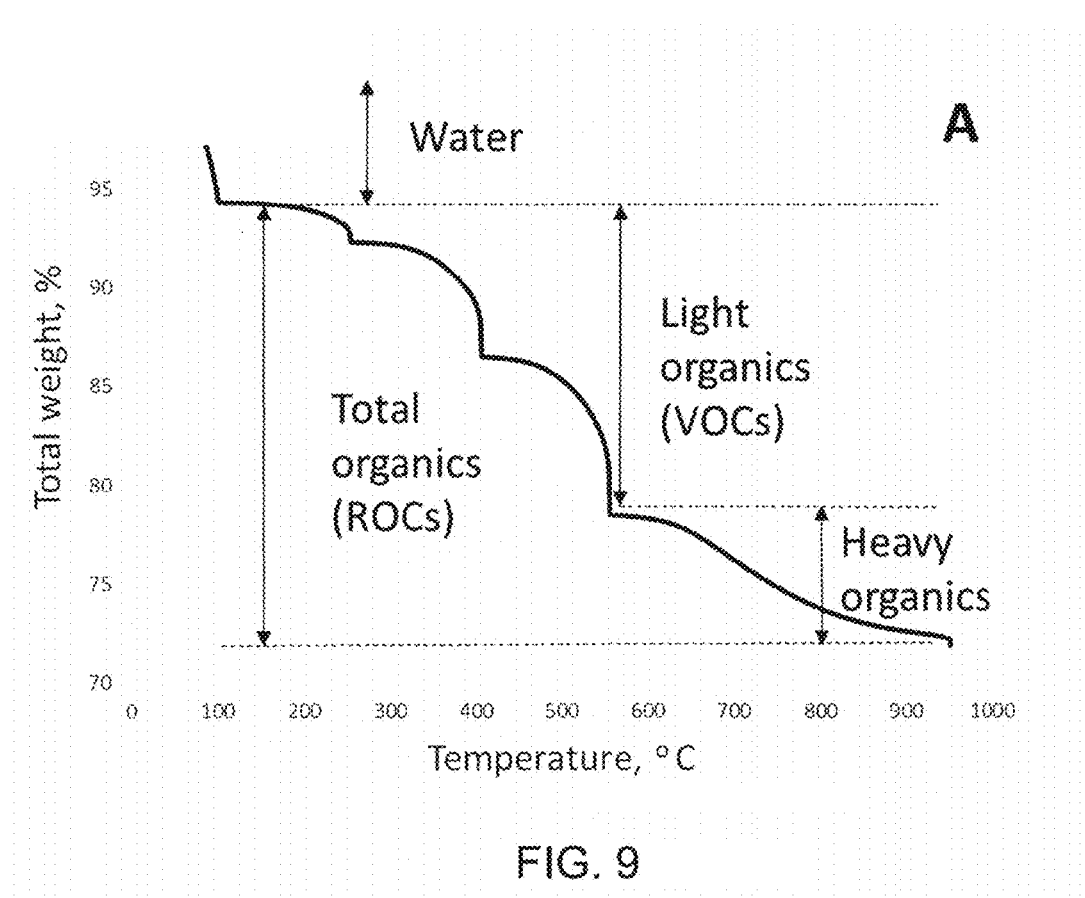
FIG. 9 is a Thermogravimetric Analysis (TGA) plot showing the measurement of water content, heavy organics and light organics in a sample.

Thermogravimetric analysis of a given sample indicating percentage of residual organic compounds is measured by percentage mass loss sustained between 150 degrees C. and 950 degrees C. Thermogravimetric analysis of a given sample indicating percentage of light organic compounds (volatiles) is measured by percentage mass loss sustained between 150 degrees C. and 550 degrees C. Thermogravimetric analysis of a given sample indicating percentage of heavy organic compounds is measured by percentage mass loss sustained between 550 degrees C. and 950 degrees C. FIG. 9 is an example of a Thermogravimetric Analysis (TGA) plot outlining the above explanation and the measure of water, light organics and heavy organics.

In summary, for purposes of this application, "Residual organic compounds" (ROCs) are defined as compounds that burn off during thermogravimetric analysis, as defined above, between 150 degrees C. and 950 degrees C. Residual organic compounds include, but are not limited to, phenols, polyaromatic hydrocarbons, monoaromatic hydrocarbons, acids, alcohols, esters, ethers, ketones, sugars, alkanes and alkenes. Of the ROCs, those that burn off using thermogravimetric analysis between 150 degrees C. and 550 degrees are considered light organic compounds (volatiles or VOCs), and those that burn off between 550 degrees C. and 950 degrees C. are heavy organic compounds. It should be noted that there may be some inorganic compounds which also are burned off during TGA analysis in these temperature ranges, but these are generally a very low percentage of the total emission and can be disregarded in the vast majority of cases as slight variations. In any of these measurements, a gas chromatograph/mass spectrometer may be used if needed for higher degrees of precision.

9. pH

Figure 10:
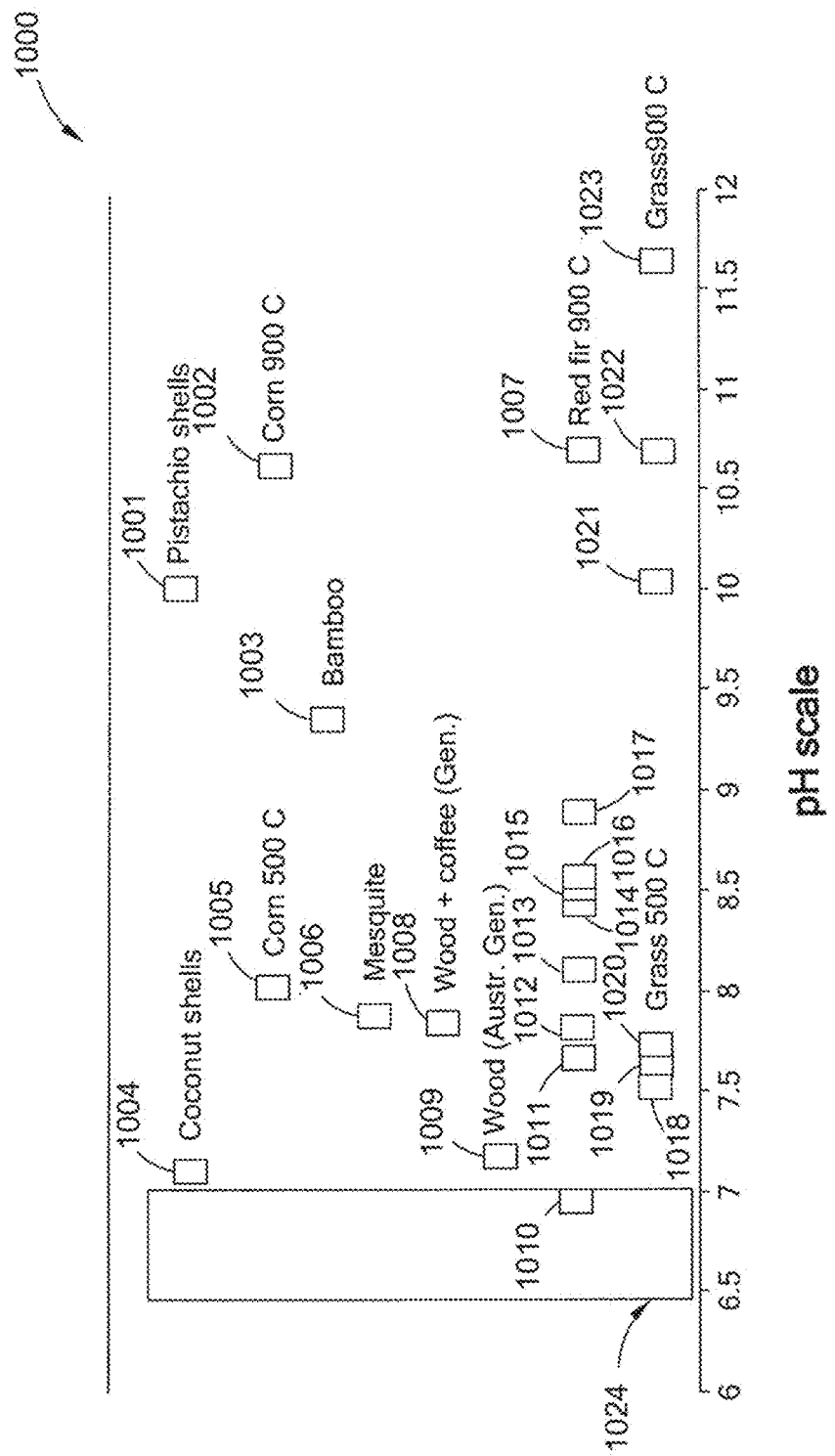
FIG. 10 is a chart showing various pH ranges for raw biochars.
Figure 11:
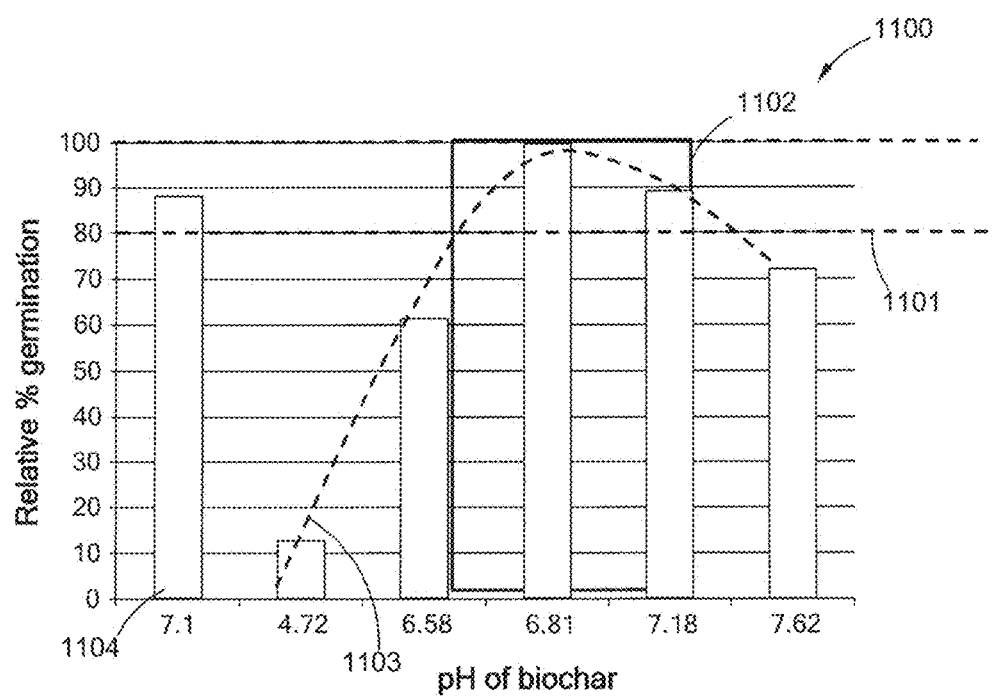
FIG. 11 is a chart showing various pH ranges and germination for treated biochars.

Regarding pH, the above described vacuum infiltration processes and/or surfactant wash processes have the ability to take raw biochars having detrimental or deleterious pHs and transform those biochars into a treated biochar having pH that is in an optimal range for most plant growth, and soil health. FIG. 10 is a graph 1000 showing the pH of various starting biochars that were made from different starting materials and pyrolysis process temperatures, including coconut shells 1004, pistachio shells 1001, corn at 500° C. 1005, corn at 900° C. 1002, bamboo 1003, mesquite 1006, wood and coffee 1008, wood (Australia) 1009, various soft woods 1010, 1011, 1012, 1013, 1014, 1015, 1016, 1017, red fir at 900° C. 1007, various grasses at 500° C. 1018, 1019, 1020, grass 1021, and grass at 900° C. 1023. The vacuum infiltration process, among other processes, can alter the pH from the various undesirable pH levels and bring the pH into the preferred, optimal range 1024 for most plant growth, soil health and combinations of these. FIG. 11 is a chart 1100 showing percentage of germination for plants for particular pHs, and a desired germination range 1101. A control 1104 is compared with an optimal pH range 1102, and a distribution 1103 of growth rates across pHs is shown.

If treated for pH adjustment, the treated biochar takes a few days after treatment for the pH to normalize. Once normalized, tests have proven that pH altered biochar remains at a stable pH, typically lower than the pH of the raw biochar, for up to 12 months or more after treatment.

For example, the treatment process of the present invention can remove and/or neutralize inorganic compounds, such as calcium hydroxide ((CaOH)2), potassium oxide (K2O), magnesium oxide (MgO), magnesium hydroxide (Mg(OH)2), and many others that are formed during pyrolysis, and are fixed to the biochar pore surfaces. These inorganics, in particular calcium hydroxide, adversely affect the biochar's pH, making the pH in some instances as high as 8.5, 9.5, 10.5 and 11.2. These high pH ranges are generally considered to be deleterious, detrimental to many crops, and may kill or adversely affect the plants, sometimes rendering an entire field a loss.

The calcium hydroxide and other inorganics, cannot readily, quickly, and/or effectively be removed at meaningful percentages or quantities by simple washing of the biochar, even in an acid bath. It cannot be removed by drying the biochar, such as by heating, vacuum, or centrifugal force. It is theorized that these techniques and methodologies cannot reach or otherwise affect the various pore surfaces, e.g., macro-, meso- and micro- in any viable or efficacious manner; and thus cannot remove or otherwise neutralize the calcium hydroxide.

Upon modification of the pore surface area by removal and/or neutralization of the calcium hydroxide the pH of the biochar can be reduced to the range of about pH 5 to about pH 8.5, and more preferably from about pH 6.4 to about 7.2, and still more preferably around 6.5 to 6.8, recognizing that other ranges and pHs are contemplated and may prove useful, under specific environmental situations. Thus, the present treated biochars, particles, batches and both, have most, essentially all, and more preferably all, of their pore surfaces modified by the removal, neutralization and both, of the calcium hydroxide that is present in the starting biochar material. These treated biochars have pHs in the range of about 5 to about 8.5, about 6.2 to 7.8, about 6.5 to about 7.5, about 6.4 to about 7, and about 6.8. Prior to and before testing, biochar is passed through a 2 mm sieve before pH is measured. All measurements are taken according to Rajkovich et. al, *Corn growth and nitrogen nutrition after additions of biochars with varying properties to a temperate soil*, Biol. Fertil. Soils (2011), from which the IBI method is based.

There are a wide variety of tests, apparatus and equipment for making pH measurements. For example, and preferably when addressing the pH of biochar, batches, particles and pore surfaces of those particles, two appropriates for measuring pH are the Test Method for the US Composting Council ("TMCC") 4.11-A and the pH Test Method promulgated by the International Biochar Initiative. The test method for the TMCC comprises mixing biochar with distilled water in 1:5 [mass:volume] ratio, e.g., 50 grams of biochar is added to 250 mol f pH 7.0±0.02 water and is stirred for 10 minutes; the pH is then the measured pH of the slurry. The pH Test Method promulgated by the International Biochar Initiative comprises 5 grams of biochar is added to 100 mol f water pH=7.0±0.02 and the mixture is tumbled for 90 minutes; 25 the pH is the pH of the slurry at the end of the 90 minutes of tumbling.

10. Pore Volume

Generally, a treated biochar sample has greater than 50% by volume of its porosity in macropores (pores greater than 300 nanometers). Further, results indicate that greater than 75% of pores in treated biochar are below 50,000 nanometers. Also, results indicate that greater than 50% by volume of treated biochar porosity are pores in the range of 500 nanometers and 100,000 nanometers. Bacterial sizes are typically 500 nanometers to several thousand nanometers. Bacteria and other microbes have been observed to fit and colonize in the pores of treated biochar, thus supporting the pore size test results.

Macropore volume is determined by mercury porosimetry, which measures the meso and/or macro porosity by applying pressure to a sample immersed in mercury at a pressure calibrated for the minimum pore diameter to be measured (for macroporosity this is 300 nanometers). This method can be used to measure pores in the range of 3 nm to 360,000 nm. Total volume of pores per volumetric unit of substance is measured using gas expansion method.

Depending upon the biomass from which the biochar is derived, mercury porosimetry testing has shown that washing under differential pressure, using the processes described above, can increase the number of both the smallest and larger pores in certain biochar (e.g., pine) and can increase the number of usable smaller pores. Treatment of biochar using either vacuum or surfactant does alter the percentage of total usable pores between 500 to 100,000 nanometers and further has varying impact on pores less than 50,000 nanometers and less than 10,000 nanometers.

Figure 29:
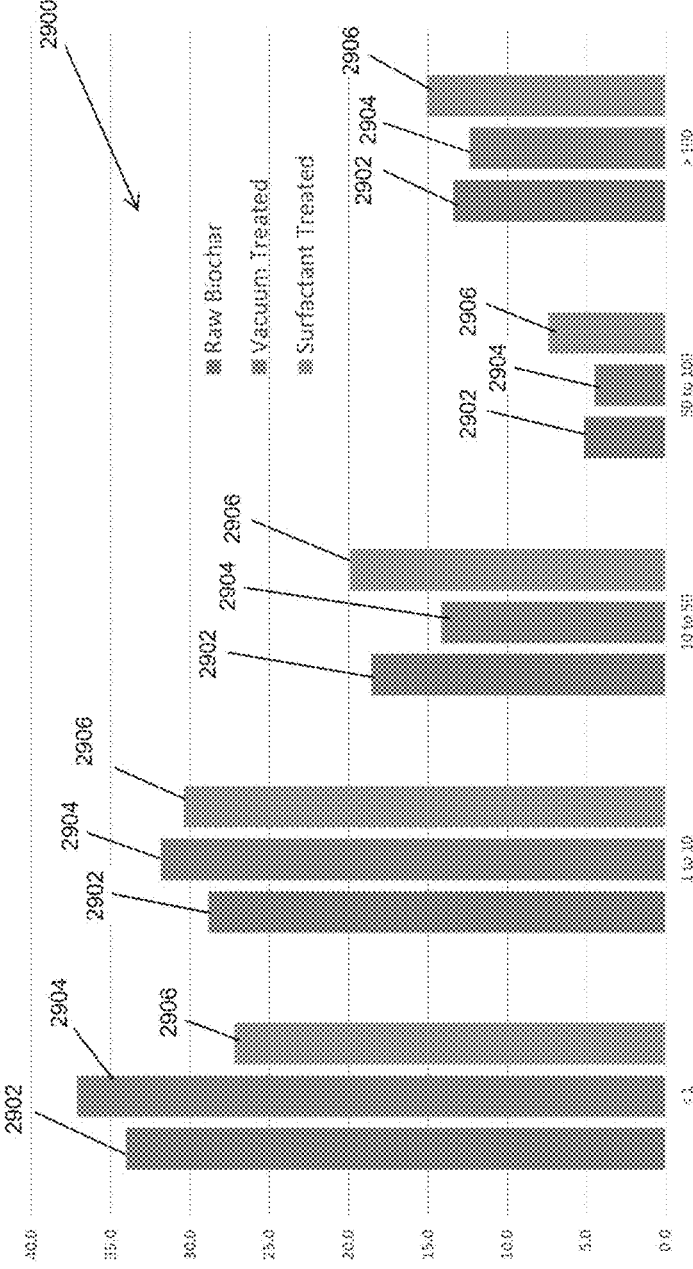
FIG. 29 is a chart showing the impact of treatment on pores sizes of biochar derived from coconut.

FIG. 29 is a chart 2900 showing the impact of treatment on pores sizes of biochar derived from coconut. The majority of the coconut based biochar pores are less than 10 microns. Many are less than 1 micron. Vacuum processing of the biochar results in small reduction of 10 to 50 micron pores, with increase of smaller pores on vacuum processing. The mercury porosimetry results of the raw biochar are represented by 2902 (first column in the group of three). The vacuum treated biochar is represented by 2904 (second column in the group of three) and the surfactant treated biochar is 2906 (third column in the group of three).

Figure 30:
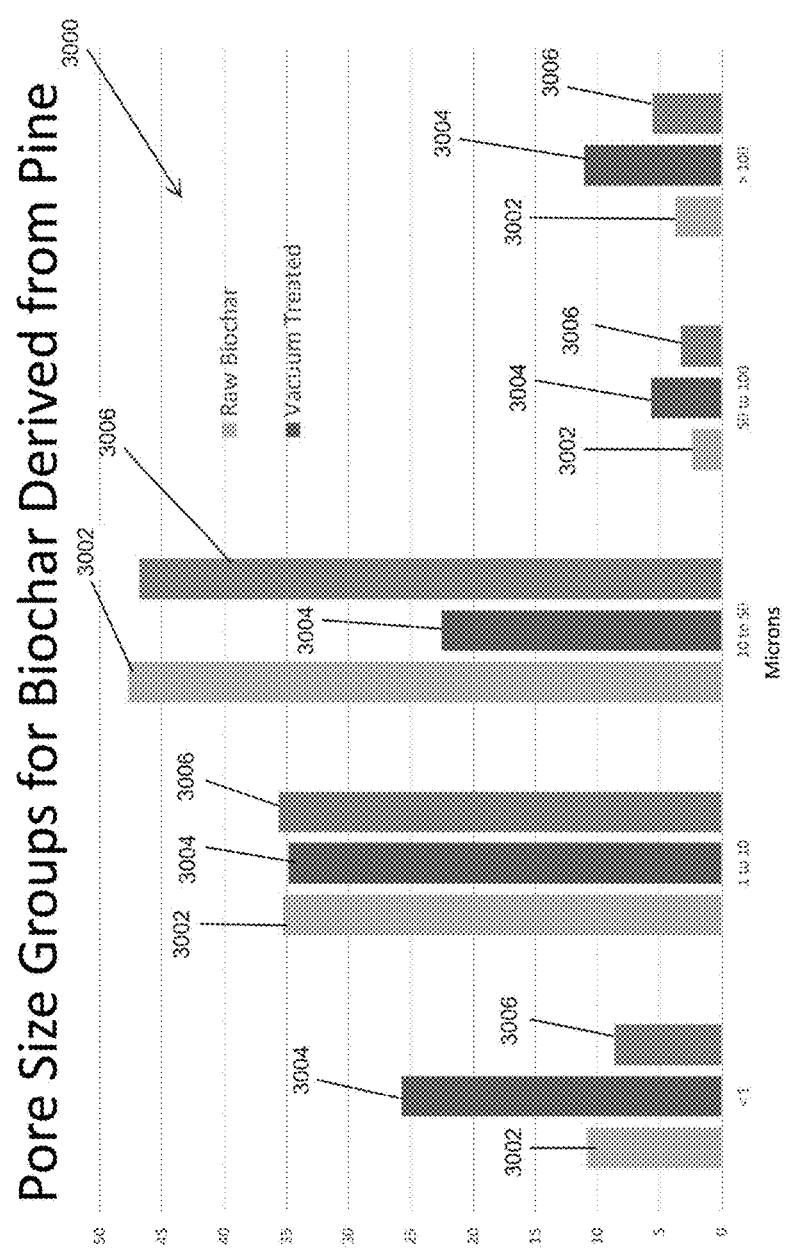
FIG. 30 is a chart showing the impact of treatment on pores sizes of biochar derived from pine.

FIG. 30 is a chart 3000 showing the impact of treatment on pores sizes of biochar derived from pine. The majority of the pine based biochar pores are 1 to 50 microns, which is a good range for micro-biologicals. Vacuum processing results in significant reduction of the 10 to 50 micron pores, with an increase of smallest and largest pores. The mercury porosimetry results of the raw biochar are represented by 3002 (first column in the group of three). The vacuum treated biochar is represented by 3004 (second column in the group of three) and the surfactant treated biochar is 3006 (third column in the group of three).

10. Bulk Density

A batch of biochar has a bulk density, which is defined as weight in grams (g) of 1 cm3 of loosely poured material that has or retains some free space between the particles. The biochar particles in this batch will also have a solid density, which is the weight in grams (g) of 1 cm3 of just particles, i.e., with the free space between the particles removed. The solid density includes the air space or free space that is contained within the pores, but not the free space between particles. The actual density of the particles is be the density of the material in grams (g) of 1 cm3 of material, which makes up the biochar particles, i.e., the particle material with pore volume removed.

In general, as bulk density increases the pore volume would be expected to decrease and with it, the ability to hold infiltrate, e.g., inoculant. Thus, with the infiltration processes, the treated biochars can have impregnation capacities that are larger than could be obtained without infiltration, e.g., the treated biochars can readily have 30%, 40%, 50%, or most preferably, 60%-100% of their total pore volume filled with an infiltrate, e.g., an inoculant. The impregnation capacity is the amount of a liquid that a biochar particle, or batch of particles, can absorb. The ability to make the pore morphology hydrophilic, and to infuse liquid deep into the pore structure through the application of positive or negative pressure and/or a surfactant, alone or in combination, provides the ability to obtain these high impregnation capabilities. The treated biochars can have impregnation capacities, i.e., the amount of infiltrate that a particle can hold on a volume held/total volume of a particle basis that is greater than 0.2 cm3/cm3 to 0.8 cm3/cm3.

Resulting bulk densities of treated biochar can range from 0.1-0.6 $g/cm^3$ and sometimes preferably between 0.3-0.6 $g/cm^3$ and can have solid densities ranging from 0.2-1.2 $g/cm^3$.

11. Remaining Water Content

Figure 12:
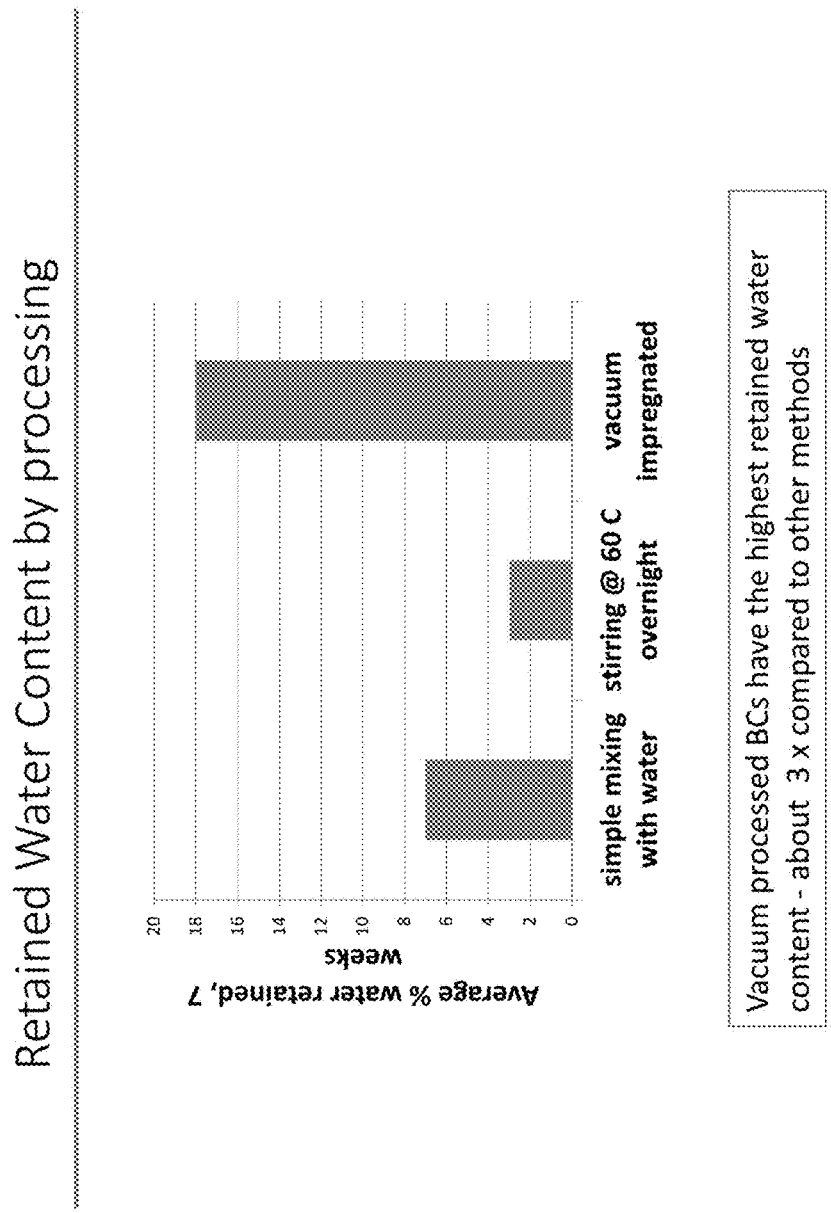
FIG. 12 is a chart showing the retained water in vacuum impregnated biochar over other biochars after a seven week period.

Treated biochar of the present invention has also demonstrated the ability to retain more water than raw biochar after exposure to the environment for defined periods of time. For purposes of this application "remaining water content" can be defined as the total amount of water that remains held by the biochar after exposure to the environment for certain amount of time. Exposure to environment is exposure at ambient temperature and pressures. Under this definition, remaining water content can be may be measured by (i) creating a sample of biochar that has reached its maximum water holding capacity; (ii) determining the total water content by thermogravimetric analysis (H2O (TGA)), as described above on a sample removed from the output of step (i) above, (iii) exposing the biochar in the remaining sample to the environment for a period of 2 weeks (15 days, 360 hrs.); (iv) determining the remaining water content by thermogravimetric analysis (H2O (TGA)); and (v) normalizing the remaining (retained) water in mL to 1 kg or 1 L biochar. The percentage of water remaining after exposure for this two-week period can be calculated by the remaining water content of the biochar after the predetermine period over the water content of the biochar at the commencement of the two-week period. Using this test, treated biochar has shown to retain water at rates over 4× that of raw biochar. Testing has further demonstrated that the following amount of water can remain in treated biochar after two weeks of exposure to the environment: 100-650 mL/kg; 45-150 mL/L; 12-30 gal/ton; 3-10 gal/yd3 after 360 hours (15 days) of exposure to the environment. In this manner, and as illustrated in FIG. 12, biochar treated through vacuum impregnation can increase the amount of retained water in biochar about 3× compared to other methods even after seven weeks. In general, the more porous and the higher the surface area of a given material, the higher the water retention capacity. Further, it is theorized that by modifying the hydrophilicity/hydrophobicity of the pore surfaces, greater water holding capacity and controlled release may be obtained. Thus, viewed as a weight percent, e.g., the weight of retained water to weight of biochar, examples of the present biochars can retain more than 5% of their weight, more than 10% of their weight, and more than 15% of their weight, and more compared to an average soil which may retain 2% or less, or between 100-600 ml/kg by weight of biochar Tests have also shown that treated biochars that show weight loss of >1% in the interval between 43-60° C. when analyzed by the Thermal Gravimetric Analysis (TGA) (as described below) demonstrate greater water holding and content capacities over raw biochars. Weight loss of >5%-15% in the interval between 38-68° C. when analyzed by the Thermal Gravimetric Analysis (TGA) using sequences of time and temperature disclosed in the following paragraphs or others may also be realized. Weight percentage ranges may vary from between >1%-15% in temperature ranges between 38-68° C., or subsets thereof, to distinguish between treated biochar and raw biochar.

Figure 13:
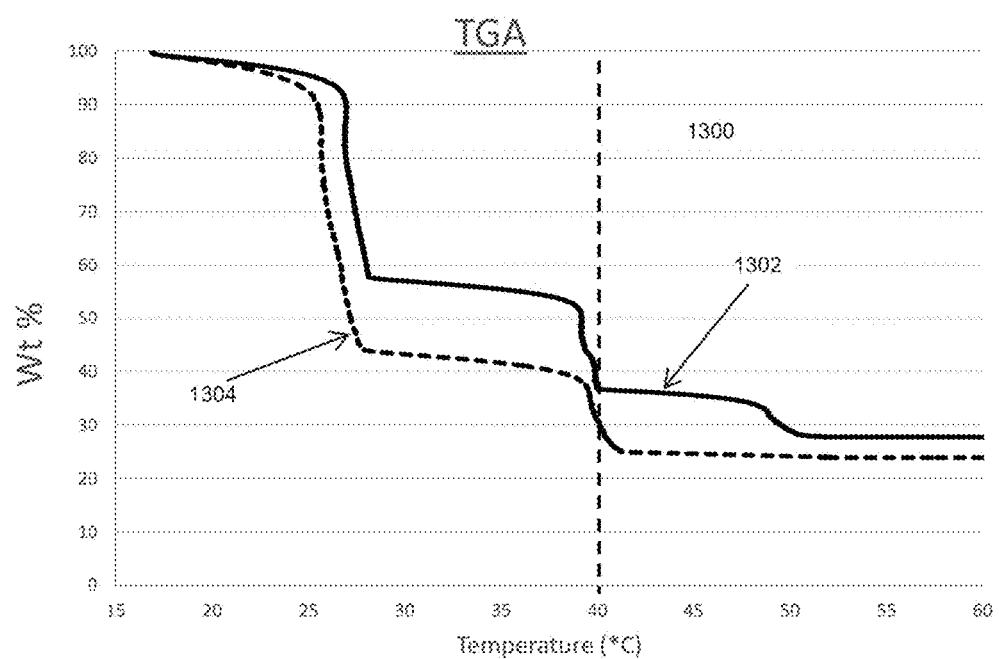
FIG. 13 is a chart showing the weight loss of treated biochars verses raw biochar samples when heated at varying temperatures using a TGA testing method.

FIG. 13 is a chart 1300 showing the weight loss of treated biochars 1302 verses raw biochar samples 1304 when heated at varying temperatures using the TGA testing described below. As illustrated, the treated biochars 1302 continue to exhibit weight loss when heated between 40-60° C. when analyzed by the Thermal Gravimetric Analysis (TGA) (described below), whereas the weight loss in raw biochar 1304 between the same temperature ranges levels off. Thus, testing demonstrates the presence of additional moisture content in treated biochars 1302 versus raw biochars 1304.

In particular, the treated biochars 1302 exhibit substantial water loss when heated in inert gas such as nitrogen. More particularly, when heated for 25 minutes at each of the following temperatures 20, 30, 40, 50 and 60 degrees Celsius, ° C. the treated samples lose about 5-% to 15% in the interval 43-60° C. and upward of 20-30% in the interval between 38-68° C. The samples to determine the water content of the raw biochar were obtained by mixing a measured amount of biochar and water, stirring the biochar and water for 2 minutes, draining off the water, measuring moisture content and then subjecting the sample to TGA. The samples for the treated biochar were obtained by using the same measured amount of biochar as used in the raw biochar sample, and impregnating the biochar under vacuum. Similar results are expected with biochar treated with a treatment process consistent with those described in this disclosure with the same amount of water as used with the raw biochar. The moisture content is then measured and the sample is subjected to TGA described above.

The sequences of time and temperature conditions for evaluating the effect of biochars heating in inert atmosphere is defined in this application as the "Bontchev-Cheyne Test" ("BCT"). The BCT is run using samples obtained, as described above, and applying Thermal Gravimetric Analysis (TGA) carried out using a Hitachi STA 7200 analyzer under nitrogen flow at the rate of 110 mL/min. The biochar samples are heated for 25 minutes at each of the following temperatures: 20, 30, 40, 50 and 60° C. The sample weights are measured at the end of each dwell step, at the beginning and at the end of the experiment. The analyzer also continually measures and records weight over time. Biochars having enhanced water holding or retention capacities are those that exhibit weight loss of >5% in the interval between 38-68° C., >1% in the interval between 43-60° C. Biochars with greater water holding or retention capacities can exhibit >5% weight loss in the interval between 43-60° C. measured using the above described BCT.

12. Electrical Conductivity

The electrical conductivity (EC) of a solid material-water mixture indicates the amount of salts present in the solid material. Salts are essential for plant growth. The EC measurement detects the amount of cations or anions in solution; the greater the amount of ions, the greater the EC. The ions generally associated with salinity are $Ca^{2+}$, $Mg^{2+}$, $K^+$, $Na^+$, $H^+$, $NO_3^-$, $SO_4^{2-}$, $Cl^-$, $HCO_3^-$, $OH^-$. Electrical conductivity testing of biochar was done following the method outlined in the USDA's Soil Quality Test Kit Guide and using a conventional EC meter. The biochar sample is mixed with DI water in a 1:1 biochar to water ratio on a volume basis. After thorough mixing, the EC (dS/m) is measured while the biochar particles are still suspended in solution. Testing of treated biochar shows its EC is generally greater than 0.2 dS/m and sometimes greater than 0.5 dS/m.

13. Cation Exchange Capacity

One method for cation exchange capacity ("CEC") determination is the use of ammonium acetate buffered at pH 7.0 (see Schollenberger, C. J. and Dreibelbis, E R. 1930, *Analytical methods in base-exchange investigations on soils*, Soil Science, 30, 161-173). The material is saturated with 1M ammonium acetate, ($NH_4OAc$), followed by the release of the $NH_4^+$ ions and its measurement in meq/100 g (milliequivalents of charge per 100 g of dry soil) or cmolc/kg (centimoles of charge per kilogram of dry soil). Instead of ammonium acetate another method uses barium chloride according to Mehlich, 1938, *Use of triethanolamine acetate-barium hydroxide buffer for the determination of some base exchange properties and lime requirement of soil*, Soil Sci. Soc. Am. Proc. 29:374-378. 0.1 M $BaCl_2$ is used to saturate the exchange sites followed by replacement with either $MgSO_4$ or $MgCl_2$.

Indirect methods for CEC calculation involves the estimation of extracted $Ca_2^+$, $Mg_2^+$, $K^+$, and $Na^+$ in a standard soil test using Mehlich 3 and accounting for the exchangeable acidity (sum of $H^+$, $Al_3^+$, $Mn_2^+$, and $Fe_2^+$) if the pH is below 6.0 (see Mehlich, A. 1984, *Mehlich-3 soil test extractant: a modification of Mehlich-2 extractant*, Commun. Soil Sci. Plant Anal. 15(12): 1409-1416). When treated using the above methods, including but not limited by washing under a vacuum, treated biochars generally have a CEC greater than 5 millieq/l and some even have a CEC greater than 25 (millieq/l).

14. Anion Exchange Capacity

Similar to CEC measurements, anion exchange capacity ("AEC") may be calculated directly or indirectly-saturated paste extraction of exchangeable anions, $Cl^-$, $NO_3^-$, $SO_4^{2-}$, and $PO4^{3-}$ to calculate anion sum or the use of potassium bromide to saturate anions sites at different pHs and repeated washings with calcium chloride and final measurement of bromide (see Rhoades, J. D. 1982, *Soluble salts*, p. 167-179. In: A. L. Page et al. (ed.) Methods of soil analysis: Part 2: Chemical and microbiological properties; and Michael Lawrinenkoa and David A. Laird, 2015, *Anion exchange capacity of biochar*, Green Chem., 2015, 17, 4628-4636). When treated using the above methods, including but not limited by washing under a vacuum, treated biochar generally have an AEC greater than 5 milliq/l and some even have an AEC greater than 20 (millieq/l).

15. Dioxins TEQ

As noted above, treatment can remove or neutralize heavy metals, transition metals, sodium and phytotoxic organics, polycyclic aromatic hydrocarbons, volatile organic compounds (VOCs), other phytotoxins, and even dioxins. Thus, by treating the biochar in accordance with the treatment processes set forth and described above, the resulting treated biochar has essentially all, and more preferably all, of their pore surfaces modified by the removal, neutralization and both, of one or more deleterious, harmful, potentially harmful material that is present in the starting biochar material.

Dioxins may also be removed through the treatment processes of the present invention. Dioxins are released from combustion processes and thus are often found in raw biochar. Dioxins include polychlorinated dibenzo-p-dioxins (PCDDs) (i.e., 75 congeners (10 are specifically toxic)); polychlorinated dibenzofurans (PCDFs) (i.e., 135 congeners (7 are specifically toxic)) and polychlorinated biphenyls (PCBs) (Considered dioxin-like compounds (DLCs)).

Since some dioxins may be carcinogenic even at low levels of exposure over extended periods of time, the FDA views dioxins as a contaminant and has no tolerances or administrative levels in place for dioxins in animal feed. Dioxins in animal feed can cause health problems in the animals themselves. Additionally the dioxins may accumulate in the fat of food-producing animals and thus consumption of animal derived foods (e.g. meat, eggs, milk) could be a major route of human exposure to dioxins. Thus, if biochar is used in animal applications, where the animals ingest the biochar, the ability to remove dioxins from the raw biochar prior to use is of particular significance.

For example, to remove dioxins from raw biochar, the biochar may, in accordance with one implementation of invention, be washed with water by pulling a vacuum on the biochar, ranging from approximately 5-30" Hg for a period of less than 10 minutes. Results have proven to remove dioxins from raw biochar by applying the treatment process of the present invention. To demonstrate the removal of dioxins, samples of both raw biochar and treated biochar, derived from coconut and treated within the parameters set forth above, were sent out for testing. The results revealed that the dioxins in the raw biochar were removed through treatment as the dioxins detected in the raw biochar sample were not detected in the treated biochar sample. Below is a chart comparing the test results of measured dioxins in the raw verses the treated biochar.

| Dioxins | Amount Detected in Raw Biochar Sample | Amount Detected in Treated Biochar Sample |
|---|---|---|
| Tetradioxins | 26.4 ng/Kg-dry | Not detectable |
| Pentadioxins | 5.86 ng/Kg-dry | Not detectable |
| Hexadioxins | 8.41 ng/Kg-dry | Not detectable |

A number of different dioxins exist, several of which are known to be toxic or undesirable for human consumption. Despite the test results above, it is possible that any number of dioxins could be present in raw biochar depending on the biomass or where the biomass is grown. It is shown, however, in the above testing, that the treatment process of the present invention can be used to eliminate dioxins present in raw biochar.

Seventeen tetra-octo dioxins and furan congeners are the basis for regulatory compliance. Other dioxins are much less toxic. Dioxins are generally regulated on toxic equivalents (TEQ) and are represented by the sum of values weighted by Toxic Equivalency Factor (TEF)

$$TEQ = \Sigma [C_i] \times TEF_i$$

2,3,7,8-TCDD has a TEF of 1 (most toxic). TEQ is measured as ng/kg WHO-PCDD/F-TEQ//kg NDs are also evaluated. Two testing methods are generally used to determine TEQ values: EPA Method 8290 (for research and understanding at low levels (ppt-ppq); and EPA Method 1613B (for regulatory compliance). Both are based on high resolution gas chromatography (HRGC)/high resolution mass spectrometry (HRMS).

The required EU Feed Value is equal to or less than 0.75 ng/kg WHO-PCDD/F-TEQ//kg. Treated biochar, in accordance with the present invention, has shown to have TEQ dioxins less than 0.5 ng/kg WHO-PCDD/F-TEQ//kg, well below the requirement for EU Feed limits of 0.75 ng/kg WHO-PCDD/F-TEQ//kg. As further set forth above, treatment can reduce the amount of detectable dioxins from raw biochar such that the dioxins are not detectible in treated biochar. Two methods are used: EPA Method 8290 (for research and understanding at low levels (ppt-ppq); and EPA Method 1613B (for regulatory compliance). Both are based on high resolution gas chromatography (HRGC)/high resolution mass spectrometry (HRMS).

16. Hydrophilicity/Hydrophobicity

The ability to control the hydrophilicity of the pores provides the ability to load the biochar particles with larger volumes of inoculant. The more hydrophilic the more the biochars can accept inoculant or infiltrate. Test show that biochar treated in accordance with the above processes, using either vacuum or surfactant treatment processes increase the hydrophilicity of raw biochar. Two tests may be used to test the hydrophobicity/hydrophilicity of biochar: (i) the Molarity of Ethanol Drop ("MED") Test; and (ii) the Infiltrometer Test.

The MED test was originally developed by Doerr in 1998 and later modified by other researchers for various materials. The MED test is a timed penetration test that is noted to work well with biochar soil mixtures. For 100% biochar, penetration time of different mixtures of ethanol/water are noted to work better. Ethanol/Water mixtures verses surface tension dynes were correlated to determine whether treated biochar has increased hydrophilicity over raw biochar. Seven mixtures of ethanol and deionized water were used with a sorption time of 3 seconds on the biochar.

Seven solutions of deionized ("DI") water with the following respective percentages of ethanol: 3, 5, 11, 13, 18, 24 and 36, were made for testing. The test starts with a mixture having no DI. If the solution is soaked into the biochar in 3 seconds for the respective solution, it receives the corresponding Hydrophobicity Index value below.

| Ethanol % | Hydrophobicity Index | |
|---|---|---|
| 0: DI Water | 0 | Very Hydrophillic |
| 3% | 1 | |
| 5% | 2 | |
| 11% | 3 | |
| 13% | 4 | |
| 18% | 5 | |
| 24% | 6 | |
| 36% | 7 | Strongly Hydrophobic |

To start the test the biochar ("material/substrate") is placed in convenient open container prepared for testing. Typically, materials to be tested are dried 110° C. overnight and cooled to room temperature. The test starts with a deionized water solution having no ethanol. Multiple drips of the solution are then laid onto the substrate surface from low height. If drops soak in less than 3 seconds, test records substrate as "0". If drops take longer than 3 seconds or don't soak in, go to test solution 1. Then, using test solution 1, multiple drops from dropper are laid onto the surface from low height. If drops soak into the substrate in less than 3 seconds, test records material as "1". If drops take longer than 3 seconds, or don't soak in, go to test solution 2. Then, using test solution 2, multiple drops from dropper laid onto the surface from low height. If drops soak into the substrate in less than 3 seconds, test records material as "2". If drops take longer than 3 seconds, or don't soak in, go to test solution 3. Then, using test solution 3, multiple drops from dropper laid onto the surface from low height. If drops soak into the substrate in less than 3 seconds, test records material as "3". If drops take longer than 3 seconds, or don't soak in, go to solution 4.

The process above is repeated, testing progressively higher numbered MED solutions until the tester finds the solution that soaks into the substrate in 3 seconds or less. The substrate is recorded as having that hydrophobicity index number that correlates to the solution number assigned to it (as set forth in the chart above).

Example test results using the MED test method is illustrated below.

| MATERIAL | HYDROPHOBICITY INDEX |
|---|---|
| Raw Pine Biochars | 3 to 5 |
| Surfactant Treated Pine Biochar | 1 |

| MATERIAL | HYDROPHOBICITY INDEX |
| --- | --- |
| Dried Raw Coconut Biochar | 3 |
| Dried Vacuum Treated Coconut Biochar | 3 |
| Dried Surfactant Treated Coconut Biochar | 1 |

Another way to measure and confirm that treatment decreases hydrophobicity and increases hydrophilicity is by using a mini disk infiltrometer. For this test procedure, the bubble chamber of the infiltrometer is filled three quarters full with tap water for both water and ethanol sorptivity tests. Deionized or distilled water is not used. Once the upper chamber is full, the infiltrometer is inverted and the water reservoir on the reserve is filled with 80 mL. The infiltrometer is carefully set on the position of the end of the mariotte tube with respect to the porous disk to ensure a zero suction offset while the tube bubbles. If this dimension is changed accidentally, the end of the mariotte tube should be reset to 6 mm from the end of the plastic water reservoir tube. The bottom elastomer is then replaced, making sure the porous disk is firmly in place. If the infiltrometer is held vertically using a stand and clamp, no water should leak out.

The suction rate of 1 cm is set for all samples. If the surface of the sample is not smooth, a thin layer of fine biochar can be applied to the area directly underneath the infiltrometer stainless steel disk. This ensures good contact between the samples and the infiltrometer. Readings are then taken at 1 min intervals for both water and ethanol sorptivity test. To be accurate, 20 mL water or 95% ethanol needs to be infiltrated into the samples. Record time and water/ethanol volumes at the times are recorded.

The data is then processed to determine the results. The data is processed by the input of the volume levels and time to the corresponding volume column. The following equation is used to calculate the hydrophobicity index of R $$I = at + b\sqrt{t}$$

a: Infiltration Rate, cm/s
b: Sorptivity, cm/s$^{1/2}$ $$R = 1.95 * \frac{b_{ethanol}}{b_{water}}$$

Figure 14:
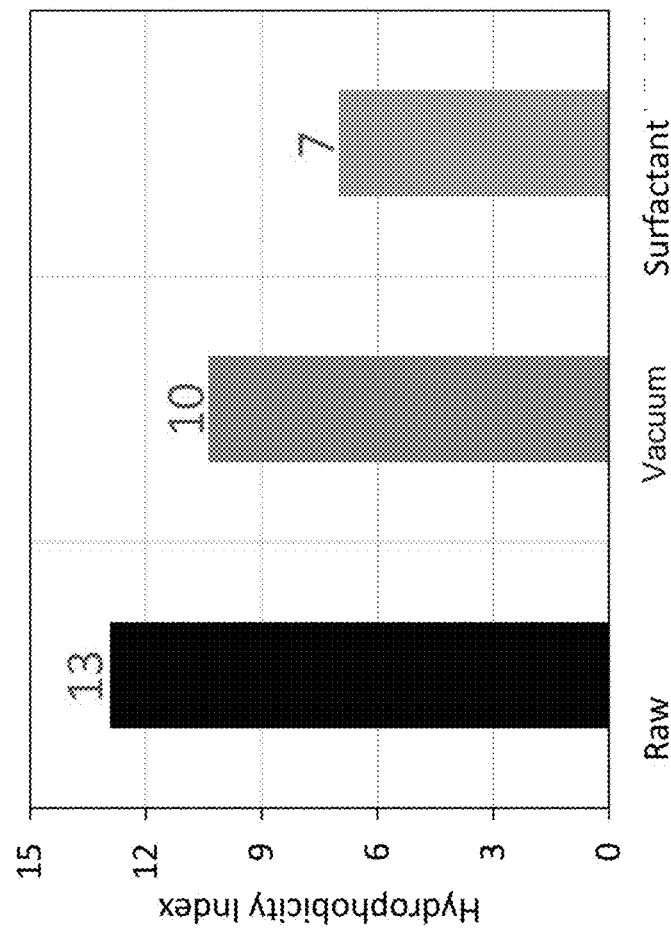
FIG. 14 is a chart showing the measured hydrophobicity index raw biochar, vacuum treated biochar and surfactant treated biochar.

FIG. 14 illustrates one example of the results of a hydrophobicity test performed on raw biochar, vacuum treated biochar and surfactant treated biochar. As illustrated, both the vacuum treated and surfactant treated biochar are more hydrophilic than the raw biochar based upon the lower Index rating. In accordance with the test data in FIG. 14, the hydrophobicity of raw biochar was reduced 23% by vacuum processing and 46% by surfactant addition.

As an example, raw biochar and treated biochar were tested with ethanol and water, five times for each. The results below on a coconut based biochar show that the hydrophobicity index of the treated biochar is lower than the raw biochar. Thus, tests demonstrate that treating the biochar, using the methods set forth above, make the biochar less hydrophobic and more hydrophilic.

| MATERIAL | HYDROPHOBICITY INDEX |
| --- | --- |
| Dried Raw Biochar | 12.9 |
| Dried Vacuum Treated Biochar | 10.4 |
| Dried Surfactant Treated Biochar | 7.0 |
| As Is Raw Biochar | 5.8 |
| As Is Vacuum Treated Biochar | 2.9 |

Further, through the treatment processes of the present invention, the biochar can also be infused with soil enhancing agents. By infusing liquid into the pore structure through the application of positive or negative pressure and/or a surfactant, alone or in combination, provides the ability to impregnate the macropores of the biochar with soil enhancing solutions and solids. The soil enhancing agent may include, but not be limited to, any of the following: water, water solutions of salts, inorganic and organic liquids of different polarities, liquid organic compounds or combinations of organic compounds and solvents, mineral and organic oils, slurries and suspensions, supercritical liquids, fertilizers, plant growth promoting rhizobacteria, free-living and nodule-forming nitrogen fixing bacteria, organic decomposers, nitrifying bacteria, phosphate solubilizing bacteria, biocontrol agents, bioremediation agents, saprotrophic fungi, ectomycorrhizae and endomycorrhizae, among others.

D. Impregnation and/or Inoculation with Infiltrates or Additives

In addition to mitigating or removing deleterious pore surface properties, by treating the pores of the biochar through a forced, assisted, accelerate or rapid infiltration process, such as those described above, the pore surface properties of the biochar can be enhanced. Such treatment processes may also permit subsequent processing, may modify the pore surface to provide predetermined properties to the biochar, and/or provide combinations and variations of these effects. For example, it may be desirable or otherwise advantageous to coat substantially all, or all of the biochar macropore and mesopore surfaces with a surface modifying agent or treatment to provide a predetermined feature to the biochar, e.g., surface charge and charge density, surface species and distribution, targeted nutrient addition, magnetic modifications, root growth facilitator, and water absorptivity and water retention properties.

By infusing liquids into the pores of biochar, it has been discovered that additives infused within the pores of the biochar provide a time release effect or steady flow of some beneficial substances to the root zones of the plants and also can improve and provide a more beneficial environment for microbes which may reside or take up residence within the pores of the biochar. In particular, additive infused biochars placed in the soil prior to or after planting can dramatically reduce the need for high frequency application of additives, minimize losses caused by leaching and runoff and/or reduce or eliminate the need for controlled release fertilizers. They can also be exceptionally beneficial in animal feed applications by providing an effective delivery mechanism for beneficial nutrients, pharmaceuticals, enzymes, microbes, or other substances.

Figure 15:
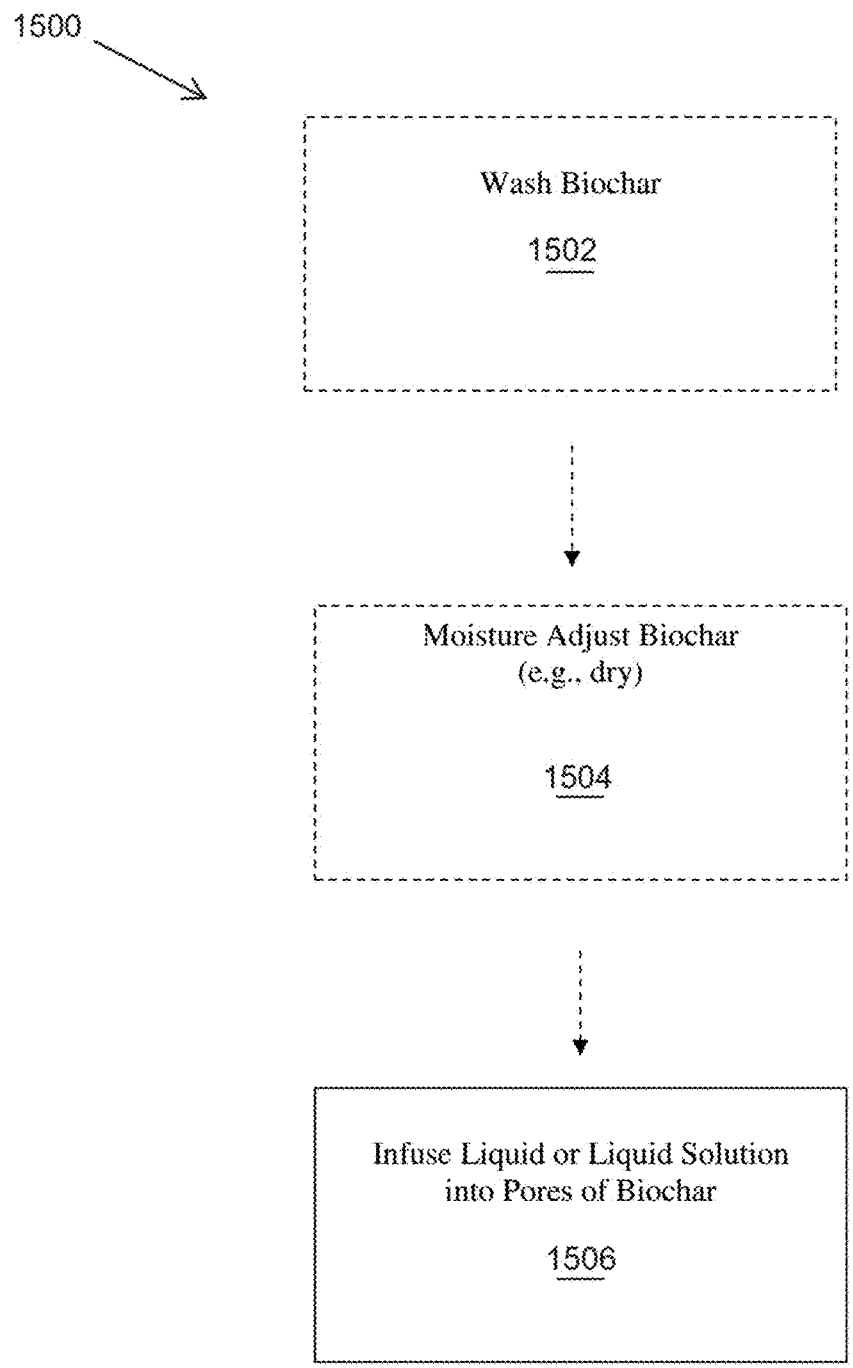
FIG. 15 is a flow diagram showing one example of a method for infusing biochar.

For purposes of this application, "infusion" of a liquid or liquid solution into the pores of the biochar means the introduction of the liquid or liquid solution into the pores of the biochar by a means other than solely contacting the liquid or solution with the biochar, e.g., submersion. The infusion process, as described in this application in connection with the present invention, includes a mechanical, chemical or physical process that facilitates or assist with the penetration of liquid or solution into the pores of the biochar, which process may include, but not be limited to, positive and negative pressure changes, such as vacuum infusion, surfactant infusion, or infusion by movement of the liquid and/or biochar (e.g., centrifugal force, steam and/or ultrasonic waves) or other method that facilitates, assists, forces or accelerates the liquid or solution into the pores of the biochar. Prior to infusing the biochar, the biochar, as described in detail above, may be washed and/or moisture adjusted. FIG. 15 is a flow diagram 1500 of one example of a method for infusing biochar with an additive. Optionally, the biochar may first be washed or treated at step 1502, the wash may adjust the pH of the biochar, as described in more detail above, or may be used to remove elemental ash and other harmful organics that may be unsuitable for the desired infused fertilizer. Optionally, the moisture content of the biochar may then be adjusted by drying the biochar at step 1504, also as described in further detail above, prior to infusion of the additive or inoculant at step 1506.

In summary, the infusion process may be performed with or without any washing, prior pH adjustment or moisture content adjustment. Optionally, the infusion process may be performed with the wash and/or the moisture adjustment step. All the processes may be completed alone or in the conjunction with one or more of the others.

Through the above process of infusing the additive into the pores of the biochar, the pores of the biochar may be filled by 25%, up to 100%, with an additive solution, as compared to 1-20% when the biochar is only submerged in the solution or washed with the solution for a period of less than twelve hours. Higher percentages may be achieved by washing and/or drying the pores of the biochar prior to infusion.

Data have been gathered from research conducted comparing the results of soaking or immersion of biochar in liquid versus vacuum impregnation of liquid into biochar. These data support the conclusion that vacuum impregnation provides greater benefits than simple soaking and results in a higher percentage volume of moisture on the surface, interstitially and in the pores of the biochar.

Figure 16:
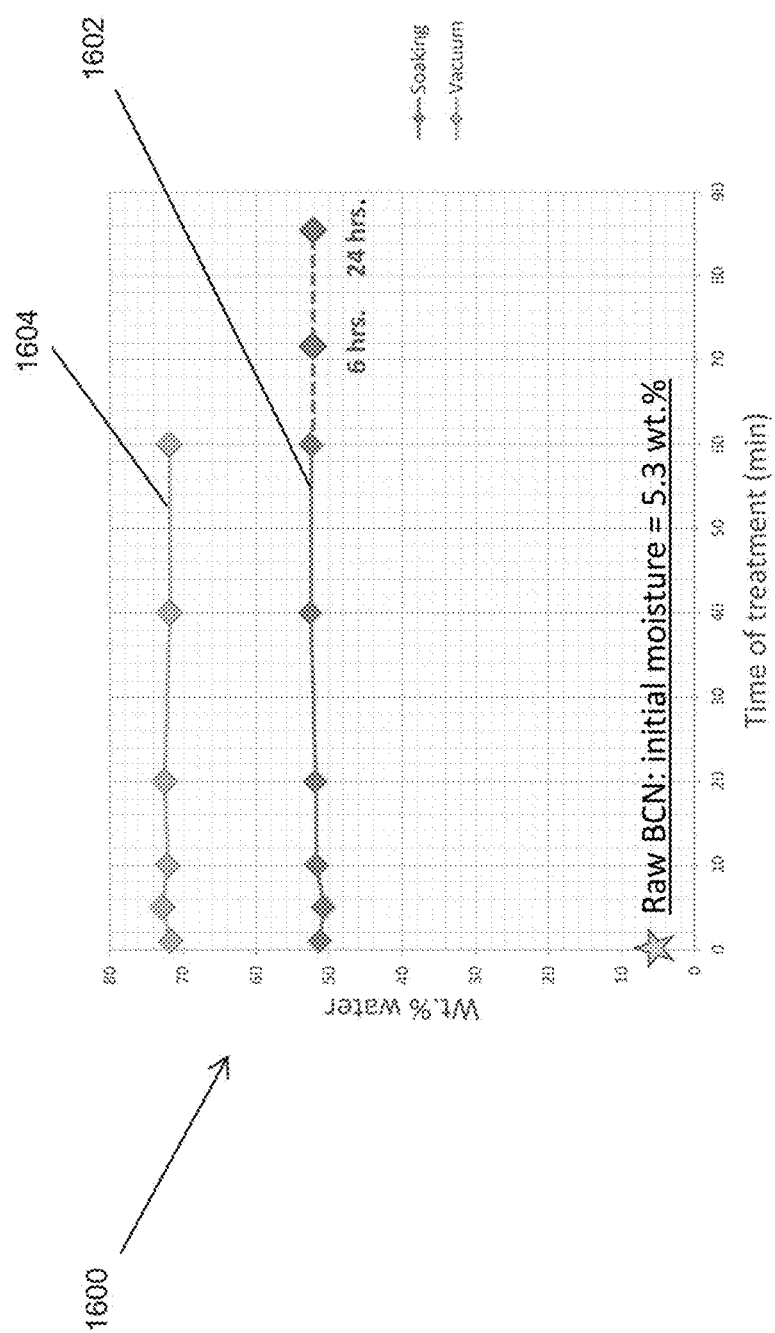
FIG. 16 illustrates the improved liquid content of biochar using vacuum impregnation as against soaking the biochar in liquid.

In one experiment, equal quantities of pine biochar were mixed with equal quantities of water, the first in a beaker, the second in a vacuum flask. The mixture in the beaker was continuously stirred for up to 24 hours, then samples of the suspended solid were taken, drained and analyzed for moisture content. The mixture in the vacuum flask was connected to a vacuum pump and negative pressure of 15" was applied. Samples of the treated solid were taken, drained and analyzed for moisture content. FIG. 16 is a chart illustrating the results of the experiment. The lower graph 1602 of the chart, which shows the results of soaking over time, shows a wt. % of water of approximately 52%. The upper graph 1604 of the chart, which shows the results of vacuum impregnation over time, shows a wt. % of water of approximately 72%.

Figures 17A, 17B:
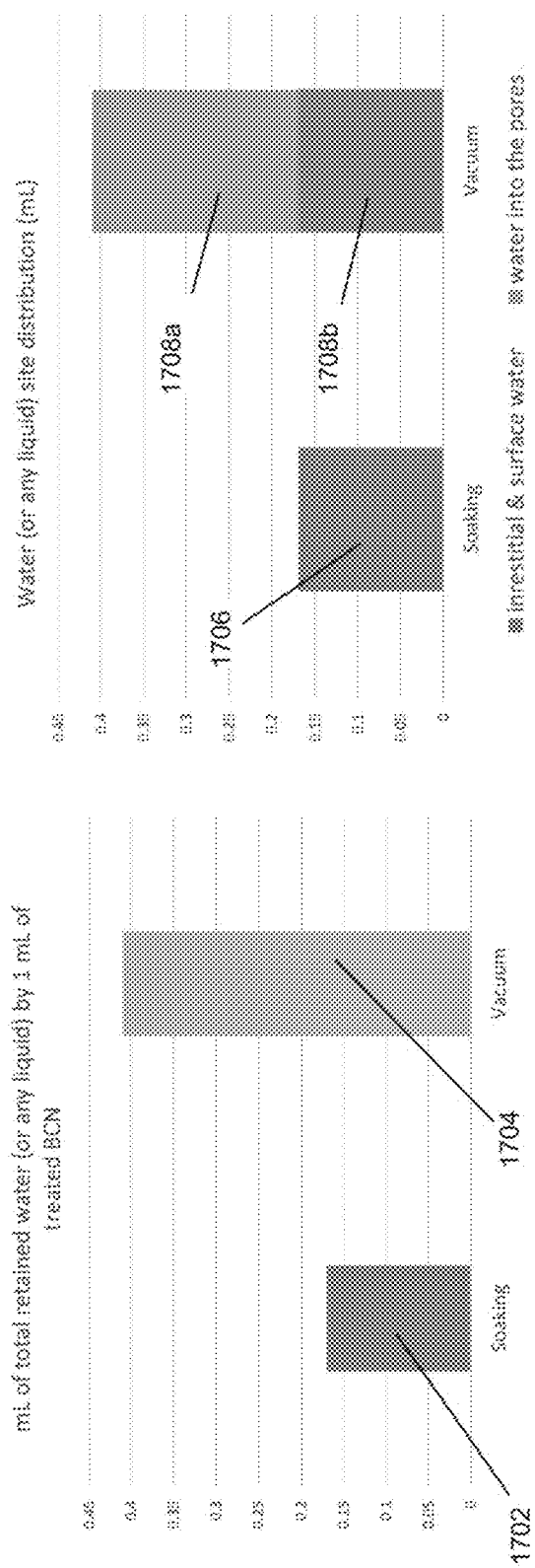
FIG. 17a is a chart comparing total retained water of treated biochar after soaking and after vacuum impregnation.
FIG. 17b is a chart comparing water on the surface, interstitially and in the pores of biochar after soaking and after vacuum impregnation.

FIGS. 17a and 17b show two charts that further illustrate that the total water and/or any other liquid content in processed biochar can be significantly increased using vacuum impregnation instead of soaking. FIG. 17a compares the mL of total water or other liquid by retained by 1 mL of treated pine biochar. The graph 1702 shows that approximately 0.17 mL of water or other liquid are retained through soaking, while the graph 1704 shows that approximately 0.42 mL of water or other liquid are retained as a result of vacuum impregnation. FIG. 17b shows that the retained water of pine biochar subjected to soaking consists entirely of surface and interstitial water 1706, while the retained water of pine biochar subjected to vacuum impregnation consists not only of surface and interstitial water 1708a, but also water impregnated in the pores of the biochar 1708b.

Figure 18:
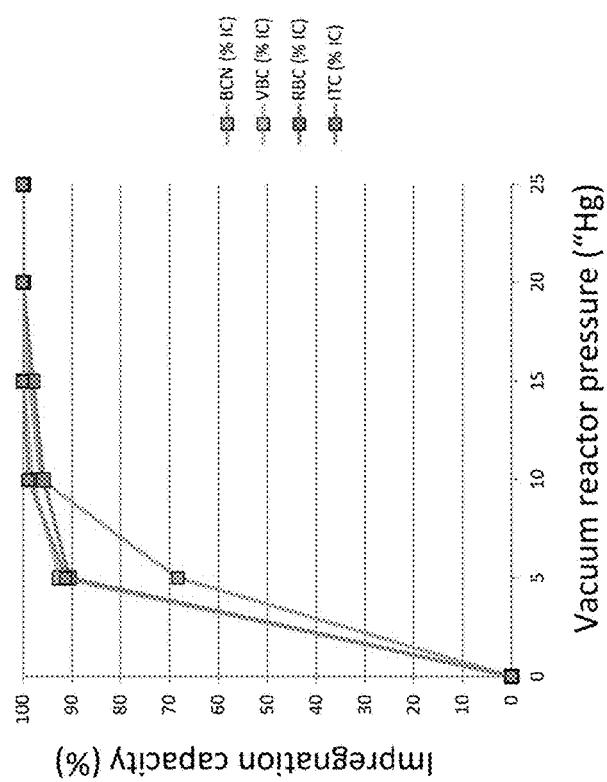
FIG. 18 illustrates how the amount of water or other liquid in the pores of vacuum processed biochars can be increased varied based upon the applied pressure.

In addition, as illustrated by FIG. 18, the amount of moisture content impregnated into the pores of vacuum processed biochars by varying the applied (negative) pressure during the treatment process. The graphs of four different biochars all show how the liquid content of the pours of each of them increase to 100% as vacuum reactor pressure is increased.

In another experiment, the percentage of water retained in the pores of pine derived biochar was measured to determine the difference in retained water in the pores of the biochar (i) soaked in water, and (ii) mixed with water subjected to a partial vacuum. For the soaking, 250 mL of raw biochar was mixed with 500 mL water in a beaker. Upon continuous stirring for 24 hrs., aliquots of the suspended solid were taken, drained on a paper towel and analyzed for moisture content. For the vacuum, 250 mL of raw biochar was mixed with 500 mL water in a vacuum flask. The flask was connected to a vacuum pump and negative pressure of 15" has been applied, aliquots of the treated solid were taken, drained on a paper towel and analyzed for moisture content.

The total retained water amounts were measured for each sample. For the soaked biochar, the moisture content of biochar remains virtually constant for the entire duration of the experiment, 52 wt. % (i.e. 1 g of "soaked biochar" contains 0.52 g water and 0.48 g "dry biochar"). Taking into account the density of raw biochar, 0.16 g/cm$^3$ (or mL), the volume of the 0.48 g "dry biochar" is 3.00 mL (i.e. 3 mL dry biochar can "soak" and retain 0.52 mL water, or 1 mL dry biochar can retain 0.17 mL water (sorbed on the surface and into the pores)).

For vacuum, the moisture content of the biochar remains virtually constant for the entire duration of the experiment, 72 wt. %, (i.e. 1 g of vacuum impregnated biochar contains 0.72 g water and 0.28 g "dry biochar"). Taking into account the density of raw biochar, 0.16 g/cm$^3$ (or mL), the volume of the 0.28 g "dry biochar" is 1.75 mL (i.e. 1.75 mL dry biochar under vacuum can "absorb" and retain 0.72 mL water, or 1 mL dry biochar can retain 0.41 mL water (sorbed on the surface and into the pores)).

It was next determined where the water was retained—in the pores or on the surface of the biochar. Capillary porosity ("CP") (vol % inside the pores of the biochar), non-capillary porosity ("NCP") (vol. % outside/between the particles), and the total porosity (CP+NCP)) were determined. Total porosity and non-capillary porosity were analytically determined for the dry biochar and then capillary porosity was calculated.

Since the dry biochar used in this experiment had a density less than water, the particles could be modeled and then tested to determine if soaking and/or treating the biochar could infuse enough water to make the density of the biochar greater than that of water. Thus, the dry biochar would float and, if enough water infused into the pores, the soaked or treated biochar would sink. Knowing the density of water and the density of the biochar, calculations were done to determine the percentage of pores that needed to be filled with water to make the biochar sink. In this specific experiment, these calculations determined that more than 24% of the pore volume would need to be filled with water for the biochar to sink. The two processed biochars, soaked and vacuum treated, were then immersed in water after 1 hour of said processing. The results of the experiment showed that the vast majority of the soaked biochar floated and remained floating after 3 weeks, while the vast majority of the vacuum treated biochar sank and remained at the bottom of the water column after 3 weeks.

Using the results of these experiments and model calculations, the biochar particles can be idealized to estimate how much more water is in the pores from the vacuum treatment versus soaking. Since the external surface of the materials are the same, it was assumed that the samples retain about the same amount of water on the surface. Then the most conservative assumption was made using the boundary condition for particles to be just neutral, i.e. water into pores equal 24%, the water distribution is estimated as follows:

|  | DRY BIOCHAR | SOAKED BIOCHAR | VACUUM TREATED BIOCHAR |
|---|---|---|---|
| Experimental result | FLOATED | FLOATED | SANK |
| Total water (determined in first part of experiment) | 0% | 52% | 72% |
| Water in the pores (assumed for floating biochar to be boundary condition, calculated for biochar that sank) | 0% | 24% | 44% |
| Water on the surface (calculated for floating biochar, assumed to match floating biochar for the biochar that sank) | 0% | 28% | 28% |

In summary, these experimental tests and model calculations show that through vacuum treatment more than 24% of the pores of the biochar can be filled with water and in fact at least 1.8 times the amount of water can be infused into the pores compared to soaking. Vacuum treatment can impregnate almost two times the amount of water into the pores for 1 minute, while soaking does not change the water amount into the pores for three weeks.

The pores may be substantially filled or completely filled with additives to provide enhanced performance features to the biochar, such as increased plant growth, nutrient delivery, water retention, nutrient retention, disadvantageous species control, e.g., weeds, disease causing bacteria, insects, volunteer crops, etc. By infusing liquid into the pore structure through the application of positive or negative pressure, surfactant and/or ultrasonic waves, alone or in combination, provides the ability to impregnate the mesopores and macropores of the biochar with additives, that include, but are not limited to, soil enhancing solutions and solids.

The additive may be a soil enhancing agent that includes, but is not be limited to, any of the following: water, water solutions of salts, inorganic and organic liquids of different polarities, liquid organic compounds or combinations of organic compounds and solvents, mineral and organic oils, slurries and suspensions, supercritical liquids, fertilizers, PGPB (including plant growth promoting rhizobacteria, free-living and nodule-forming nitrogen fixing bacteria, organic decomposers, nitrifying bacteria, and phosphate solubilizing bacteria), biocontrol agents, bioremediation agents, saprotrophic fungi, ectomycorrhizae and endomycorrhizae, among others.

Fertilizers that may be infused into the biochar include, but are not limited to, the following sources of nitrogen, phosphorus, and potassium: urea, ammonium nitrate, calcium nitrate, sulfur, ammonium sulfate, monoammonium phosphate, ammonium polyphosphate, potassium sulfate, or potassium chloride.

Similar beneficial results are expected from other additives, such as: bio pesticides; herbicides; insecticides; nematicides; plant hormones; plant pheromones; organic or inorganic fungicides; algicides; antifouling agents; antimicrobials; attractants; biocides, disinfectants and sanitizers; miticides; microbial pesticides; molluscicides; bacteriacides; fumigants; ovicides; repellents; rodenticides, defoliants, desiccants; insect growth regulators; plant growth regulators; beneficial microbes; and, microbial nutrients or secondary signal activators, that may also be added to the biochar in a similar manner as a fertilizer. Additionally, beneficial macro- and micro-nutrients such as, calcium, magnesium, sulfur, boron, zinc, iron, manganese, molybdenum, copper and chloride may also be infused into the biochar in the form of a water solution or other solvent solution.

Examples of compounds, in addition to fertilizer, that may be infused into the pores of the biochar include, but are not limited to: phytohormones, such as, abscisic acid (ABA), auxins, cytokinins, gibberellins, brassinosteroies, salicylic acid, jasmonates, planet peptide hormones, polyamines, karrikins, strigolactones; 2,1,3-Benzothiadiazole (BTH), an inducer of systemic acquired resistance that confers broad spectrum disease resistance (including soil borne pathogens); signaling agents similar to BTH in mechanism or structure that protects against a broad range or specific plant pathogens; EPSPS inhibitors; synthetic auxins; photosystem I inhibitors photosystem II inhibitors; and HPPD inhibitors. Growth media, broths, or other nutrition to support the growth of microbes or microbial life may also be infused such as Lauryl Tryptose broth, glucose, sucrose, fructose, or other sugars or micronutrients known to be beneficial to microbes.

In one example, a 1000 ppm $NO_3^-$ N fertilizer solution is infused into the pores of the biochar. As discussed above, the method to infuse biochar with the fertilizer solution may be accomplished generally by placing the biochar in a vacuum infiltration tank or other sealable rotating vessel, chamber or tank. When using vacuum infiltration, a vacuum may be applied to the biochar and then the solution may be introduced into the tank. Alternatively, the solution and biochar may both be introduced into the tank and, once introduced, a vacuum is applied. Based upon the determined total pore volume of the biochar or the incipient wetness, the amount of solution to introduce into the tank necessary to fill the pore of the biochar can be determined. When infused in this manner, significantly more nutrients can be held in a given quantity of biochar versus direct contact of the biochar with the nutrients alone.

When using a surfactant, the biochar and additive solution may be added to a tank along with 0.01-20% of surfactant, but more preferably 1-5% of surfactant by volume of fertilizer solution. The surfactant or detergent aids in the penetration of the wash solution into the pores of the biochar. The same or similar equipment used in the vacuum infiltration process can be used in the surfactant treatment process. Although it is not necessary to apply a vacuum in the surfactant treatment process, the vacuum infiltration tank or any other rotating vessel, chamber or tank can be used. Again, while it is not necessary to apply a vacuum, a vacuum may be applied or the pressure in the vessel may be changed. Further, the surfactant can be added with or without heat or cooling either of the infiltrate, the biochar, the vessel itself, or any combination of the three.

The utility of infusing the biochar with fertilizer is that the pores in biochar create a protective "medium" for carrying the nutrients to the soil that provides a more constant supply of available nutrients to the soil and plants and continues to act beneficially, potentially sorbing more nutrients or nutrients in solution even after introduction to the soil. By infusing the nutrients in the pores of the biochar, immediate oversaturation of the soil with the nutrients is prevented and a time released effect is provided. This effect is illustrated in connection with FIGS. 18 and 19 below. As demonstrated in connection with FIGS. 19 & 20 below, biochars having pores infused with additives, using the infusion methods described above, have been shown to increase nutrient retention, increase crop yields and provide a steadier flow of fertilizer to the root zones of the plants.

Figure 19:
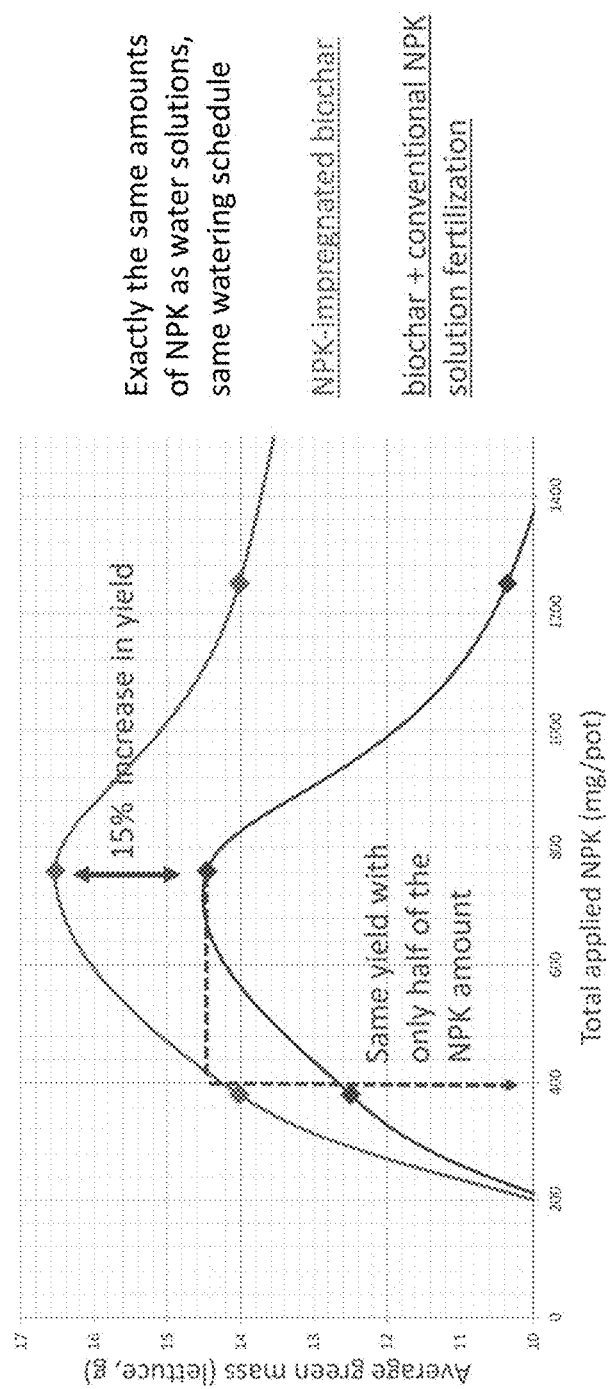
FIG. 19 illustrates the effects of NPK impregnation of biochar on lettuce yield.

FIG. 19 is a chart showing improved mass yield in lettuce with fertilizer infused biochar using vacuum impregnation. FIG. 19 compares the mass yield results of lettuce grown in different environments. One set of data measurements represents lettuce grown in soil over a certain set time period with certain, predetermined amounts of fertilizer infused into the biochar. A second set of data represents lettuce grown in soil over a certain set period of time with the same amount of unimpregnated biochar added at the beginning of the trial and certain predetermined amounts of NPK solution added to the soil over time. Growth comparisons were made between the same amount of fertilizer solution infused into the biochar as added directly to the soil, using the same watering schedule. As illustrated, the test results demonstrated a 15% yield increase in growth when infusing approximately 750 mg/pot of NPK into the biochar than when applying it directly to the soil. Similarly, the same mass yield of lettuce is achieved at 400 mg NPK/pot with infused biochar than at 750 mg/pot when adding the fertilizer solution directly to the soil.

Figure 20:
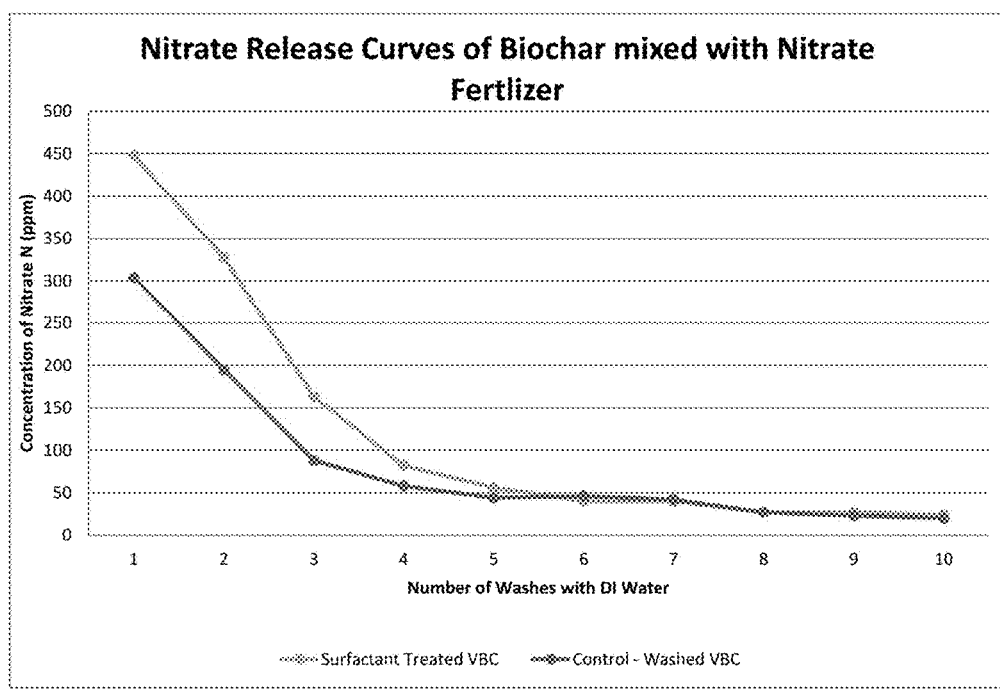
FIG. 20 is a chart showing nitrate release curves of treated biochars infused with nitrate fertilizer.

FIG. 20 is a chart illustrating the concentration of nitrate (N) found in distilled water after washing differentially treated biochar. In the illustrated example, two biochar samples (500 ml each) mixed with 1000 ppm $NO_3^-$ N fertilizer solution were washed with distilled water. The resulting wash was then tested for the presence of nitrate (N), measured in ppm. In one sample, the biochar was submerged in and mixed with the nutrient solution. In the other example, the biochar was mixed or washed with a nutrient solution augmented with 1% surfactant by volume (i.e., 1 ml of surfactant per 100 ml of fertilizer solution) in a tumbler. In both examples, the biochar was not dried completely before infusion with the $NO_3^-$ N fertilizer solution, but used as received with a moisture content of approximately 10-15%. In both examples, the biochar was mixed with solution and/or surfactant (in the case of a second sample) with a bench scale tumbler, rotating the drum for four (4) minutes without vacuum. The results demonstrate that the biochar treated with the 1% surfactant increases the efficiency of infiltrating nitrate fertilizer into biochar and then demonstrates the release of the nutrient over time. To yield the above data, the test was repeated six times for each treatment sample, with 10 washes for each sample per repeat test. Adjusting the method of treatment (amount of vacuum, amount or residence time, addition of surfactant, additional substances infused, and optionally additional treatments after infusion) based on the substance being infused can modify and adjust the release characteristics of the material, either causing more rapid release, slower release, or a modification of the shape of the release curve over time.

Figure 21A:
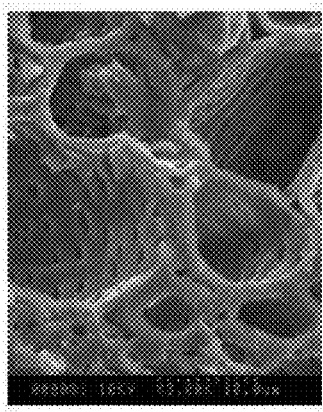
FIG. 21a is a SEM (10 KV×3.00K 10.0 µm) of pore morphology of raw biochar.
Figure 21B:
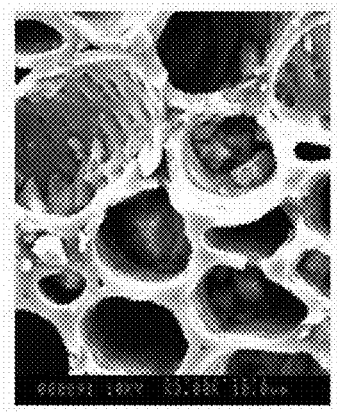
FIG. 21b is a SEM (10 KV×3.00K 10.0 µm) of pore morphology of raw biochar of FIG. 21a after it has been infused with microbial species.
Figure 21C:
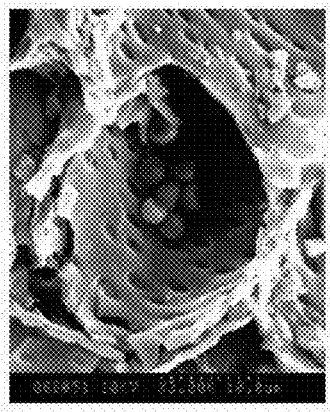
FIG. 21c is a SEM (10 KV×3.00K 10.0 µm) of a pore morphology of another example of raw biochar of FIG. 21a after it has been infused with microbial species.

Another example of additive infused biochar is a case when the beneficial inoculant contains microbes (fungi and/or PGPB) or microbial spores. FIGS. 21a, 21b and 21c show scanning electron microscopy (SEM) images of raw biochar compared to ones that have been processed by being infused under vacuum with bio-extract containing different microbial species.

FIG. 21a is a SEM (10 KV×3.00K 10.0 μm) of pore morphology of raw biochar. FIG. 21b is a SEM (10 KV×3.00K 10.0 μm) of pore morphology of raw biochar of FIG. 21a after it has been infused with microbial species. FIG. 21c is a SEM (10 KV×3.00K 10.0 μm) of a pore morphology of another example of raw biochar of FIG. 20a after it has been infused with microbial species. The images confirm the ability to incorporate different microbes into the pores of biochar by our treatment. In turn, these beneficial microbes interact with and enhance the performance of the plants' root systems when the so processed biochar is mixed with the soil in the root zone.

Thus, treated biochar can have a microbial community in its pores (macro-, meso-, and combinations and variations of these), on its pore surfaces, embedded in it, located on its surface, and combinations and variations of these. The microbial community can have several different types, e.g., species, of biologics, such as different types of bacteria or fungi, or it may have only a single type. A primary purpose, among many purposes, in selecting the microbial population is looking toward a population that will initiate a healthy soil, e.g., one that is beneficial for, enhances or otherwise advance the desired growth of plants under particular environmental conditions. However, the microbes may also be targeted towards increasing animal health either directly or through interactions with other microbes in the animals digestive tract.

Typically the prior art teaches placing biochar on soils without 'precharging' with bacteria or combining the biochar with compost and using this mixture as a soil amendment. The nature of the microbial population in this compost mixture is poorly disclosed by the prior art. Thus, through impregnation of the biochar particles, one can achieve a predetermined and controllable amount of a microbial community, e.g., population, into the soil. This integration of a microbial community with a biochar particle, and biochar batches provides the ability to have controlled addition, use and release of the microbes in the community. This integration further enhances, promotes and facilitates the growth of roots, e.g., micro-roots, in the biochar pores, e.g., pore morphology, pore volume.

Other methods exist for integrating a microbial community with a previously infused biochar particle. Different manners and methods would be preferred depending on needs to minimize contamination, encourage biochar pore colonization/infiltration, minimize labor and cost and producing a uniform, or mostly uniform, product.

Methods for integrating a microbial community with a biochar particle may include, but are not be limited to the following: while under vacuum, pulling the microbial solution through a treated biochar bed that is resting on a membrane filter; spraying a microbial solution on top of a treated biochar bed; lyophilizing a microbial solution and then blending said freeze dried solution with the treated biochar; again infusing, as defined previously, the treated biochar with a microbial solution; adding treated biochar to a growth medium, inoculating with the microbe, and incubating to allow the microbe to grow in said biochar containing medium; infusing, as defined previously, the biochar with a food source and then introducing the substrate infused biochar to a microbe and incubating to allow the microbes to grow; blending commercially available strains in dry form with treated biochar; adding the treated biochar to a microbial solution and then centrifuging at a high speed, potentially with a density gradient in order to promote the biochar to spin down with the microbes; densely packing a column with treated biochar and then gravity flowing a microbial solution through the column and possibly repeating this multiple times; or adding the microbe to a solution based binder that is well known to enter the treated biochar pores and then adding said solution to the treated biochar. Growth media may also be infused into the pores and the intended microbes may be encouraged to grow into the pore space by the presence of nutrition or other favorable conditions. The microbes may be added before or after infusion with the growth media, or even suspended in the media itself. This technique may be used independently or in combination with the others above. In order to insure the proper microbial community the treated biochar may need to be sterilized prior to these methods for integrating a microbial community. All or parts of the above manners and methods may be combined to create greater efficacy. In addition, those skilled in the art will recognize that there may be additional manners or methods of infusing biochars with microbials, including those created by the combination of one or more of the manners and methods listed above, without departing from the scope of the present invention.

One manner in which the population of a microbial community can be determined is by PLFA (Phospholipid-derived fatty acids) analysis. Biological cell membranes are composed of a phospholipid bilayer with fatty acid side chains that are unique to certain families of organisms. PLFA analysis extracts the fatty acid side chains of phospholipid bilayers and measures the quantity of these biomarkers using GC-MS. An estimate of the microbial community population can thus be determined through PLFA analysis. The microbial activity may also be inferred through PLFA analysis by monitoring the transformation of specific fatty acids. Next generation sequencing of the conserved ribosomal RNA regions of the bacteria and fungi may allow for more direct and accurate measurements than PLFA.

Treated biochars can have a mixture of bacteria and fungi, or other microbes. For example, a preferred functional biochar, can have a preferred range for bacterial population of from about 50-5000000 micrograms/g biochar; and for fungi, from about 5 to 500000 micrograms/g biochar.

Compared to a biochar that has been bathed with a compost tea, which may have a relatively short, e.g., a few days for the life of the microbes, the impregnated populations of examples of the present treated biochars, are stable over substantially longer periods of time, e.g., at least an 8 week period and in some cases 1 year or more as measured by PLFA. Thus, the impregnation of the biochar with a microbial population provides for extended life of the microbes by at least 5×, 10×, or more over simple contact or immersion. In fact, some microbes may be better suited to surfactant infiltration versus vacuum infiltration and vice versa and this may impact the shelf life, penetration, viability, or other characteristics of the microbes.

Figure 22:
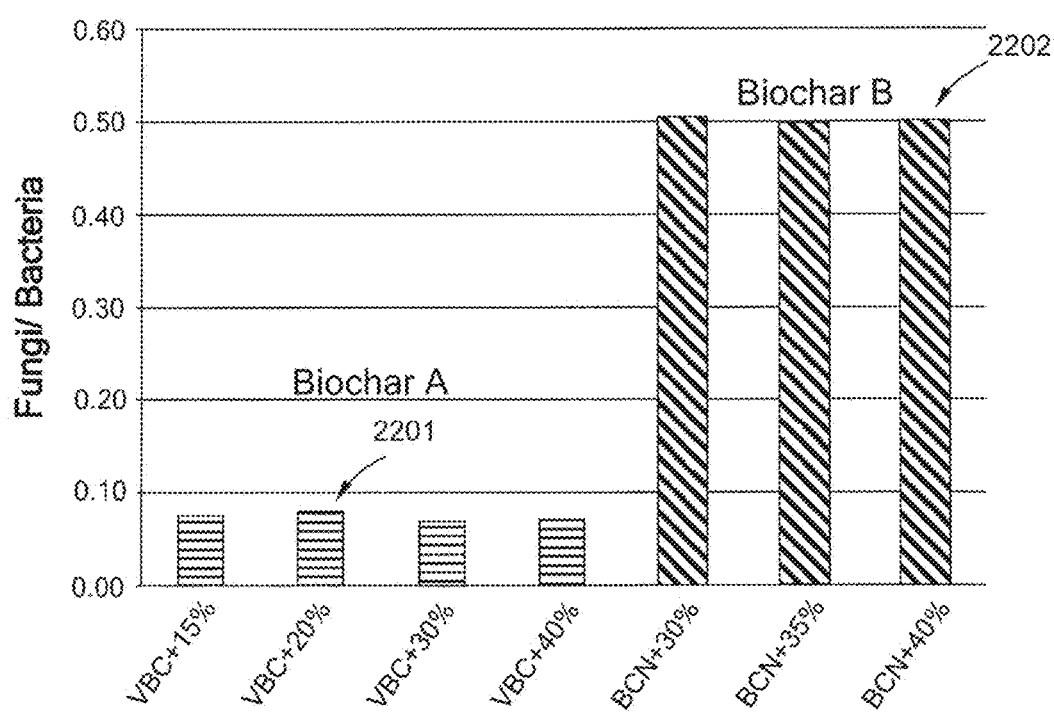
FIG. 22 is a chart showing the total fungi/bacteria ratio for two biochars derived from different biochar starting materials, e.g., feedstocks.

FIG. 22 shows the total fungi/bacteria ratio for two biochars derived from different biochar starting materials, e.g., feedstocks. Each biochar was loaded with different levels of moisture, and the total fungi/bacteria ratio was monitored during the first week. Biochar A 2201 showed a constant total fungi/bacteria ratio of 0.08 across moisture levels ranging from 15% to 40%, while Biochar B 2202 showed a constant total fungi/bacteria ratio of 0.50 for moisture levels ranging from 30% to 40%. It is theorized that, a fungi/bacteria ratio between 0.05 and 0.60 is an effective prescription for a stable biochar composition. This composition allows a commercially viable product, which has sufficient shelf life that it can be delivered to storage houses waiting for the proper planting window.

As used herein, unless stated otherwise, the stable shelf life of a biochar product having a microbial population is the period of time over which the product can be stored in a warehouse, e.g., dry environment, temperature between 40° F.-90° F., with a less than 50% decrease in microbial population.

It is theorized that the difference in the observed total fungi/total bacteria ratios of may also be explainable by the structures of the biochars. Biochar's having an open pore structure, e.g., more interconnected pores, promotes more bacteria formation; while closed pores, e.g., relatively non-connected nature of the pores, tends to promote fungi formation. Biochars with differing microbial communities may be beneficial for specific applications in commercial agriculture. Thus, custom or tailored loading of the microbial population may be a desired implementation of the present invention.

For example, as shown in FIGS. 23a, 23b and 23c, Biochar A 2301 shows that it has a greater population of, e.g., is inhabited by, more gram negative, gram positive and *actinomycetes* than Biochar B 2302. Thus, for example, Biochar A would be more applicable for use with certain agricultural crops in which PGPB species in the *actinomycetes*, gram (−) *pseudomonas*, and *bacillus* groups are used for nutrient utilization and uptake. Many vegetable and short cycle row crops such as tomatoes, lettuce, and celery form mutualistic relationships with bacteria that lead to the formation of biofilms on root hairs that function not only in nutrient uptake but also in plant pathogen resistance. The presence of biofilms in Biochar A would consequently promote bacterial colonization of plant root hairs as they encounter the biochar in the soil.

It is further theorized that, in general, biochars with greater fungal development may be better suited for perennial crops such as grapes, almonds, blueberries, and strawberries in which symbiotic relationships with arbuscular mycorrhizal fungi (AMF) are favored over PGPRs. The presence of high concentrations of AMF spores in biochars can therefore rapidly promote fungal colonization of plant root hairs leading to extensive mycelial development. Increased plant root associations with mycelial filaments would consequently increase nutrient and water uptake.

In general, bacteria communicate via the distribution of signaling molecules which trigger a variety of behaviors like swarming (rapid surface colonization), nodulation (nitrogen fixation), and virulence. Biochars can bind signaling molecules and in particular it is believed can bind a major signaling molecule to their surface. This binding ability can be dependent upon many factors including on the pyrolysis temperature. This dependency on pyrolysis temperature and other factors can be overcome, mitigated, by the use of examples of the present vacuum infiltration techniques. For example, a signaling molecule that is involved in quorum sensing-multicellular-like cross-talk found in prokaryotes can be bound to the surface of biochars. Concentration of biochars required to bind the signaling molecule decreased as the surface area of biochars increased. These signaling molecules may be added to the surface of a biochar and may be used to manipulate the behavior of the bacteria. An example of such a use would be to bind the molecules which inhibit cell-to-cell communication and could be useful in hindering plant pathogens; using techniques in the present invention signaling molecules may be added to the surface of a biochar to engineer specific responses from various naturally occurring bacteria.

Further, a benefit of examples of biochars of the present inventions is the ability to provide an environment where bacteria communities can flourish. Bacterial communities can shift their morphology to increase nutritional access and decrease predation. One such modification is that the bacteria may attach to surfaces, such as those found in biochar, in a densely compacted community. In this compacted form they may form an extracellular polymeric substance (EPS) matrix called a biofilm. These communities can contain a few hundred different species which find shelter under the protective EPS coating from predatory protozoa, pathogens, contaminants, and other environmental stressors. Thus, examples of biochars produced in accordance with the vacuum infiltration methods may be used as carriers for established biofilms, or have substances added to promote the production of biofilms; and thus biochars with such films many used in agricultural settings.

The above are only a few examples of how additive infused biochar may be produced for different uses. Those skilled in the art will recognize that there may be other mechanisms for infusing fertilizer or other soil additives into the pores of the biochar without departing from the scope of the invention. Those skilled in the art will further recognize that the present invention can be used on any type of soil application, including, but not limited to, the following: crops, turf grasses, potted plants, flowering plants, annuals, perennials, evergreens and seedlings, as will be further described below.

For example, in another implementation, additive infused biochar may be produced for use for consumption by animals and/or humans. Biochar may be infused in the same manner as described above with nutrients (such as carbohydrates, minerals, proteins, lipids), vitamins, drugs and/or other supplements (such as enzymes or hormones, to name a few), or a combination of any of the foregoing, for consumption by either humans and/or animals. Coloring, flavor agents and/or coating may also be infused into the pores of the biochar or applied to the surface. The foregoing may be included to enhance the performance of the substance in the digestive tract or to ease or facilitate the ingestion of the biochar.

In certain application, the pores may be substantially filled or completely filled with additives to provide enhanced performance features to the biochar, such as improved rumen quality, nutrient delivery, drug delivery, water retention, nutrient retention, disadvantageous species control, e.g., disease causing bacteria. Infusing liquid deep into the pore structure through the application of positive or negative pressure, surfactant and/or ultrasonic waves, alone or in combination, provides the ability to impregnate the mesopores and macropores of the biochar with additives, that include, but are not limited to, animal health enhancing solutions and solids.

The additive may include, but not be limited to, water, water solutions of salts, inorganic and organic liquids of different polarities, liquid organic compounds or combinations of organic compounds and solvents, vitamins, supplements and/or medications, nutrients, minerals, oils, amino acids, fatty acids, supercritical liquids, growth promotants, proteins and enzymes, phytogenics, carbohydrates, antimicrobial additives and sensory additives (e.g. flavor enhancers salt or sweeteners or smell enhancers), among others, to provide nutrition, promote the overall health of the animal, and increase the animal's desire to ingest said biochar. Vitamins, supplements, minerals, nutritional and/or medications may be used to prevent, treat or cure animal illnesses and diseases and/or control the nutritional value of the animals overall diet.

For example, dietary supplementation with certain nutrients (e.g., arginine, glutamine, zinc, and conjugated linoleic acid) can regulate gene expression and key metabolic pathways to improve fertility, pregnancy outcome, immune function, neonatal survival and growth, feed efficiency, and meat quality. Such additives in the biochar can help provide the proper balance of protein, energy, vitamins and nutritionally important minerals in animal diets. Additionally, for poultry, the additive may include, for example, coccidiostats and/or histomonostats, which are both shown to control the health of the poultry. The present invention can be used to help correct deficiencies in basal diets (e.g., corn- and soybean meal-based diets for swine; milk replacers for calves and lambs; and available forage for ruminants).

The treated biochar can also have a microbial community infused in its pores (macro-, meso-, and combinations and variations of these), on its pore surfaces, embedded in it, located on its surface, and combinations and variations of these. The microbial community can have several different types, e.g., species, of biologics, such as different types of bacteria or fungi, or it may have only a single type. A primary purpose, among many purposes, in selecting the microbial population is looking toward a population that will promote animal health either directly or through interactions with other microbes in the animals digestive tract. These types of beneficial microbes are essential to a functional gastrointestinal tract and immune system in many types of animals, serving many functional roles, including degradation of ingesta, pathogen exclusion, production of short-chain fatty acids, compound detoxification, vitamin supplementation, and immunodevelopment. Beneficial bacteria include *Lactobacillus acidophilus* LA1 (which decreases adhesion of diarrheagenic *Escherichia coli* to Caco-2 cells by 85% and prevents invasion of the same cells by *E. coli* (95%), *Yersinia pseudo-tuberculosis* (64%) and *Salmonella enterica* serovar *Typhimurium*) and *Lactobacillus rhamnosus* GG to prevent *E. coli* O157:H7-induced lesions in Caco-2 cells.

Further, biochar may be impregnated with probiotic bacteria to treat diseases in farm-raised fish. Infectious diseases pose one of the most significant threats to successful aquaculture. The maintenance of large numbers of fish crowded together in a small area provides an environment conducive for the development and spread of infectious diseases. In this crowded, relatively unnatural environment, fish are stressed and more susceptible to disease. Moreover, the water environment, and limited water flow, facilitates the spread of pathogens within crowded populations. There is thus an urgent need in aquaculture to develop microbial control strategies, since disease outbreaks are recognized as important constraints to aquaculture production and trade and since the development of antibiotic resistance has become a matter of growing concern. One alternative disease control relies on the use of probiotic bacteria as microbial control agents. Another implementation of the invention therefore involves the impregnation of biochar for consumption by aquatic animals as a treatment or preventative for disease.

Additionally, biochar may be infused with bacteria which prove helpful in methane reduction. An example of this is to infuse the biochar with methanotrophic bacteria (bacteria which are able to metabolize methane as a source of carbon and energy). Bacteria which metabolize methane are useful in two regards—they can reduce the environmental methane emissions from the rumen and they (the bacteria) also serve as nutrition for the animal itself, leading to increased weight gain. Infusing biocarbon with microbes such as these can lead to methane reduction in cattle applications that exceeds the methane reduction of solely untreated biochar itself.

In yet another example, biochar may be infused with plant growth promoting bacteria ("PGPB"). PGPB includes, for example, plant growth promoting rhizobacteria, free-living and nodule-forming nitrogen fixing bacteria, organic decomposers, nitrifying bacteria, phosphate solubilizing bacteria, biocontrol agents, bioremediation agents, archea, *actinomycetes*, thermophilic bacteria, purple sulfur bacteria, cyanobacteria, and combinations and variations of these. Beneficial fungi include, for example, saprotrophic fungi, ectomycorrhizae, endomycorrhizae, ericoid mycorrhizae, and combinations and variations of these.

PGPB may promote plant growth either by direct stimulation such as iron chelation, phosphate solubilization, nitrogen fixation and phytohormone production or by indirect stimulation, such as suppression of plant pathogens and induction of resistance in host plants against pathogens. In addition, some beneficial bacteria produce enzymes (including chitinases, cellulases, -1,3 glucanases, proteases, and lipases) that can lyse a portion of the cell walls of many pathogenic fungi. PGPB that synthesize one or more of these enzymes have been found to have biocontrol activity against a range of pathogenic fungi including *Botrytis cinerea, Sclerotium rolfsii, Fusarium oxysporum, Phytophthora* spp., *Rhizoctonia solani, Pythium ultimum*.

Currently, one of the most economic conventional solid carriers used to deliver microbes is peat. A solid carrier allows for a relatively long shelf life and a more direct application to a plants root system compared to a microbial liquid solution, which would be sprayed directly.

Research has shown a substantial increase in PGPB growth and distribution resulting from being infused in biochar. For example, data resulting from research conducted to compare the effects upon $CO_2$ production (an indicator of bacterial growth) using peat and biochars show the beneficial effects of using various biochars in promoting PGPB growth. As illustrated in the left-hand chart in FIG. 24, peat results in $CO_2$ production of between approximately 10% and 30% (depending upon the grown medium), whereas biochars result in $CO_2$ production of approximately 48% and 80%. Replicated experimental results using different biochars confirm $CO_2$ production of approximately 30% to 70% (depending on the grown medium), as compared to approximately 10% to 20% for the control.

Figure 24:
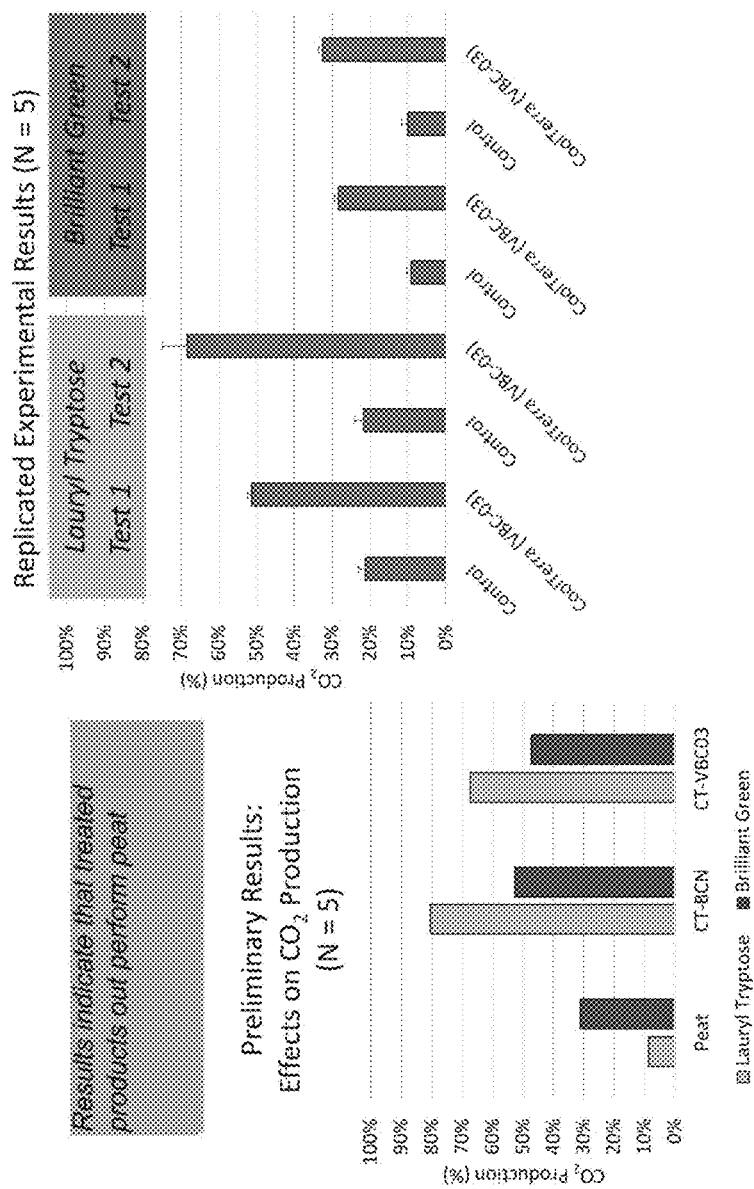
FIG. 24 contains charts illustrating improved results obtained through the use of biochars.
Figure 25:
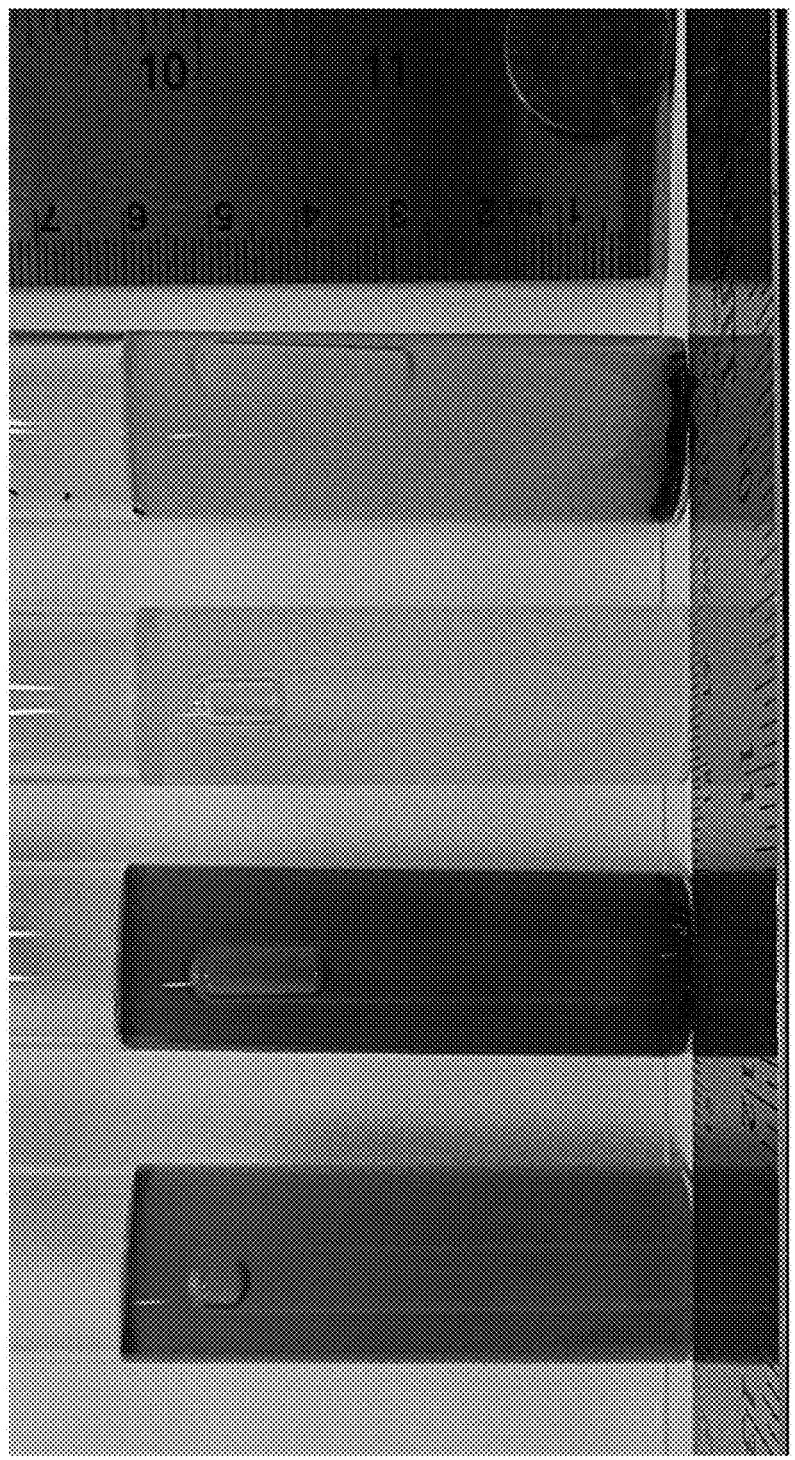
FIG. 25 is an example of carbon dioxide production captured as a continuous gas bubble in BGB (left two tubes) and LTB (right two tubes) growth medium.

The method developed for determining this $CO_2$ production as an indicator of bacterial growth consists of the following. The substrate (e.g., biochar or peat) is sterilized by heating at 110 C for 15 hours. A bacterial stock solution is then created. In this example, Tryptic Soy Broth was solidified with agar at 1.5% w/v in petri plates to isolate the gram negative non-pathogenic organism *Escherichia coli* ATCC 51813 (15 h growth at 37° C.). Then an isolated colony is captured with an inoculating loop and suspend in 10 ml sterile buffer (phosphate buffer saline or equivalent) to create the bacterial stock solution. Lactose containing assays are then used. In this example, test tubes that contain 13 ml of either Lauryl Tryptose Broth (LTB) or Brilliant Green Broth (BGB) that also contain a Durham tube were used. A negative control is generated by adding 10 µL of sterile buffer to triplicate sets of LTB and BGB tubes. A positive control is generated by adding 10 µL of bacterial stock solution to triplicate sets of LTB and BGB tubes. A negative substrate is generated by adding 1.25 ml (~1% v/v) of sterile substrate to triplicate sets of LTB and BGB tubes. A positive substrate is generated by adding 1.25 ml (~1% v/v) of sterile substrate and 10 µL of bacterial stock solution to triplicate sets of LTB and BGB tubes. The tubes of the four treatments are then incubated statically in a test tube rack at 37° C. for at least 15 h. The tubes are then carefully observed and any gas bubbles captured by the Durham tube within respective LTB or BGB tubes are closely measured with a ruler. Small bubbles <0.2 mm should not be considered. A continuous bubble as shown in individual tubes in FIG. 24 are what are observed and quantified. FIG. 25 is an example of carbon dioxide production captured as a continuous gas bubble in BGB (left two tubes) and LTB (right two tubes) growth medium. The percent carbon dioxide production is then calculated by dividing the recorded bubble length by the total Durham tube length and multiplying by 100.

Further tests were conducted using the *Streptomyces lidicus* WYEC 108 bacterium found in one of the commercially available products sold under the Actinovate brand. Actinovate products are biofungicides that protect against many common foliar and soil-borne diseases found in outdoor crops, greenhouses and nurseries. The formulations are water-soluble.

Figure 26:
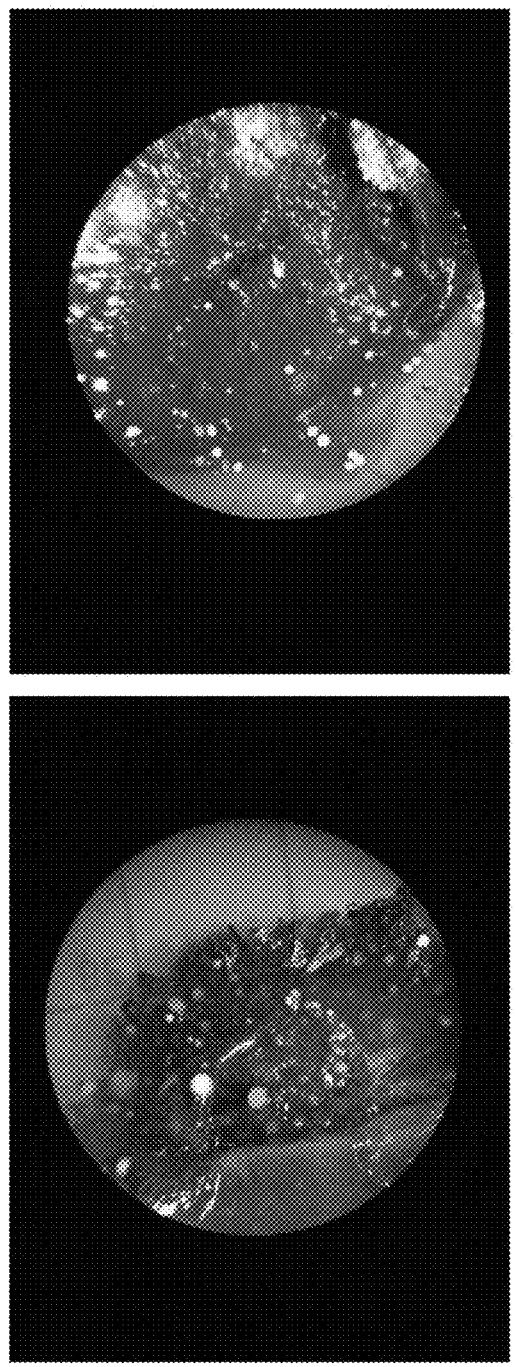
FIGS. 26 and 27 illustrate improved growth rates of colonies of *Streptomyces lydicus* using biochars.

FIG. 26 illustrates the effects upon the growth of *Streptomyces lidicus* using conventional peat versus biochars. In the test illustrated by the photograph on the left of FIG. 26, an Actinovate powder was blended with peat, placed in an inoculated media and incubated at 25° C. The photograph shows the distribution and density of white colonies after 3 days. In the test illustrated by the photograph on the right of FIG. 25, an Actinovate powder was blended with the biochar CoolTerra (VBC-03), placed in an inoculated media and incubated at 25° C. The photograph also shows the distribution and density of white colonies after 3 days, the distribution and density of which are significantly greater than those achieved with peat.

Figure 27:
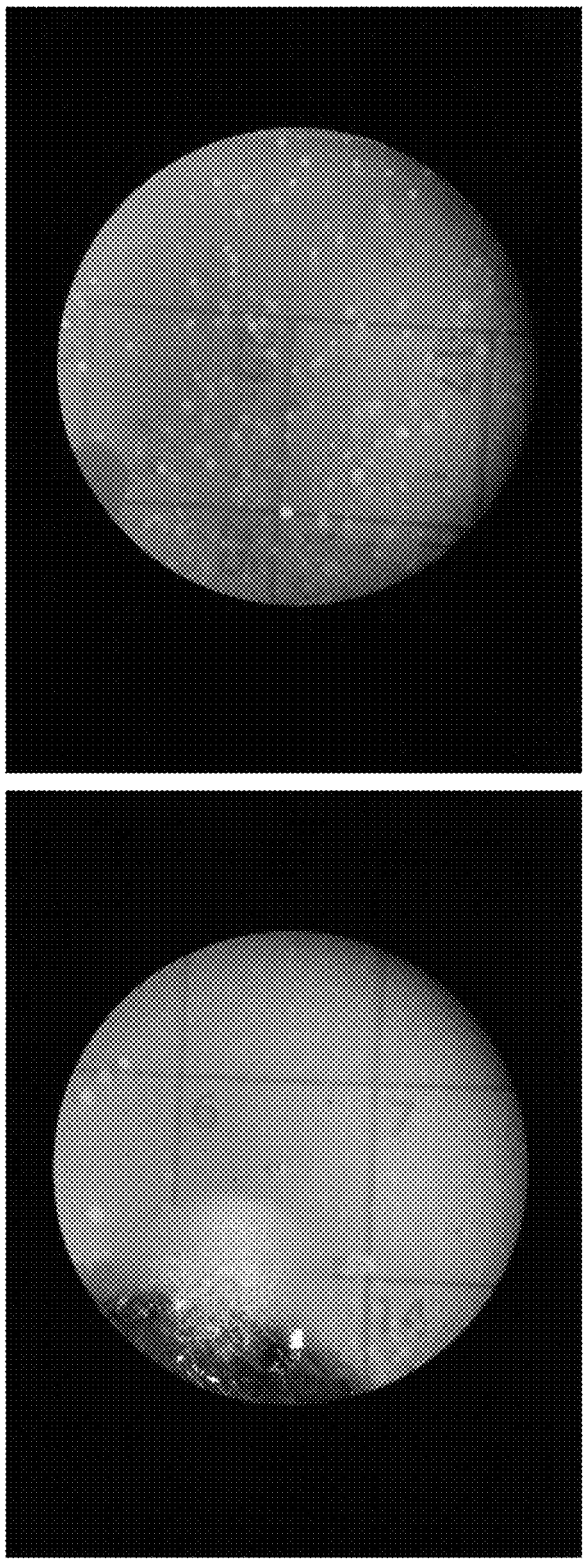

FIG. 27 further illustrates the improved growth of the Actinovate bacterium using biochar versus peat. The left photograph shows only limited and restricted growth away from the peat carrier. The right photograph shows abundant growth of the bacterium spread much farther out from the biochar carrier.

Mycorrhizal fungi, including but not limited to Endomycorrhizae and Ectomycorrhizae, are known to be an important component of soil life. The mutualistic association between the fungi and the plant can be particularly helpful in improving plant survivability in nutrient-poor soils, plant resistance to diseases, e.g. microbial soil-borne pathogens, and plant resistance to contaminated soils, e.g. soils with high metal concentrations. Since mycorrhizal root systems significantly increase the absorbing area of plant roots, introducing mycorrhizal fungi may also reduce water and fertilizer requirements for plants.

Typically mycorrhizae are introduced into soil as a liquid formulation or as a solid in powder or granular form and contain dormant mychorrhizal spores and/or colonized root fragments. Often the most economic and efficient method is to treat the seeds themselves, but dealing with traditional liquid and powder inoculums to coat the seed can be difficult. In accordance with the present invention, inoculated biochar may be used to coat the seeds by, for example, using a starch binder on the seeds and then subjecting the seeds to inoculated biochar fines or powder. Another method is by placing the mycorrhizae inoculum in the soil near the seeding or established plant but is more costly and has delayed response as the plants initial roots form without a mycorrhizal system. This is because the dormant mychorrhize are only activated when they come close enough to living roots which exude a signaling chemical. In addition if the phosphorus levels are high in the soil, e.g. greater than 70 ppm, the dormant mycorrhizae will not be activated until the phosphorus levels are reduced. Thus applying inoculant with or near fertilizers with readily available phosphorus can impede the desired mycorrhizal fungi growth. A third option is to dip plant roots into an inoculant solution prior to replanting, but this is costly as it is both labor and time intensive and only applicable for transplanting.

If the colonization of mycorrhizae can be quickened and the density of the mycorrhizae's hyphal network can be increased then the beneficial results of mycorrhizal root systems, e.g. increased growth, increased survivability, reduced water, and reduced fertilizer needs, can be realized sooner. Prior art shows that compost, compost teas, humates, and fish fertilizers can improve microbial activities and in more recent studies have shown physically combining arbuscular mycorrhizal fungi (AMF) inoculant with raw biochar has resulted in additional plant yield compared to each alone. See Hammer, et. al., *Biochar Increases Arbuscular Mycorrhizal Plant Growth Enhancement and Ameliorates Salinity Stress*, Applied Soil Ecology Vol 96, November 2015 (pg 114-121).

An ideal carrier for the mycorrhizae would have moisture, air, a neutral pH, a surface for the fungi to attach, and a space for the roots and fungi to meet. Thus a previously infused biochar created by the method disclosed above would be a better carrier than raw biochar alone. The infused biochar could be physically mixed with a solid mycorrhizal fungi inoculant or sprayed with a liquid mycorrhizal inoculant prior to or during application at seeding or to established plants. Additionally, the infused biochar and mycorrhizal fungi inoculant could be combined to form starter cubes, similar to Organo-Cubes, rockwool, oasis cubes, and peat pots.

The infused biochar could be further improved upon by initially or further infusing the biochar with micronutrients for mycorrhizal fungi, for example but not limited to humic acid, molasses, or sugar. The growth nutrient infused biochar would further expedite the colonization of the mycorrhizal fungi when physically combined with the inoculant and applied to seeds or plants.

Another improvement to the infused biochar would be to initially infusing or further infusing the biochar with the signaling molecules of mycorrhizal fungi. The signaling molecule infused biochar would further expedite the colonization of the mycorrhizal fungi when physically combined with the inoculant and applied to seeds or plants, as it would bring the mycorrhizae out of dormancy quicker and thus establish the mycorrhizal root system quicker.

Another method for establishing and improving mycorrhizal fungi colonies would be by growing mycorrhizae into the infused biochar and then applying the mycorrhizal fungi inoculated biochar to seeds or plants. Similar to a sand culture (Ojala and Jarrell 1980 http://jhbiotech.com/docs/Mycorrhizae-Article.pdf), a bed of infused biochar is treated with a recycled innoculanted nutrient solution by passing it through the bed multiple times.

E. Batch Treatment/Bulk Production

As demonstrated above, the treatment processes described above are particularly well suited for large scale production of biochar. The processes and biochars of the present invention provides a unique capability to select starting materials and pyrolysis techniques solely on the basis of obtaining a particular structure, e.g., pore size, density, pore volume, amount of open pores, interconnectivity, tortuosity, etc. Thus, these starting materials and processes can be selected without regard to adverse, harmful, phytotoxic side effects that may come from the materials and processes. This is possible, because the infiltration steps have the capability of mitigating, removing or otherwise address many, if not all of, those adverse side effects. In this manner, a truly custom biochar can be made, with any adverse side effects of the material selection and pyrolysis process being mitigated in later processing steps.

Further, the processes are capable of treating a large, potentially variable, batch of biochar to provide the same, generally uniform, predetermined customized characteristics for which treatment was designed to achieve, e.g., pH adjustment. Treatment can result in treated biochar batches in which 50% to 70% to 80% to 99% of the biochar particles in the batch have same modified or customized characteristic, e.g., deleterious pore surface materials mitigated, pore surface modified to provide beneficial surface, pore volume containing beneficial additives.

Accordingly, the ability to product large quantities of biochar having a high level of consistency, predictability and uniformity, provides numerous advantages in both large and small agricultural applications, among other things. For example, the ability to provide large quantities of biochar having predetermined and generally uniform properties will find applications in large scale agriculture applications. Thus, treated biochar batches from about 100 lbs up to 50,000+ lbs and between may have treated biochar particles with predetermined, uniform properties.

As the treated biochar batches are made up of individual biochar particles, when referring to uniformity of such batches it is understood that these batches are made up of tens and hundreds of thousands of particles. Uniformity is thus based upon a sampling and testing method that statistically establishes a level of certainty that the particles in the batch have the desired uniformity.

Thus, when referring to a treated batch of biochar as being "completely uniform" or having "complete uniformity" it means that at least about 99% (e.g., two nines) of all particles in the batch have at least one or more property or feature that is the same. When a treated batch of biochar is referred to as "substantially uniform" or having "substantial uniformity" it means that at least about 95% of all particles in the batch have at least one or more property or feature that is the same. When a treated batch of biochar is referred to as "essentially uniform" or having "essential uniformity" it means that at least about 80% of all particles in the batch have at least one or more property or feature that is the same. The batches can have less than 25%, 20% to 80%, and 80% or more particles in the batch that have at least one or more property or feature that is the same. Further, the batches can have less than 25%, 20% to 80%, and 80% or more particles in the batch that have at one, two, three, four, or all properties or features that are the same.

F. Applications

This advantage and solution leads to many others, which are presently known or may become later realized, including among other things the ability of the present inventions: to repurpose problematic biochars; to handle changing biochar material sources, e.g., seasonal and regional changes in the source of biomass; to provide for custom features and functions of biochar for particular soils, regions or agricultural purposes; to provide for large volumes of biochar having highly uniform and predictable properties; to improve the water retention capabilities of a biochar; to improve the nutrient retention capabilities of a biochar; to provide for larger volumes of biochar having uniform and custom properties; and to address many, the majority, if not all of the uniformity and consistency problems that have, prior to the present inventions, stifled the large scale adoption and use of biochars, and prevented the art from realizing the potential advantages of using biochar in agricultural settings.

Figure 28:
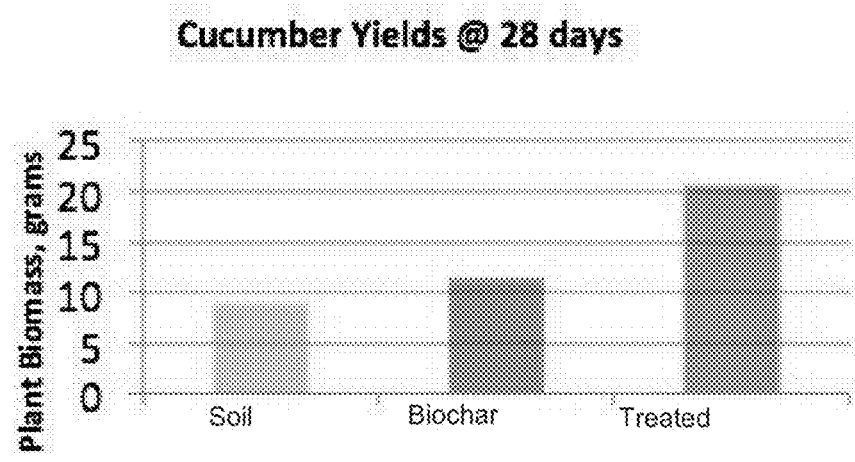
FIG. 28 is a chart showing the plant biomass of cucumber plants grown in standard soil, soil enhanced with raw biochar and soil enhanced with treated biochar.

Figure illustrates one example of the potential benefit of biochar and treated biochar to plant growth. FIG. 28 is a chart showing the plant biomass, measured in grams, of cucumber plants after twenty-eight days of growth in one soil type and in that soil type with biochar and treated biochar (identified as CoolTerra) added to the soil. As illustrated, the soil with the treated biochar yielded a cucumber plant over 2× the size, in weight, to the plant grown in the soil. The additional of raw biochar also showed a benefit to plant growth, but not to the same degree as the soil with the treated biochar.

Generally, treated biochar of the present inventions can be used throughout the world, in numerous soil types, agricultural applications, horticultural, large and small scale farming, organic farming, and in a variety of soil management applications and systems, and combinations and variations of these. In fact, this particular solution provides the capability to custom-manufacture biochar for a particular climate, environment, geographical area, soil type, or application by more precisely controlling key characteristics.

Examples of these applications include for example, use in acidic and highly weathered tropical field soils, use in temperate soils of higher fertility, use in large commercial applications, use for the production of large scale crops such as, soybean, corn, sugarcane and rice, in forestry applications, for golf courses (e.g., greens, fairways), for general purpose turf grasses, wine grapes, table grapes, raisin grapes, fruit and nut trees, ground fruits (e.g., strawberries, blueberries, blackberries), row crops (e.g., tomatoes, celery, lettuce, leafy greens), root crops (e.g., tubers, potatoes, beets, carrots), mushrooms, and combinations and variations of these.

Treated biochars and agriculture practices and methods, provide for improved soil structure, increased water retention capability, increased water holding ability of the soil over time, reduced runoff or leaching, increased holding ability for nutrients, increase holding of nutrients over time, and combinations and variations of these, and other features that relate to the increased holding and retention features and soil aggregation of the present biochars and processes. It further being understood that in addition to nutrients, other material additives, (e.g., herbicide, pesticide), can be utilized and benefit from the increased holding and retention capacities of the present biochars and methods.

Treated biochar may also be used in other applications, for example, such mixing with manure in holding ponds to potentially reduce gaseous nitrogen losses, soil remedial (for example absorption and capture of pesticide, contaminates, heavy metals, or other undesirable, disadvantageous soil components), ground water remediation, other bioremediations, storm water runoff remediation, mine remediation, mercury remediation and as a cattle or poultry feed additive.

Further, the present invention could be used to clean and/or infiltrate the pores of biochar with a variety of substances, for a number of purposes, including but not limited to, infiltrating the pores of biochar with nutrients, vitamins, drugs and/or other supplements, or a combination of any of the foregoing, for consumption by either humans and/or animals. The treated biochar may also be applied to animal pens, bedding, and/or other areas where animal waste is present to reduce odor and emission of unpleasant or undesirable vapors. Furthermore it may be applied to compost piles to reduce odor, emissions, and temperature to enable the use of the food waste and animal feed in composting. Biochar can also be applied to areas where fertilizer or pesticide runoff is occurring to slow or inhibit leaching and runoff. The biochar may also be treated with additives which make it easier to dispense or apply, such as non-toxic oils, anti-clumping/binding additives, surface drying agents, or other materials.

Biochar may also be used in other applications, for example, such mixing with manure in holding ponds to among other things potentially reduce gaseous nitrogen losses, soil remedial (for example absorption and capture of pesticide, contaminates, heavy metals, or other undesirable, disadvantageous soil components), ground water remediation, other bioremediations, storm water runoff remediation, mine remediation, mercury remediation, and as a cattle or poultry feed additive.

In general, in the agricultural application of biochar to soil, the biochar should be located near the soil's surface in the root zone, or in or adjacent to the rhizosphere, where the bulk of nutrient cycling and uptake by plants takes place. Although benefits may be obtained from the application of biochar in layers above, below, in and combinations and variation of these, the root zone, for example during landscaping for carbon sequestration, or if using biochar for moisture management. Layering of biochar at various depths above, below, in and combinations and variation of these, the root zone, the surface, and combinations and variations of these, may also be employed. The biochar layers may have different predetermined properties for each layer, based upon, for example, the depth of the layer, soil type, geography, crop, climate and other factors.

Those skilled in the art will further recognize that the present invention can be used on any type of soil application, including, but not limited to, the following: crops, turf grasses, potted plants, flowering plants, annuals, perennials, evergreens and seedlings. By way of example, treated biochar may be incorporated into or around the root zone of a plant. As most trees, rows, and specialty crops extract large percentage of their water from the first twenty-four inches below the soil surface, the above applications will generally be effective incorporating the biochar around the root zone from the top surface of the soil and up to a depth of 24" below the top surface of the soil, depending on the plant type and species, or alternatively, within a 24" radius surrounding the roots regardless of root depth or proximity from the top surface of the soil. When the plant roots are closer to the surface, the incorporation of the biochar within the top 2-6" inches of the soil surface may also be effective. Greater depths are more beneficial for plants having larger root zones, such as trees.

In certain examples of biochar applications, the treated biochar can be applied in amounts (e.g., rates of addition as measured by weight of treated biochar per area of field) of from about 0.00001 ton of treated biochar per acre to about 150 tons of treated biochar per acre, from about 0.001 tons of treated biochar per acre to about 100 tons of treated biochar per acre, and from about 0.01 tons of treated biochar per acre to about 10 tons of treated biochar per acre, although larger and smaller amounts may be used. In general, it has been observed that treatment can dramatically reduce the amount of biochar needed to see efficacy in some agricultural applications—by a factor of 10 or more. Additional rates of from about ½ tons of treated biochar to about 10 tons of treated biochar may be used. For example, application rates of 1 ton of treated biochar was added per acre to a soil for a lettuce crop where the soil had a pH of about 7. In another example, about 3 tons per acre of treated biochar was added to soil for a strawberry crop. In these examples, the plants showed enhanced growth rates and yields. In one instance, 0.015 tons per acre of treated biochar was added to soil for a wheat crop, in close proximity to the seeds being planted, and a statistically significant yield response was observed.

Generally, for conventional field cropping systems, biochar can be preferably added using existing farm equipment and incorporated into existing farming operations. For example, treated biochar can be applied and incorporated together with lime, since lime is often applied as a fine solid, which must be well incorporated into soil. However, it is also contemplated that the examples of the present inventions may give rise to new equipment and utilizations based upon the features, performance and capabilities of the present inventions. Generally, treated biochar may be applied to fields, by way of example through the use of manure or compost spreaders, lime spreaders, plowing method (e.g., from hand hoes, animal draft plows, disc harrows, chisels, rotary hoes, etc.), large scale tillage equipment, including rotary tillers, mulch finishers, draw offset discs, and disc harrows (such as for example JOHN DEERE DH51, DH52F, PC10, RT22, and RC22). Treated biochar may also be applied by modified large scale nutrient applicators (such as, for example, JOHN DEERE 2410C, 2510H, 25105 Strip-Till Medium Residue Applicator), large scale draw dry spreaders (such as JOHN DEERE DN345), large scale no-till planters, large scale dry fertilizer sub-surface applicators, and liquid slurry surface or subsurface applicators, pesticide or insecticide applicators, seed drills, seeders, and other mechanisms for applying a solid or liquid flowable input into the soil. Similar, and various other types of large farming, and earth moving and manipulation equipment may be used to apply the treated biochar to the field, such as for example, drop spreaders or drills.

For example, treated biochar may be applied using banding techniques, which is an operation involving applying the biochar in a narrow band, using equipment that cuts the soil open, without disturbing the entire soil surface. Using this technique the biochar can be placed inside the soil while minimizing soil disturbance, making it possible to apply biochar after crop establishment, among other applications.

In other examples, treated biochar may be mixed with other soil amendments, or other materials, such as for example manure, sand, topsoil, compost, turf grass substrate, peat, peat moss, or lime before soil application, which are already scheduled or part of the existing operations, and in this manner by combining these steps (e.g., biochar application with existing application step) can improve efficiency by reducing the number of field operations required. In other examples, treated biochar can also be mixed with liquid, (e.g., liquid manures) and applied as a slurry. Finer biochar particles may be preferably used with this type of slurry application using existing application equipment, and dust problems associated with these finer particles may be mitigated, managed or eliminated.

In further examples, treated biochar can be top dressed on perennial pastures or other perennial vegetation, such as spaces between fruit trees in orchards. Treated biochar may also be applied with individual plants while transplanting or mixed with topsoil and other amendments while preparing raised beds. In forestry or similar operations where replanting of seedlings takes place, treated biochar can be applied by broadcasting (e.g., surface application) or incorporation over the entire planting area, it can be added in the planting holes, and combinations and variations of these. Before or after tree establishment, biochar could also be applied by traditional and subsurface banding or top-dressed over perennial vegetation in orchards, but care should be taken to minimize root damage and soil compaction.

In other examples of applications, treated biochar can be applied in trenches radiating out from the base of established trees ("radial trenching") or in holes dug at some distance from the base of the tree ("vertical mulching"); biochar could also potentially be applied to soil using "air excavation tools". These tools use pressurized air to deliver material, e.g., compost, under the soil surface and reduce compaction. Alternatively, the soil around tree roots can be excavated and treated biochar applied before covering with soil.

While, in some examples, particle size distribution of treated biochar materials may vary widely depending on the feedstock and the pyrolysis technique used to produce the biochar, uniformity if required or preferred, can be achieved by various milling and grinding techniques that may be employed during processing or during the distribution and application to soil. When smaller particles are utilized, and in particular for surface applications, care should be taken to apply the treated biochar in ways that minimize loss due to wind or water erosion.

As set forth above, the treated biochar of the present invention may be used in various agriculture activities, and the fields of edaphology and pedology, as well as other activities and in other fields. Additionally, the treated biochar may be used, for example, with: farming systems and technologies, operations or activities that may be developed in the future; and with such existing systems, operations or activities which may be modified, in-part, based on the teachings of this specification. Further, the various treated biochar and treatment processes set forth in this specification may be used with each other in different and various combinations. Thus, for example, the processes and resulting biochar compositions provided in the various examples provided in this specification may be used with each other; and the scope of protection afforded the present inventions should not be limited to any particular example, process, configuration, application or arrangement that is set forth in a particular example or figure.

Although this specification focuses on agriculture, soil modification and plant growth, it should be understood that the materials, compositions, structures, apparatus, methods, and systems, taught and disclosed herein, may have applications and uses for many other activities in addition to agriculture for example, as filters, additives, and in remediation activities, among other things.

It being understood that one or more of these may be preferred for one application, and another of these may be preferred for a different application. Thus, these are only a general list of preferred features and are not required, necessary and may not be preferred in all applications and uses.

It is noted that there is no requirement to provide or address the theory underlying the novel and groundbreaking functionality, performance or other beneficial features and properties that are the subject of, or associated with, embodiments of the present inventions. Nevertheless, to the extent that various theories are provided in this specification to further advance the art in this important area. These theories put forth in this specification, and unless expressly stated otherwise, in no way limit, restrict or narrow the scope of protection to be afforded the claimed inventions. These theories may not be required or practiced to utilize the present inventions. It is further understood that the present inventions may lead to new, and heretofore unknown theories to explain the functionality, performance or other beneficial features and properties that are the subject of, or associated with, embodiments of the methods, articles, materials, and devices of the present inventions; and such later developed theories shall not limit the scope of protection afforded the present inventions.

Those skilled in the art will recognize that there are other methods that may be used to treat biochar in a manner that forces the infusion of liquids into the pores of the biochar without departing from the scope of the invention. The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

What is claimed is:

1. A plurality of porous carbonaceous particles where a hydrophobicity of the plurality of porous carbonaceous particles under the MED test method has an index of 5 or less and where the plurality of porous carbonaceous particles exhibit weight loss of more than 1% in the interval between 43 and 60° C. when performing the Bontchev-Cheyne Test.

2. The plurality of porous carbonaceous particles of claim 1, where at least 75% of the particles, measured by weight or volume, have a particle size less than or equal to 10 mm.

3. The plurality of porous carbonaceous particles of claim 1, where the plurality of porous carbonaceous particles have been treated to have at least 10% of the pores, by volume, filled with an infiltrate.

4. The plurality of porous carbonaceous particles of claim 1, where the plurality of porous carbonaceous particles contains at least 55% carbon by weight.

5. The plurality of porous carbonaceous particles of claim 1, where the bulk density of the plurality of porous carbonaceous particles in the batch, measured by weight, is between 0.1 and 0.6 g/cm3.

6. The plurality of porous carbonaceous particles of claim 1, where the plurality of porous carbonaceous particles have a ratio of macropore volume to total pore volume greater than or equal to 50%.

7. The plurality of porous carbonaceous particles of claim 1, where the porous carbonaceous particles contain less than 5% by weight of volatile organic compounds.

8. The plurality of porous carbonaceous particles of claim 1, where the plurality of porous carbonaceous particles have a cation exchange capacity of greater than or equal to 5 milliequ/l.

9. The plurality of porous carbonaceous particles of claim 1, where the plurality of porous carbonaceous particles have an anion exchange capacity of greater than or equal to 5 milliequ/l.

10. The plurality of porous carbonaceous particles of claim 1, where the plurality of porous carbonaceous particles have a water holding capacity greater than 30% by weight.

11. The plurality of porous carbonaceous particles of claim 1, where the plurality of porous carbonaceous particles have been treated by rapidly infusing the additive into the pores of the plurality of porous carbonaceous particles using a vacuum processing treatment.

12. The plurality of porous carbonaceous particles of claim 1, where the plurality of porous carbonaceous particles have been treated by infusing the additive into the pores of the plurality of porous carbonaceous particles using a surfactant infusion treatment.

13. The plurality of porous carbonaceous particles of claim 1, where the plurality of porous carbonaceous particles have been treated by infusing the additive into the pores of the plurality of porous carbonaceous particles including both a surfactant infusion treatment and a vacuum infusion treatment.

14. The plurality of porous carbonaceous particles of claim 1, where the additive is a soil enhancing agent selected from the group consisting of water, water solutions of salts, inorganic and organic liquids of different polarities, liquid organic compounds or combinations of organic compounds and solvents, mineral and organic oils, slurries and suspensions, supercritical liquids, fertilizers, plant growth promoting rhizobacteria, free-living and nodule-forming nitrogen fixing bacteria, organic decomposers, nitrifying bacteria, phosphate solubilizing bacteria, biocontrol agents, bioremediation agents, saprotrophic fungi, ectomycorrhizae, and endomycorrhizae.

15. A plurality of porous carbonaceous particles where the plurality of porous carbonaceous particles exhibit weight loss of more than 1% in the interval between 43 and 60° C. when performing the Bontchev-Cheyne Test.

16. The plurality of porous carbonaceous particles of claim 15 where at least 75% of the plurality of porous carbonaceous particles have a particle size less than or equal to 10 mm.

17. The plurality of porous carbonaceous particles of claim 15 where the plurality of porous carbonaceous particles have a ratio of macropore volume to total pore volume greater than or equal to 50%.

18. The plurality of porous carbonaceous particles of claim 15 where the plurality of porous carbonaceous particles have a water holding capacity greater than 30% by weight.

19. The plurality of porous carbonaceous particles of claim 15, where the porous carbonaceous particles have been treated by rapidly infusing a liquid into the pores of the plurality of porous carbonaceous particles.

20. The plurality of porous carbonaceous particles of claim 19, where the treatment for rapidly infusing the liquid into the pores of the plurality of porous carbonaceous particles is a vacuum processing treatment.

21. A plurality of porous carbonaceous particles where the plurality of porous carbonaceous particles in the batch meet EU Feed limit for dioxins equal to or less than 0.75 ng/kg WHO-PCDD/F-TEQ//kg and where the plurality of porous carbonaceous particles exhibit weight loss of more than 1% in the interval between 43 and 60° C. when performing the Bontchev-Cheyne Test.

22. The plurality of porous carbonaceous particles of claim 21 where the plurality of porous carbonaceous particles have been treated by infusing a infiltrate into at least 10% of the pores, by volume, of the plurality of pores of the porous carbonaceous particles.

23. The plurality of porous carbonaceous particles of claim 21 where at least 75% of the porous carbonaceous particles, measured by weight or volume, have a particle size less than or equal to 10 mm.

24. The plurality of porous carbonaceous particles of claim 21 where the plurality of porous carbonaceous particles contains at least 55% carbon by weight.

25. The plurality of porous carbonaceous particles of claim 21 where the plurality of porous carbonaceous particles have at least 70% of pores, by volume, measure less than 50,000 nanometers using mercury porosimetry testing.

* * * * *